United States Patent [19]

Bradfisch et al.

[11] Patent Number: 5,827,514
[45] Date of Patent: Oct. 27, 1998

[54] PESTICIDAL COMPOSITIONS

[75] Inventors: Gregory A. Bradfisch; Mark Thompson, both of San Diego; George E. Schwab, La Jolla, all of Calif.

[73] Assignee: Mycogen Corporation, San Diego, Calif.

[21] Appl. No.: 598,305

[22] Filed: Feb. 8, 1996

Related U.S. Application Data

[63] Continuation of Ser. No. 349,867, Dec. 6, 1994, Pat. No. 5,508,264.
[51] Int. Cl.$^6$ .............................. A01N 63/00; C12N 1/21; C12N 5/14; C12P 21/02
[52] U.S. Cl. .................. 424/93.2; 424/93.1; 424/93.3; 435/69.1; 435/69.7; 435/252.3; 435/410; 435/418; 435/419
[58] Field of Search .............................. 514/12; 435/69.1, 435/252.3, 69.7, 410, 418, 419; 424/93.1, 93.2, 93.3

[56] References Cited

U.S. PATENT DOCUMENTS

| | | | |
|---|---|---|---|
| 4,448,885 | 5/1984 | Schnepf et al. | 435/253 |
| 4,467,036 | 8/1984 | Schnepf et al. | 435/317 |
| 4,797,276 | 1/1989 | Hernstadt et al. | 424/84 |
| 4,849,217 | 7/1989 | Soares et al. | 424/93 |
| 4,853,331 | 8/1989 | Hernstadt et al. | 435/252.1 |
| 4,918,006 | 4/1990 | Ellar et al. | 435/69.1 |
| 4,948,734 | 8/1990 | Edwards et al. | 435/252.5 |
| 5,055,294 | 10/1991 | Gilroy | 424/93 |
| 5,128,130 | 7/1992 | Gilroy et al. | 424/93 |
| 5,151,363 | 9/1992 | Payne | 435/252.5 |
| 5,527,883 | 6/1996 | Thompson et al. | 530/350 |

FOREIGN PATENT DOCUMENTS

| | | |
|---|---|---|
| 0589110 | 3/1994 | European Pat. Off. . |
| 9116434 | 10/1991 | WIPO . |
| 0606110 | 7/1994 | WIPO . |
| 9530752 | 11/1995 | WIPO . |
| 9530753 | 11/1995 | WIPO . |
| 9605314 | 2/1996 | WIPO . |

OTHER PUBLICATIONS

Gaetner, F.H., L. Kim (1988) "Current Applied Recombinant DNA Projects" TIBTECH 6:s4–S7.

Gaetner, F.H. (1988) Cellular delivery systems for insecticidal proteins: living and non–living microorganism in Controlled Deliver of Crop–Protection Agents, pp. 245–255.

Couch, T.L. (1980) "Mosquito Pathogenicity of *Bacillus thuringiensis* var. *israelensis*" Developments in Industrial Microbiology 22:61–76.

Beegle, C.C. (1978) "Use of Entomogenous Bacteria in Agroecosystems" in Developments in Industrial Microbiology 20:97–104.

Krieg, A. et al. (1983) "*Bacillus thuringiensis* var. *tenebrionis:* ein neuer, gegenuber Larven von Coleopteren Wirksamer Pathotyp" Z. ang. Ent. 96:500–508.

Hofte, H., H.R. Whiteley (1989) "Insecticidal Crystal Proteins of *Bacillus thuringiensis*" Microbiological Reviews 52(2):242–255.

Feitelson, J.S. et al. (1992) "*Bacillus thuringiensis:* Insects and Beyond" Bio/Technology 10:271–275.

Schnepf, H.E., H.R. Whiteley (1981) "Cloning and expression of the *Bacillus thuringiensis* crystal protein gene in *Escherichia coli*" Proc. Natl. Acad. Sci. USA 78(5):2893–2897.

Li, J., J. Carroll, D.J. Ellar (1991) "Crystal structure of insecticidal δ–endotoxin from *Bacillus thuringiensis* at 2.5 A resolution" Nature 353:815–821.

Arivdson, H. et al. (1989) "Specificity of *Bacillus thuringiensis* for lepidopteran larvae: factors involved in vivo and in the structure of a purified protoxin" Molecular Microbiology 3(11):1533–1543.

Choma, C.T. et al. (1990) "Unusual proteolysis of the protoxin and toxin from *Bacillus thuringiensis*" Eur. J. Biochem. 189:523–527.

Haider, M.Z. et al. (1986) "Specificity of *Bacillus thuringiensis* var. *Colmeri* insecticidal δ–endotoxin is determined by differential proteolytic processing of the processing of the protoxin" Eur. J. Biochem. 156:531–540.

Aronson, A.I. et al. (1991) "The Solubility of Inclusion Proteins from *Bacillus thuringiensis* Is Dependent upon Protoxin Composition and Is a Factor in Toxicity to Insects" Appl. Environ. Microbiol. 57(4):981–986.

Honee, G. et al. (1991) "The C–terminal domain of the toxic fragment of a *Bacillus thuringiensis* crystal protein determines receptor binding" Molecular Microbiology 5(11):2799–2806.

Honee, G. et al. (1990) "A Translation Fusion Product of Two Different Insecticidal Crystal Protein Genes of *Bacillus thuringiensis* Exhibits an Enlarged Insecticidal Spectrum" Appl. Environ. Microbiol. 56(3):823–825.

Moar, W.J. et al. (1986) "Potentiation of *Bacillus thuringiensis* var. *kurstaki* with Thuringiensin on Beet Armyworm (Lepidoptera: Noctuidae)" Journal of Economic Entomology 79(6):1443–1446.

Chilcott, C.N., D.J. Ellar (1988) "Comparative Toxicity of *Bacillus thuringiensis* var. *israelensis* Crystal Proteins in in vivo and in vitro" Journal of General Microbiology 134:2551–2558.

(List continued on next page.)

Primary Examiner—Kawai Lau
Attorney, Agent, or Firm—Saliwanchik, Lloyd & Saliwanchik

[57] ABSTRACT

Disclosed are compositions and processes for controlling lepidopteran pests. These compositions comprise synergistic combinations of a CryIF chimeric and CryIA(c) chimeric *Bacillus thuringiensis* δ-endotoxin. These compositions have been found to exhibit excellent activity against lepidopteran pests.

35 Claims, 10 Drawing Sheets

OTHER PUBLICATIONS

Wu, D., F.N. Chang (1985) "Synergism in Mosquitocidal activity of 26 and 65 kDa proteins from *Bacillus thuringiensis* subsp. *israelensis* crystal" FEBS LETTERS 190(2):232–236.

Angsuthanasombat, C. et al. (1992) "Comparison of *Bacillus thuringiensis* subsp. *israelensis* CryIVA and CryIVB cloned toxins reveals synergism in vivo" FEMS Microbiology Letters 94:63–68.

Tabashnik, B.E. (1992) "Evaluation of Synergism among *Bacillus thuringiensis* Toxins" Applied and Environmental Microbiology 58(10):3343–3346.

Ge, A. et al. (1991) "Functional Domains of *Bacillus thuringiensis* Insecticidal Crystal Proteins" The Journal of Biological Chemistry 266(27):17954–17958.

Chambers, J.A. et al. (1991) "Isolation and Characterization of a Novel Insecticdal Crystal Protein Gene from *Bacillus thuringiensis* subsp. *aizawai*" Jouranl of Bacteriology 173(13):3966–3976.

Chestukhina, G.G. et al. (1994) "Production of Multiple δ–endotoxins produced by strains of the subspecies *gallariae* and *wuhanensis*" Canadian Journal of Microbiology 40(12):1026–1034.

```
          1
Cons      MENNIQNQCV PYNCLNNPEV EILNEERSTG RLPLDISLSL TREFLLSEFVP GVGVAFGLFD LIWGFITPSD WSLFLLQIEQ LIEQRIETLE        90

91
Cons      RNRAITTLRG LADSYEIYIE ALREWEANPN NAQLREDVRI RFANTDDALI TAINNFTLTS FEIPLLSVYV QAANLHLSLL RDAVSFGQGW       180

181
Cons      GLDIATVNNH YNRLINLIHR YTKHCLDTYN QGLENLRGTN TRQWARFNQF RRDLTLTVLD IVALFPNYDV RTYPIQTSSQ LTREIYTSSV       270

271
Cons      IEDSPVSANI PNGFNRAEFG VRPPHLMDFM NSLFVTAETV RSQTVWGGHL VSSRNTAGNR INFPSYGVFN PGGAIWIADE DPRPFYRTLS       360

361
Cons      DPVFVRGGFG NPHYVLGLRG VAFQQTGTNH TRTFRNSGTI DSLDEIPPQD NSGAPWNDYS HVLNHVTFVR WPGEISGSDS WRAPMFSWTH       450

451
Cons      RSATPTNTID PERITQIPLV KAHTLQSGTT VVRGPGFTGG DILRRTSGGP FAYTIVNING QLPQRYRARI RYASTTNLRI YVTVAGERIF       540

541                                                                 t
Alt                                                                           i
Alt                                                                      e a      p l i
Cons      AGQFNKTMDT GDPLTFQSFS YATINTAFTF PMSQSSFTVG ADTFSSGNEV YIDRFELIPV TATfEAEYdL ERAQKAVNEL FTSSNQIGLK       630

631            e                      s
Alt                      r                                        s                    p
Alt        n  Q      t   ng                                     kd  p        g  g    r
Cons      TDVTDYHIDr VSNLIVECLSD EFCLDEKKEL SEKVKHAKRL SDERNLLQDP NFRGINRQLD RGWRGSTDIT IQGGDDVFKE NYVTLLGTFD       720

721                                                            vq
Alt        l                              p       e                      fe  s   rKCGE PNRCAPHLEW NPDLDCSCRD
Alt
Cons      ECYPTYLYQK IDESKLKAYT RYQLRGYIED SQDLEIYLIR YNAKHETVNV PGTGSLWPLS APSPIG----                            810
```

Fig. 9B

```
       811                                    e    i        gra
Alt    GE                            i        d             ql
Cons   --KCAHHSHH FSLDIDVGCT DLNEDLGVWV IFKIKTQDGH ARLGNLEFLE EK-PLVGEAL ARVKRAEKKW RDKREKLEWE TNIVYKEAKE
                                                                                                      900

901                              q              t         r  q              d        k    f
Alt                                                             vg
Cons   SVDALFVNSQ YDRLQADTNI AMIHAADKRV HSIREAYLPE LSVIPGVNAA IFEELEGRIF TAFSLYDARN VIKNGDFNNG LSCWNVKGHV
                                                                                                      990

991     q                                                             t                   f
Alt                                                                                                     n   g
Cons   DVEEQNNHRS VLVVPEWEAE VSQEVRVCPG RGYILRVTAY KEGYGEGCVT IHEIENNTDE LKFSNCVEEE VYPNNTVTCN DYTATQEEYE
                                                                                                     1080

1081  a   c       et g  y           v                                                q
Alt
Cons   GTYTSRNRGY DGAYESNSSV PADYASAYEE KAYTDGRRDN PCESNRGYGD YTPLPAGYVT KELEYFPETD KVWIEIGETE GTFIVDSVEL
                                                                                                     1170

1171
Cons   LLMEE
```

PESTICIDAL COMPOSITIONS

This is a continuation of application Ser. No. 08/349,867, filed Dec. 6, 1994 now U.S. Pat. No. 5,508,264.

BACKGROUND OF THE INVENTION

The soil microbe *Bacillus thuringiensis* (*B.t.*) is a Gram-positive, spore-forming bacterium characterized by parasporal crystalline protein inclusions. These inclusions often appear microscopically as distinctively shaped crystals. The proteins can be highly toxic to pests and specific in their toxic activity. Certain *B.t.* toxin genes have been isolated and sequenced, and recombinant DNA-based *B.t.* products have been produced and approved for use. In addition, with the use of genetic engineering techniques, new approaches for delivering these *B.t.* endotoxins to agricultural environments are under development, including the use of plants genetically engineered with endotoxin genes for insect resistance and the use of stabilized intact microbial cells as *B.t.* endotoxin delivery vehicles (Gaertner, F. H., L. Kim [1988] *TIBTECH* 6:S4–S7). Thus, isolated *B.t.* endotoxin genes are becoming commercially valuable.

Until the last ten years, commercial use of *B.t.* pesticides has been largely restricted to a narrow range of lepidopteran (caterpillar) pests. Preparations of the spores and crystals of *B. thuringiensis* subsp. *kurstaki* have been used for many years as commercial insecticides for lepidopteran pests. For example, *B. thuringiensis* var. *kurstaki* HD-1 produces a crystal called a δ-endotoxin which is toxic to the larvae of a number of lepidopteran insects.

In recent years, however, investigators have discovered *B.t.* pesticides with specificities for a much broader range of pests. For example, other species of *B.t.*, namely *israelensis* and *tenebrionis* (a.k.a. *B.t.* M-7, a.k.a. *B.t. san diego*), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255). See also Couch, T. L. (1980) "Mosquito Pathogenicity of *Bacillus thuringiensis* var. *israelensis,*" *Developments in Industrial Microbiology* 22:61–76; Beegle, C. C., (1978) "Use of Entomogenous Bacteria in Agroecosystems," *Developments in Industrial Microbiology* 20:97–104. Krieg, A., A. M. Huger, G. A. Langenbruch, W. Schnetter (1983) *Z. ang. Ent.* 96:500–508, describe *Bacillus thuringiensis* var. *tenebrionis*, which is reportedly active against two beetles in the order Coleoptera. These are the Colorado potato beetle, *Leptinotarsa decemlineata*, and *Agelastica alni*.

Recently, new subspecies of *B.t.* have been identified, and genes responsible for active δ-endotoxin proteins have been isolated (Höfte, H., H. R. Whiteley [1989] *Microbiological Reviews* 52(2):242–255). Höfte and Whiteley classified *B.t.* crystal protein genes into 4 major classes. The classes were CryI (Lepidoptera-specific), CryII (Lepidoptera- and Diptera-specific), CryIII (Coleoptera-specific), and CryIV (Diptera-specific). The discovery of strains specifically toxic to other pests has been reported. (Feitelson, J. S., J. Payne, L. Kim [1992] *Bio/Technology* 10:271–275).

The cloning and expression of a *B.t.* crystal protein gene in *Escherichia coli* has been described in the published literature (Schnepf, H. E., H. R. Whiteley [1981] *Proc. Natl. Acad. Sci. USA* 78:2893–2897). U.S. Pat. No. 4,448,885 and U.S. Pat. No. 4,467,036 both disclose the expression of a *B.t.* crystal protein in *E. coli*. Hybrid *B.t.* crystal protein genes have been constructed that exhibit increased toxicity and display an expanded host range to a target pest. See U.S. Pat. Nos. 5,128,130 and 5,055,294. U.S. Pat. Nos. 4,797,276 and 4,853,331 disclose *B. thuringiensis* strain *san diego* (a.k.a. *B.t. tenebrionis*, a.k.a. M-7) which can be used to control coleopteran pests in various environments. U.S. Pat. No. 4,918,006 discloses *B.t.* toxins having activity against dipterans. U.S. Pat. No. 4,849,217 discloses *B.t.* isolates which have activity against the alfalfa weevil. U.S. Pat. No. 5,151,363 and U.S. Pat. No. 4,948,734 disclose certain isolates of *B.t.* which have activity against nematodes.

As a result of extensive research and investment of resources, other patents have issued for new *B.t.* isolates and new uses of *B.t.* isolates. However, the discovery of new *B.t.* isolates and new uses of known *B.t.* isolates remains an empirical, unpredictable art.

A majority of *Bacillus thuringiensis* δ-endotoxin crystal protein molecules are composed of two functional segments. The protease-resistant core toxin is the first segment and corresponds to about the first half of the protein molecule. The three-dimensional structure of a core segment of a cryIIIA *B.t.* δ-endotoxin is known and it is proposed that all related toxins have that same overall structure (Li, J., J. Carroll, D. J. Ellar [1991] *Nature* 353:815–821). The second half of the molecule is the second segment. For purposes of this application, this second segment will be referred to herein as the "protoxin segment." The protoxin segment is believed to participate in toxin crystal formation (Arvidson, H., P. E. Dunn, S. Strand, A. I. Aronson [1989] *Molecular Microbiology* 3:1533–1534; Choma, C. T., W. K. Surewicz, P. R. Carey, M. Pozsgay, T. Raynor, H. Kaplan [1990] *Eur. J. Biochem.* 189:523–527). The full 130 kDa toxin molecule is rapidly processed to the resistant core segment by protease in the insect gut. The protoxin segment may thus convey a partial insect specificity for the toxin by limiting the accessibility of the core to the insect by reducing the protease processing of the toxin molecule (Haider, M. Z., B. H. Knowles, D. J. Ellar [1986] *Eur. J. Biochem.* 156:531–540) or by reducing toxin solubility (Aronson, A. I., E. S. Han, W. McGaughey, D. Johnson [1991] *Appl. Environ. Microbiol.* 57:981–986).

Chimeric proteins joined within the toxin domains have been reported between CryIC and CryIA(b) (Honee, G., D. Convents, J. Van Rie, S. Jansens, M. Perferoen, B. Visser [1991] *Mol. Microbiol.* 5:2799–2806); however, the activity of these chimeric proteins was either much less, or undetectable, when compared to CryIC on a relevant insect.

Honee et al. (Honee, G., W. Vriezen, B. Visser [1990] *Appl. Environ. Microbiol.* 56:823–825) also reported making a chimeric fusion protein by linking tandem toxin domains of CryIC and CryIA(b). The resulting protein had an increased spectrum of activity equivalent to the combined activities of the individual toxins; however, the activity of the chimeric was not increased toward any one of the target insects.

When toxins or biologically active agents are blended together, the biological activity of the resulting mixture can be affected in several ways. The resultant biological activity can be the sum of the activity of each of the toxins. Biological activity of the mixture may be less than the sum of the activity of each of the agents, or the resultant activity may be greater than the sum of the activity of each of the agents.

A nucleotide β-exotoxin produced by a particular *B.t.* strain was found to act in synergy with the protein δ-endotoxins in *B.t.* var. *kurstaki* to yield increased activity against the lepidopteran pest *Spodoptera exigua* (Moar, W. J., W. L. A. Osbrink, J. T>Trumble [1986] *J. Econ. Entomol.* 79:1443–1446). Enhanced toxicity to mosquito larvae occurs with the mixture of the 27 kDa and the 65 or 130 kDa proteins from *B.t.* var. *israelensis* (Chilcott, C. N., D. J. Ellar [1988] *J. Gen. Microbiology* 132:2551–2558; Yu et al., 1987; Wu, D., F. N. Chang [1985] *FEBS* 190(2):232–236). The CryIVA and CryIVB toxins from *B.t.* var. *israelensis* have also been used together (Angsuthanasomat, C., N. Crickmore, D. J. Ellar [1992] *FEMS Microbiol. Lett.* 94:63–68).

BRIEF SUMMARY OF THE INVENTION

The subject invention concerns the discovery of advantageous increased activity against lepidopteran pests achieved by the combination of two *Bacillus thuringiensis* (*B.t.*) δ-endotoxin proteins. More specifically, a CryIF chimeric toxin combined with a CryIA(c) chimeric toxin act in synergy to yield unexpected enhanced toxicity to lepidopteran pests.

The synergistic effect of the subject invention may be achieved by combining, as in a mixture, isolates that each produce one of the toxin proteins. Recombinant hosts engineered to express both of the toxins of the subject invention can also be used to achieve the synergistic effect. Suitable recombinant hosts include prokaryotes and lower eukaryotes, as well as plants.

Chimeric CryIF genes useful according to the subject invention can be assembled that substitute a heterologous protoxin segment for all or part of the native cryIF protoxin segment. In particular, all or part of the protoxin-encoding region of a cryIA(b) gene can be used in place of all or part of the region which encodes the protoxin for a native cryIF toxin. Similarly, a chimeric gene can be constructed wherein the region encoding all or part of the protoxin of a cryIF toxin is replaced by DNA encoding all or part of the protoxin of a cryIA(c)/cryIA(b) chimeric gene. In a specific embodiment, the cryIA(c)/cryIA(b) chimeric gene is that which has been denoted 436 and which is described in U.S. Pat. No. 5,128,130. This gene can be obtained from the plasmid in *P. fluorescens* MR436.

The chimeric gene can be introduced into a wide variety of microbial or plant hosts. A transformed host expressing the chimeric gene can be used to produce the lepidopteran-active toxins of the subject invention. Transformed hosts can be used to produce the insecticidal toxins or, in the case of a plant cell transformed to produce the toxins, the plant will become resistant to insect attack. The subject invention further pertains to the use of the chimeric toxins, or hosts containing the genes encoding the chimeric toxins, in methods for controlling lepidopteran pests.

Still further, the invention includes combinations of substantially intact treated *B.t.* cells, or recombinant cells expressing the genes and producing the toxins of the invention. The cells can be treated to prolong the pesticidal activity when the substantially intact cells are applied to the environment of the target pest. Such treatment can be by chemical or physical means, or a combination of chemical and physical means, so long as the technique does not deleteriously affect the synergistic properties of the pesticides, nor diminish the cellular capability in protecting the pesticides. The treated cell acts as a protective coating for the pesticidal toxins. The toxins become available to act as such upon ingestion by a target pest.

BRIEF DESCRIPTION OF THE DRAWINGS

Figure 3:
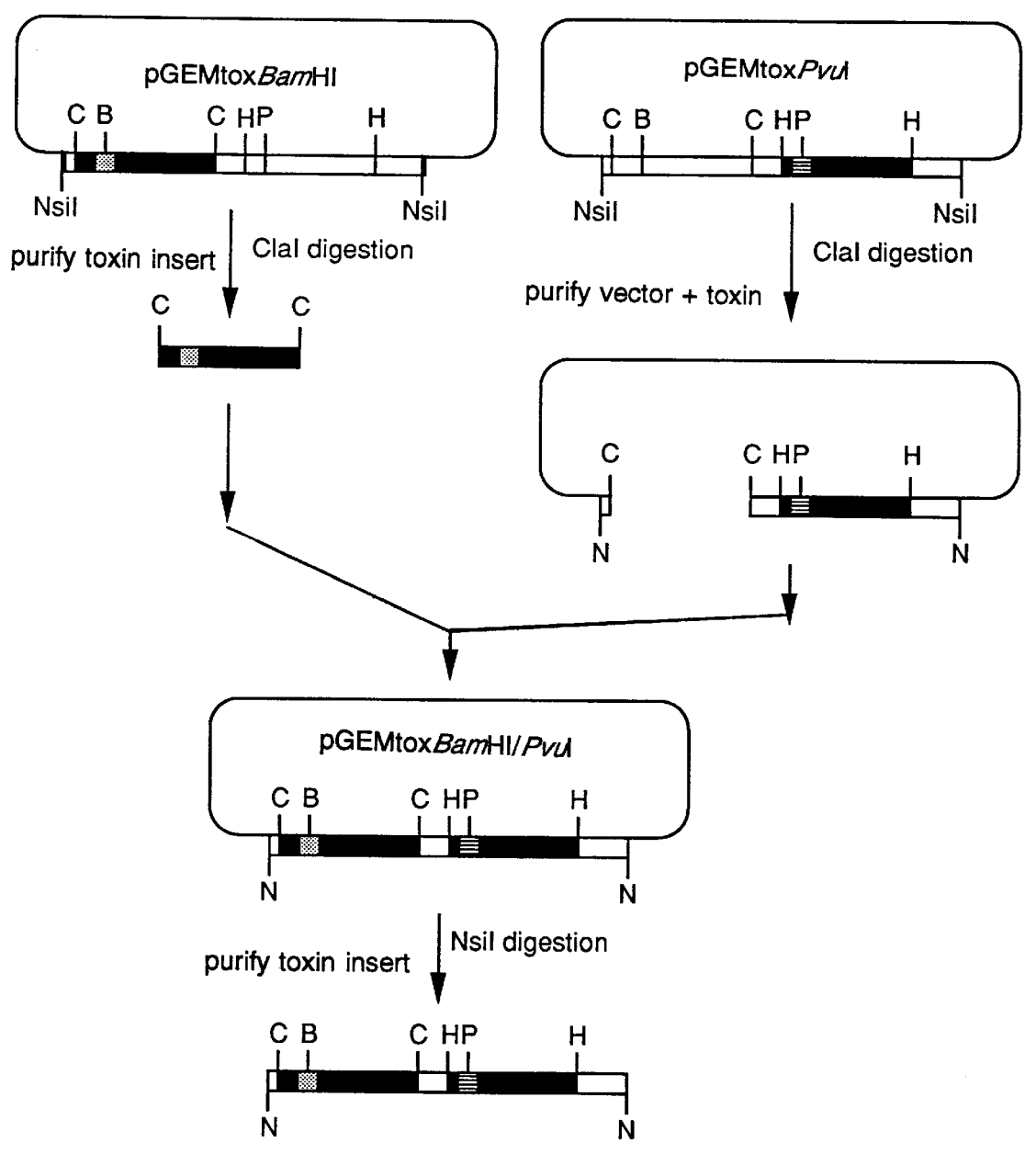

FIG. 3 The DNA fragment containing the BamHI mutation is used to replace the homologous fragment in pGEMtoxPvuI. The resulting plasmid which contains both cloning sites is pGEMtoxBamHI/PvuI. To construct an expression plasmid, the toxin-containing NsiI fragment is excised for cloning into the pTJS260 broad host-range vector. B=BamHI, C=ClaI, H=HindIII, P=PvuI.

FIG. 9 A CryIF/CryIA(b) chimeric protein sequence and residue-by-residue substitutions. The 'Cons' line shows a CryIF/CryIA(b) chimeric sequence. The 'Alt' lines show residue-by-residue substitutions found in the 436 protein, CryIA(b) variant proteins and CryIF protoxins.

BRIEF DESCRIPTION OF THE SEQUENCES

Figure 1:
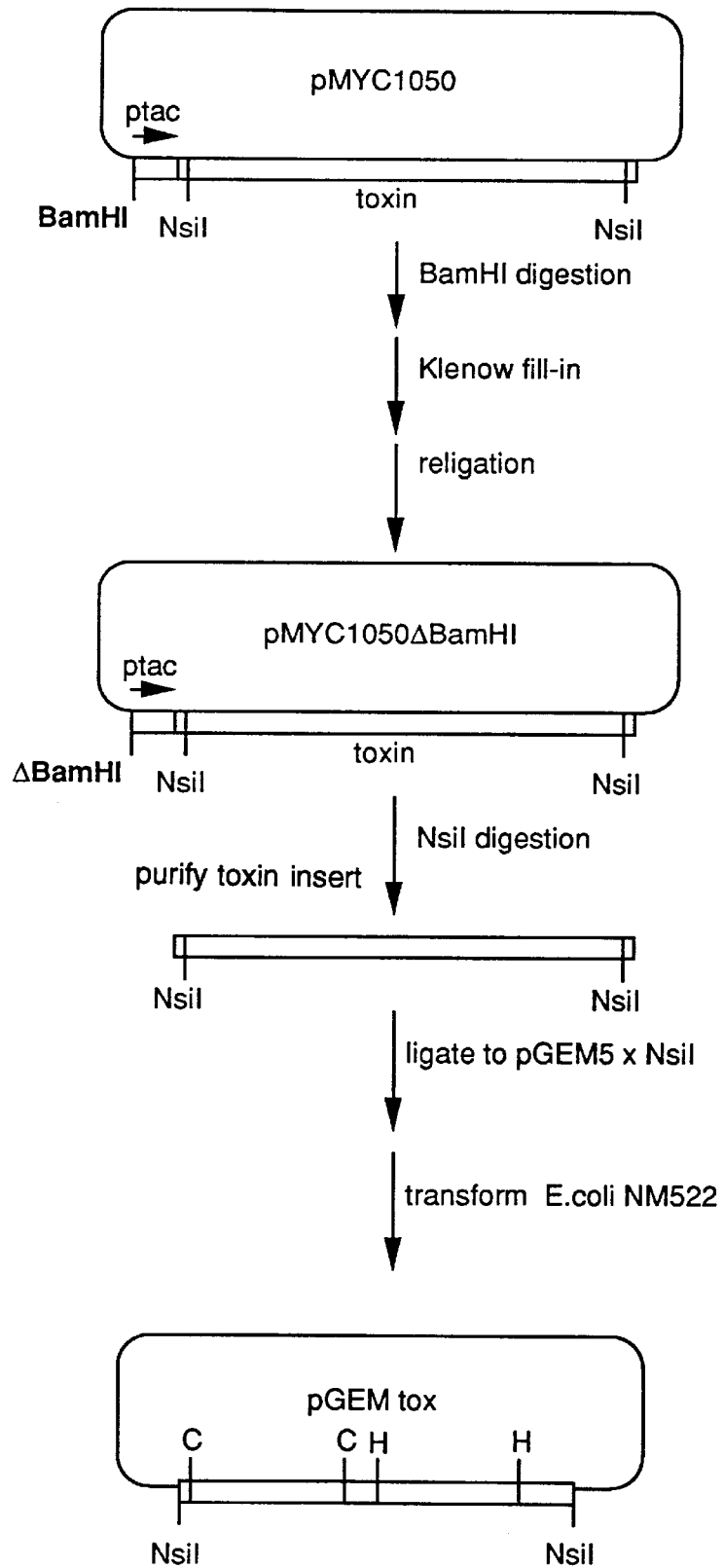
FIG. 1 The BamHI site is removed from pMYC1050 by a fill-in reaction with Klenow polymerase to give plasmid pMYC1050ΔBamHI. To facilitate cloning, an NsiI DNA fragment that contains most of the toxin open reading frame is cloned into pGEM5. The resulting plasmid is called pGEMtox. C=ClaI, H=HindIII.

SEQ ID NO. 1 is oligonucleotide primer "A"
SEQ ID NO. 2 is oligonucleotide primer "B"
SEQ ID NO. 3 is oligonucleotide primer "C"
SEQ ID NO. 4 is oligonucleotide primer "D"
SEQ ID NO. 5 is oligonucleotide primer "E"
SEQ ID NO. 6 is oligonucleotide primer "F"
SEQ ID NO. 7 is oligonucleotide primer "G"
SEQ ID NO. 8 is oligonucleotide primer "L"
SEQ ID NO. 9 is oligonucleotide primer "N"
SEQ ID NO. 10 is oligonucleotide primer "O"

SEQ ID NO. 11 is oligonucleotide primer "H"
SEQ ID NO. 12 is oligonucleotide primer "I"
SEQ ID NO. 13 is oligonucleotide primer "J"
SEQ ID NO. 14 is oligonucleotide primer "K"
SEQ ID NO. 15 is oligonucleotide primer "P"
SEQ ID NO. 16 is oligonucleotide primer "Q"
SEQ ID NO. 17 is oligonucleotide primer "M"
SEQ ID NO. 18 shows the toxin-encoding DNA sequence of pMYC2224.
SEQ ID NO. 19 shows the predicted amino acid sequence of the toxin encoded by pMYC2224.
SEQ ID NO. 20 shows the toxin-encoding DNA sequence of pMYC2239.
SEQ ID NO. 21 shows the predicted amino acid sequence of the toxin encoded by pMYC2239.
SEQ ID NO. 22 shows the toxin-encoding DNA sequence of pMYC2244, which encodes a cryIF/cryIA(b) chimeric toxin.
SEQ ID NO. 23 shows the predicted amino acid sequence of the cryIF/cryIA(b) chimeric toxin encoded by pMYC2244.
SEQ ID NO. 24 shows the toxin-encoding DNA sequence of pMYC2243.
SEQ ID NO. 25 shows the predicted amino acid sequence of the toxin encoded by pMYC2243.
SEQ ID NO. 26 shows the toxin-encoding DNA sequence of pMYC2523, which encodes a cryIF/cryIA(b) chimeric toxin with codon rework.
SEQ ID NO. 27 shows the predicted amino acid sequence of the toxin encoded by pMYC2523.
SEQ ID NO. 28 shows the toxin-encoding DNA sequence of pMYC2254, which encodes a cryIF/436 chimeric toxin.
SEQ ID NO. 29 shows the predicted amino acid sequence of the toxin encoded by pMYC2254.
SEQ ID NO. 30 is a characteristic sequence of cryI toxins. This sequence ends at residue 601 of SEQ ID NO. 23.
SEQ ID NO. 31 is the eight amino acids preceding amino acid 1043 in SEQ ID NO. 23.
SEQ ID NO. 32 shows the amino acid sequence of a native cryIF/cryIA(b) toxin.
SEQ ID NO. 33 shows the amino acid sequence of a native cryIA(b) toxin.
SEQ ID NO. 34 shows the amino acid sequence of a cryIA(c)/cryIA(b) toxin.
SEQ ID NO. 35 shows the amino acid sequence of a CryIF/CryIA(b) chimeric toxin of the subject invention that corresponds to the "Cons" sequence shown in FIG. 9.
SEQ ID NO. 36 shows the amino acid sequence of a chimeric toxin of the subject invention that incorporates the alternative amino acids as shown in the first "Alt" sequence listed above the "Cons" sequence shown in FIG. 9.
SEQ ID NO. 37 shows the amino acid sequence of a chimeric toxin of the subject invention that incorporates the alternative amino acids as shown in the second "Alt" sequence listed above the first "Alt" sequence show in FIG. 9.
SEQ ID NO. 38 shows the amino acid sequence of a chimeric toxin of the subject invention that incorporates the alternative amino acids as shown in the third "Alt" sequence listed above the second "Alt" sequence show in FIG. 9.

DETAILED DISCLOSURE OF THE INVENTION

The subject invention concerns the unexpected enhanced pesticidal activity resulting from the combination of a CryIF chimeric toxin and a CryIA(c) chimeric toxin. The combination surprisingly has increased activity against lepidopteran pests. Preparations of combinations of isolates that produce the two chimeric toxins can be used to practice the subject invention. *Pseudomonas fluorescens* cells transformed with *B.t.* genes can serve as one source of the toxins of the subject invention. For example, a lactose-inducible *P. fluorescens* strain comprising a gene encoding a CryIF/CryIA(b) toxin, and *P. fluorescens* MR436, which comprises a gene encoding a CryIA(c)/CryIA(b) chimeric toxin, can be used to practice the subject invention. These two Pseudomonas strains can be combined in a physical blend that exhibits advantageous enhanced pesticidal activity. Genes encoding the toxins of the invention can be used to transform suitable hosts so that a single host will produce the two toxins providing the advantageous effect.

Bacteria harboring plasmids useful according to the subject invention are the following:

| Culture | Repository No. | U.S. Pat. No. |
|---|---|---|
| *P. fluorescens* (pM3,130-7) | NRRL B-18332 | 5,055,294 |
| *P. fluorescens* MR436 (pM2,16-11, aka pMYC436) | NRRL B-18292 | 5,128,130 |
| *E. coli* NM522 (pMYC1603) | NRRL B-18517 | 5,188,960 |

It should be understood that the availability of a deposit does not constitute a license to practice the subject invention in derogation of patent rights granted by governmental action.

In accordance with the subject invention, it has been discovered that products comprising the two chimeric toxins have been discovered to require a lower total protein content for product application, thus providing the user greater economy. Insects which are less susceptible to the action of a single toxin will be more greatly affected by the combination of toxins of the subject invention, rendering a product containing the two toxins more efficacious than products containing a single toxin. Additionally, pests are less likely to develop a rapid resistance to a product containing the two toxins, than to products containing a single toxin.

Combinations of the toxins described in the invention can be used to control lepidopteran pests. Adult lepidopterans, i.e., butterflies and moths, primarily feed on flower nectar and are a significant effector of pollination. The larvae, i.e., caterpillars, nearly all feed on plants, and many are serious pests. Caterpillars feed on or inside foliage or on the roots or stem of a plant, depriving the plant of nutrients and often destroying the plant's physical support structure. Additionally, caterpillars feed on fruit, fabrics, and stored grains and flours, ruining these products for sale or severely diminishing their value. As used herein, reference to lepidopteran pests refers to various life stages of the pest, including larval stages.

The chimeric toxins of the subject invention comprise a full core N-terminal toxin portion of a *B.t.* toxin and, at some point past the end of the toxin portion, the protein has a transition to a heterologous protoxin sequence. The N-terminal toxin portion of a *B.t.* toxin is refererred to herein as the "core" toxin. The transition to the heterologous protoxin segment can occur at approximately the toxin/protoxin junction or, in the alternative, a portion of the native protoxin (extending past the toxin portion) can be retained with the transition to the heterologous protoxin occurring downstream. As an example, one chimeric toxin of the subject invention has the full toxin portion of cryIF (amino acids 1–601) and a heterologous protoxin (amino acids 602 to the C-terminus). In a preferred embodiment, the heterologous portion of the protoxin is derived from a cryIA(b) or 436 toxin.

A person skilled in this art will appreciate that *B.t.* toxins, even within a certain class such as cryIF, will vary to some extent in length and the precise location of the transition from toxin portion to protoxin portion. Typically, the cryIA(b) and cryIF toxins are about 1150 to about 1200 amino acids in length. The transition from toxin portion to protoxin portion will typically occur at between about 50% to about 60% of the full length toxin. The chimeric toxin of the subject invention will include the full expanse of this core N-terminal toxin portion. Thus, the chimeric toxin will comprise at least about 50% of the full length cryIF *B.t.* toxin. This will typically be at least about 590 amino acids. With regard to the protoxin portion, the full expanse of the cryIA(b) protoxin portion extends from the end of the toxin portion to the C-terminus of the molecule. It is the last about 100 to 150 amino acids of this portion which are most critical to include in the chimeric toxin of the subject invention. In a chimeric toxin specifically exemplified herein, at least amino acids 1043 (of SEQ ID NO. 23) to the C-terminus of the cryIA(b) molecule are utilized. Amino acid 1043 in SEQ ID NO. 23 is preceded by the sequence Tyr Pro Asn Asn Thr Val Thr Cys (SEQ ID NO. 31). This amino acid sequence marks the location in the protoxin segment of the molecule beyond which heterologous amino acids will always occur in the chimeric toxin. In another example, the peptide shown as SEQ ID NO. 31 occurs at amino acids 1061 to 1068. In this case, amino acids 1069 to the C-terminus are preferably heterologous (SEQ ID NO. 29). The peptide shown in SEQ ID NO. 31 can be found at positions 1061 to 1068 in FIG. 9. Thus, it is at least the last approximately 5 to 10% of the overall *B.t.* protein which should comprise heterologous DNA (compared to the cryIF core N-terminal toxin portion) in the chimeric toxin of the subject invention. In the specific examples contained herein, heterologous protoxin sequences occur from amino acid 640 to the C-terminus.

Thus, a preferred embodiment of the subject invention is a chimeric *B.t.* toxin of about 1150 to about 1200 amino acids in length, wherein the chimeric toxin comprises a cryIF core N-terminal toxin portion of at least about 50 to 60% of a full cryIF molecule, but no more than about 90 to 95% of the full molecule. The chimeric toxin further comprises a cryIA(b) or a 436 protoxin C-terminal portion which comprises at least about 5 to 10% of the cryIA(b) or 436 molecule. The transition from cryIF to cryIA(b) or 436 sequence thus occurs within the protoxin segment (or at the junction of the toxin and protoxin segments) between about 50% and about 95% of the way through the molecule. In the specific examples provided herein, the transitions from the cryIF sequence to the heterologous protoxin sequences occur prior to the end of the peptide sequence shown in SEQ ID NO. 31.

A specific embodiment of the subject invention is the chimeric toxin shown in FIG. 9. Other constructs may be made and used by those skilled in this art having the benefit of the teachings provided herein. The core toxin segment of cryI proteins characteristically ends with the sequence: Val/Leu Tyr/Ile Ile Asp Arg/Lys Ile/Phe Glu Ile/Phe/Leu Ile/Leu/Val Pro/Leu Ala/Val Glu/Thr/Asp (SEQ ID NO. 30), which ends at residue 601 of SEQ ID NO. 23. Additionally, the protoxin segments of the cryI toxins (which follow residue 601) bear more sequence similarity than the toxin segments. Because of this sequence similarity, the transition point in the protoxin segment for making a chimeric protein between the cryIF sequence and the cryIA(b) or 436 sequence can be readily determined by one skilled in the art. From studies of data regarding the partial proteolysis of CryI genes, the heterogeneity and least-conserved amino acid regions are found after the conserved cryI protoxin sequence, positions 1061–1068 of FIG. 9.

Therefore a chimeric toxin of the subject invention can comprise the full cryIF toxin and a portion of the cryIF protoxin, transitioning to the corresponding cryIA(b) or 436 sequence at any position between the end of the toxin segment (as defined above) and the end of the peptide sequence shown in SEQ ID NO. 31. Preferably, the amino acid sequence of the C-terminus of the chimeric toxin comprises a cryIA(b) sequence or a sequence from the 436 gene or an equivalent of one of these sequences.

CryIF toxins, and genes which encode these toxins, are well known in the art. CryIF genes and toxins have been described in, for example, Chambers et al. (1991) *J. Bacteriol.* 173:3966. CryIA(b) genes and toxins have been described in, for example, Höfte et al. (1986) *Eur. J. Biochem.* 161:273; Geiser et al. (1986) *Gene* 48:109; and Haider et al. (1988) *Nucleic Acids Res.* 16:10927. The skilled artisan having the benefit of the teachings contained herein could readily identify and use DNA which encodes the toxin N-terminal portion of a cryIF molecule and the C-terminal protoxin portion of the cryIA(b) toxins.

FIG. 9 provides examples of amino acid substitutions which can be used in the toxins of the subject invention. SEQ ID NO. 35 shows the amino acid sequence of a CryIF/CryIA(b) chimeric toxin of the subject invention that corresponds to the "Cons" sequence shown in FIG. 9. SEQ ID NO. 36 shows the amino acid sequence of a chimeric toxin of the subject invention that incorporates the alternative amino acids as shown in the first "Alt" sequence listed above the "Cons" sequence shown in FIG. 9. SEQ ID NO. 37 shows the amino acid sequence of a chimeric toxin of the subject invention that incorporates the alternative amino acids as shown in the second "Alt" sequence listed above the first "Alt" sequence shown in FIG. 9. SEQ ID NO. 38 shows the amino acid sequence of a chimeric toxin of the subject invention that incorporates the alternative amino acids as shown in the third "Alt" sequence listed above the second "Alt" sequence shown in FIG. 9. It is also well known in the art that various mutations can be made in a toxin sequence without changing the activity of a toxin. Furthermore, due to the degeneracy of the genetic code, a variety of DNA sequences can be used to encode a particular toxin. These alternative DNA and amino acid sequences can be used according to the subject invention by a person skilled in this art.

The protoxin substitution techniques of the subject invention can be used with other classes of *B.t.* endotoxins to enhance expression of the toxin. The technique would be most applicable to other *B.t.* toxins which have the characteristic sequence shown in SEQ ID NO. 30.

The flow charts of FIGS. 1–8 provide a general overview of vector construction that can be carried out according to the subject invention. BamHI and PvuI cloning sites can be introduced into a cryIA(c)/cryIA(b) chimeric toxin gene by mutagenesis using the PCR technique of Splice Overlap Extension (SOE) (Horton, R. M., H. D. Hunt, S. N. Ho, J. K. Pullen, L. R. Pease [1989] *Gene* 77:61–68) to give plasmid pMYC2224. A region of the cryIF gene from a cryIF-containing plasmid such as pMYC1260 can be generated by PCR and substituted for the BamHI-PvuI cryIA (c)/cryIA(b) gene fragment of pMYC2224. The new plasmid, which we designated pMYC2239, consisted of a short segment of cryIA(c) followed by cryIF to the toxin/protoxin segment junction. Thus, the protoxin segment was now derived from cryIA(b) (pMYC1050). An ApaI fragment derived from the cryIF clone (pMYC2047) was substituted for the ApaI fragment in pMYC2239. The resulting clone (pMYC2244) consisted of cryIF from the initiator methionine to the toxin/protoxin segment junction and cryIA(b) to the end of the coding region. Clone pMYC2243 was constructed by SOE to introduce silent codon changes in a limited region. The ApaI fragment from pMYC2243 that contained the silent changes was substituted for the ApaI fragment in pMYC2244 to give clone pMYC2523. The chimeric pMYC2523 showed an expression improvement over pMYC2243, which contains unchanged cryIF protein sequence.

A cryIF/436 chimera can be assembled by substituting the PvuI-BstEII protein segment-containing fragment of pMYC2523 with an equivalent fragment generated by PCR from a plasmid containing a cryIA(c)/cryIA(b) gene. One such gene is the 436 gene (e.g., pMYC467, as disclosed in U.S. Pat. Nos. 5,055,294 and 5,169,760). This construction also results in improved expression compared to the native cryIF protein sequence.

Genes and toxins. The genes and toxins useful according to the subject invention include not only the full length sequences disclosed but also fragments of these sequences, variants, mutants, and fusion proteins which retain the characteristic pesticidal activity of the toxins specifically exemplified herein. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the claimed toxins.

It should be apparent to a person skilled in this art that genes encoding active toxins can be identified and obtained through several means. The specific genes or gene portions exemplified herein may be obtained from the isolates deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

Fragments and equivalents which retain the pesticidal activity of the exemplified toxins would be within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments retaining pesticidal activity are also included in this definition.

A further method for identifying the toxins and gene portions useful according to the subject invention is through the use of oligonucleotide probes. These probes are detectable nucleotide sequences. These sequences may be detectable by virtue of an appropriate label or may be made inherently fluorescent as described in International Application No. WO93/16094. As is well known in the art, if the probe molecule and nucleic acid sample hybridize by forming a strong bond between the two molecules, it can be reasonably assumed that the probe and sample have substantial homology. Preferably, hybridization is conducted under stringent conditions by techniques well-known in the art, as described, for example, in Keller, G. H., M. M. Manak (1987) DNA Probes, Stockton Press, New York, N.Y., pp. 169–170. Detection of the probe provides a means for determining in a known manner whether hybridization has occurred. Such a probe analysis provides a rapid method for identifying toxin-encoding genes of the subject invention. The nucleotide segments which are used as probes according to the invention can be synthesized using DNA synthesizer and standard procedures. These nucleotide sequences can also be used as PCR primers to amplify genes of the subject invention.

Certain toxins of the subject invention have been specifically exemplified herein. Since these toxins are merely exemplary of the toxins of the subject invention, it should be readily apparent that the subject invention comprises variant or equivalent toxins (and nucleotide sequences coding for equivalent toxins) having the same or similar pesticidal activity of the exemplified toxin. Equivalent toxins will have amino acid homology with an exemplified toxin. This amino acid homology will typically be greater than 75%, preferably be greater than 90%, and most preferably be greater than 95%. The amino acid homology will be highest in critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 1 provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

Recombinant hosts. The genes encoding the toxins of the subject invention can be introduced into a wide variety of microbial or plant hosts. Expression of the toxin gene results, directly or indirectly, in the intracellular production and maintenance of the pesticide. Conjugal transfer and recombinant transfer can be used to create a B.t. strain that expresses both toxins of the subject invention. Other host organisms may also be transformed with one or both of the toxin genes then used to accomplish the synergistic effect. With suitable microbial hosts, e.g., Pseudomonas, the microbes can be applied to the situs of the pest, where they will proliferate and be ingested. The result is control of the pest. Alternatively, the microbe hosting the toxin gene can be treated under conditions that prolong the activity of the toxin and stabilize the cell. The treated cell, which retains the toxic activity, then can be applied to the environment of the target pest.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobactenum, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobactenium tumefaciens, Rhodopseudomonas spheroides, Xanthomonas campestris, Rhizobium melioti, Alcaligenes entrophus,* and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans*. Of particular interest are the pigmented microorganisms.

A wide variety of ways are available for introducing a B.t. gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Treatment of cells. Bacillus thuringiensis or recombinant cells expressing the B.t. toxins can be treated to prolong the toxin activity and stabilize the cell. The pesticide microcapsule that is formed comprises the B.t. toxin or toxins within a cellular structure that has been stabilized and will protect the toxin when the microcapsule is applied to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the B.t. toxin gene or genes, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as glutaraldehyde; anti-infectives, such as zephiran chloride and cetylpyridinium chloride; alcohols, such as isopropyl and ethanol; various histologic fixatives, such as Lugol iodine, Bouin's fixative, various acids and Helly's fixative (See: Humason, Gretchen L., *Animal Tissue Techniques*, W. H. Freeman and Company, 1967); or a combination of physical (heat) and chemical agents that preserve and prolong the activity of the toxin produced in the cell when the cell is administered to the host environment. Examples of physical means are short wavelength radiation such as gamma-radiation and X-radiation, freezing, UV irradiation, lyophilization, and the like. Methods for treatment of microbial cells are disclosed in U.S. Pat. Nos. 4,695,455 and 4,695,462, which are incorporated herein by reference.

The cells generally will have enhanced structural stability which will enhance resistance to environmental conditions. Where the pesticide is in a proform, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of treatment should retain at least a substantial portion of the bio-availability or bioactivity of the toxin.

Characteristics of particular interest in selecting a host cell for purposes of production include ease of introducing the B.t. gene or genes into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Growth of cells. The cellular host containing the B.t. insecticidal gene or genes may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells producing the toxins of the invention can be cultured using standard art media and fermentation techniques. Upon completion of the fermentation cycle the bacteria can be harvested by first separating the B.t. spores and crystals from the fermentation broth by means well known in the art. The recovered B.t. spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art.

Formulations. Formulated bait granules containing an attractant and spores, crystals, and toxins of the B.t. isolates, or recombinant microbes comprising the genes obtainable from the B.t. isolates disclosed herein, can be applied to the soil. Formulated product can also be applied as a seed-coating or root treatment or total plant treatment at later stages of the crop cycle. Plant and soil treatments of B.t. cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the lepidopteran pest, e.g., foliage or soil, by spraying, dusting, sprinkling, or the like.

Materials and Methods

NACS (Bethesda Research Labs, Gaithersburg, Md.) column chromatography was used for purification of electro-eluted DNA. It was performed according to the manufacturer's directions, except that the buffers were modified to 0.5× TBE/0.2M NaCl for binding, and 0.5× TBE/2.0M NaCl for elution.

Random priming labeling of DNA with $\alpha$-[$^{32}$P]dATP was done with a kit (Boehringer-Mannheim Biochemicals, Indianapolis, Ind.) according to the manufacturer's directions.

Gel purification refers to sequential application of agarose-TBE gel electrophoresis, electroelution, and NACS column chromatography for purification of selected DNA fragments, methods which are well known in the art.

Polymerase chain reaction (PCR) amplification of DNA was done for 25 cycles on a Perkin Elmer (Norwalk, Conn.) thermal cycler with the following cycle parameters: 94° C. for 1 minute, 37° C. for 2 minutes, 72° C. for 3 minutes (each 72° C. cycle has a 5 second extension time). PCR DNA products were proteinase K treated to improve cloning efficiency (Crowe, J. S., Cooper, H. J., Smith, M. A., Sims, M. J., Parker, D., Gewert, D. [1991] Nucl. Acids Res. 19:184).

Oligodeoxyribonucleotides (oligonucleotides) were synthesized on an Applied Biosystems (Foster City, Calif.) model 381A DNA synthesizer. Purification was done with Nensorb columns (New England Nuclear-Dupont, Wilmington, Del.), if necessary, according to the manufacturer's instructions.

Electroporation of Pseudomonas fluorescens was done with log-phase cells grown in L-broth (LB) at 30° C. on a rotary shaker. Cells were washed 2 to 3 times with ice-cold sterile distilled water and concentrated to 0.03× starting volume in distilled water. DNA in 1–20 $\mu$l was mixed with 50–300 $\mu$l of cells. Parameters selected for the Biorad Gene Pulser (Bio-Rad, Richmond, Calif.) were 200 ohms, 25 microfarads, and 2.25 kilovolts in a cuvette with a 0.2 cm electrode gap. Following electroporation, one milliliter of LB was added and cells were held on ice for at least 2 minutes. Cells were then incubated for 2 hours to overnight at 30° C. without shaking.

B.t. toxin expression in P. fluorescens was done in the recommended medium found in the Manual of Methods for General Bacteriology (P. Gerhardt et al., 1981, American Society for Microbiology, Washington, D.C.). Glycerol was substituted for glucose. The recipe was made with tap water and the pH adjusted to 7.2. Seed flasks were made from L-broth. The following recipes apply:

| Base Medium (for 1 liter) | |
| --- | --- |
| glycerol | 65 g |
| $(NH_4)_2SO_4$ | 1.0 g |
| $Na_2HPO_4$ | 5.24 g |
| $KH_2PO_4$ | 2.77 g |
| Yeast extract | 5.0 g |
| Casamino acids | 1.0 g |
| Metals 44 (for 100 ml) | |
| EDTA | 250 mg |
| $ZnSO_4.7H_2O$ | 1095 mg |
| $FeSO_4.7H_2O$ | 500 mg |
| $MnSO_4.H_2O$ | 154 mg |
| $CuSO_4.5H_2O$ | 39.2 mg |
| $Co(NO_3)_2.6H_2O$ | 24.8 mg |
| $Na_2B_4O_7.10H_2O$ | 17.7 mg |
| Add a few drops of 6 N $H_2SO_4$ to retard precipitation. | |
| Huntner's Mineral Mix (for 1 liter) | |
| Nitriloacetic acid (dissolved and neutralized with KOH) | 10 g |
| $MgSO_4.7H_2O$ | 14.45 g |
| $CaCl_2.2H_2O$ | 3.33 g |
| $(NH_4)_6Mo_7O_{24}.4H_2O$ | 9.25 g |
| $FeSO_4.7H_2O$ | 99 mg |
| Metals 44 | 50 ml |
| pH adjusted to 6.6–6.8 | |

At inoculation for analysis of B.t. toxin expression, 4 ml of Huntner's Mineral Mix was added per 200 ml of broth. Flasks were then given a 2% inoculum, by volume, of an overnight culture. Cultures were allowed to grow for 24 hours at 32° C. at ≧200 rpm. At this point, they were induced with 0.75 mM IPTG and supplemented with 2 g yeast extract. Protein gels were run on samples pulled at 48 and 72 hours. The 130 kDa protein was quantified by laser densitometry.

Following are examples which illustrate procedures, including the best mode, for practicing the invention. These examples should not be construed as limiting. All percentages are by weight and all solvent mixture proportions are by volume unless otherwise noted.

EXAMPLE 1
Expression Vector Modification by Splice Overlap Extension (SOE)

A cloning vector can be constructed based on pTJS260, a broad host-range plasmid derived from RSF1010 (pTJS260 can be obtained from Dr. Donald Helinski, U.C. San Diego). An example of the system used in the vector construction can be found in EPO patent application 0 471 564. A cryIA(c)/cryIA(b) gene, referred to herein as the 436 gene and toxin, are described in U.S. Pat. No. 5,055,294. A plasmid designated pMYC1050 contains the 436 gene. pMYC1050 was constructed by re-cloning the toxin gene and promoter of pM3,130-7 (disclosed in U.S. Pat. No. 5,055,294) into a pTJS260-based vector such as pMYC467 (disclosed in U.S. Pat. No. 5,169,760) by methods well known in the art. In particular, the pM3,130-7 promoter and toxin gene can be obtained as a BamHI to NdeI fragment and placed into the pMYC467 plasmid replacing a fragment bounded by the same sites (BamHI near base 12100 and NdeI near base 8000).

The improved vector ideally contains a unique BamHI cloning site. The plasmid BamHI site, located upstream from the tac promoter (Ptac), can be removed by blunting with Klenow and religating (FIG. 1). Absence of the site can be confirmed by restriction digestion. A plasmid produced according to this procedure was called pMYC1050ΔBamHI. The construct can now have a BamHI site added to the plasmid by SOE mutagenesis. SOE mutagenesis can be facilitated by subcloning an NsiI toxin-containing DNA fragment into the smaller pGEM5 (Promega Corp., Madison, Wis.) vector which uses the ampicillin resistance (bla) gene as a selectable marker (FIG. 1). The fragment can be oriented by restriction digestion. A plasmid produced according to this procedure was called pGEMtox.

Figure 2:
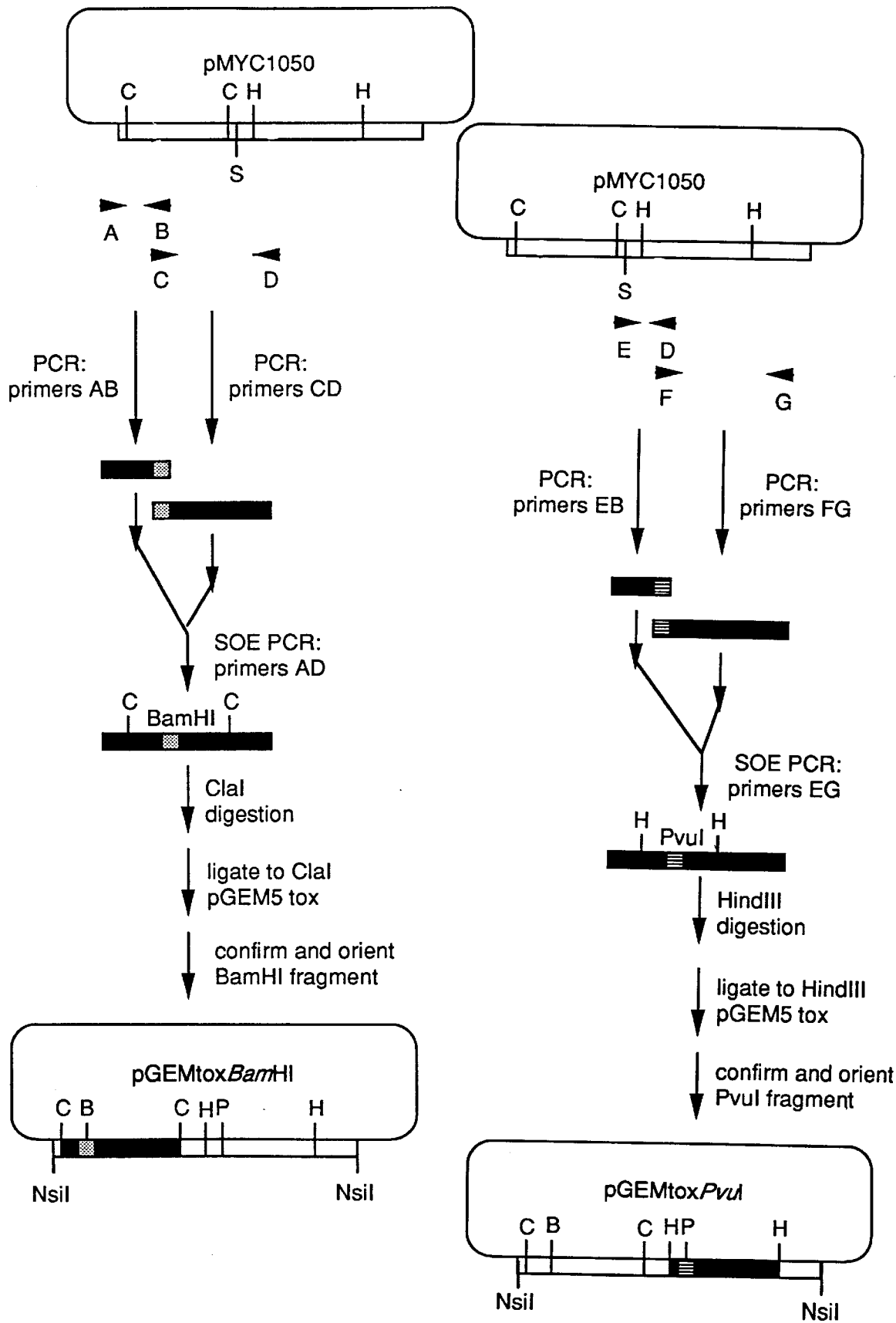
FIG. 2 BamHI or PvuI cloning sites were introduced into toxin DNA by the technique of Splice Overlap Extension (SOE). DNA fragments with the new sites are used to replace homologous DNA fragments in pGEMtox. The resulting plasmids are pGEMtoxBamHI or pGEMtoxPvuI. The letters A through G below the arrows correspond to oligonucleotide primers in the text. Letters above vertical lines correspond to restriction enzyme sites. B=BamHI, C=ClaI, H=HindIII, P=PvuI, S=SacI.
Figure 4:
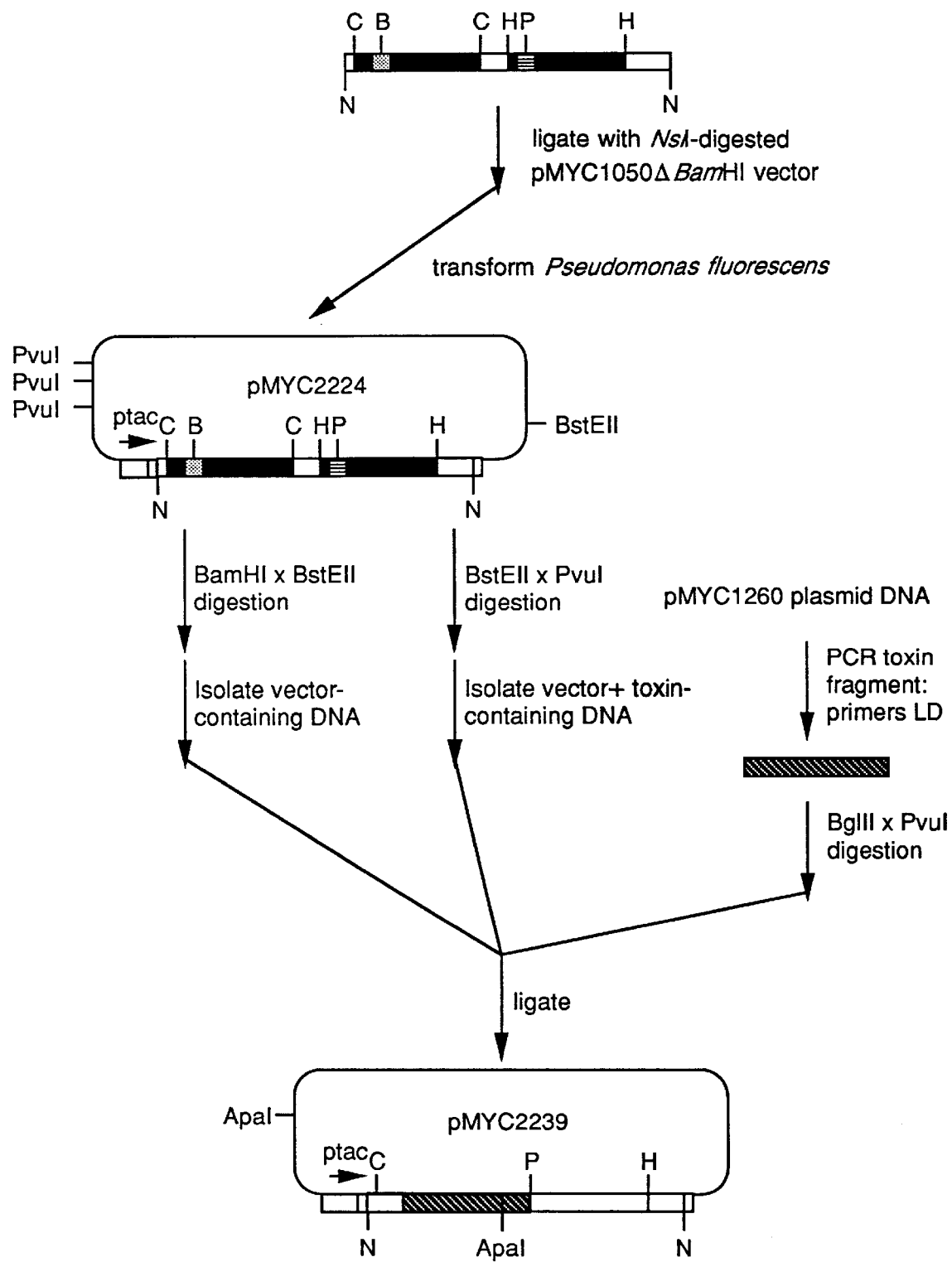
FIG. 4 The NsiI toxin-containing fragment with the new restriction sites is ligated to the vector-containing DNA from pMYC1050ΔBamHI to give pMYC2244. A BamHI-PvuI PCR-derived DNA fragment containing the cryIF toxin is exchanged for the equivalent fragment in pMYC2244. The resulting chimera is called pMYC2239. B=BamHI, C=ClaI, H=HindIII, N=NsiI, P=PvuI.

DNA in the toxin coding region can be mutated by the PCR-mediated technique of SOE to introduce restriction enzyme cloning sites as shown in FIG. 2. Oligonucleotides useful as primers are shown below:

"A" (SEQ ID NO. 1)
5' GCATACTAGTAGGAGATTTCCATGGATAACAATCCGAAC 3'
"B" (SEQ ID NO. 2)
5' GGATCCGCTTCCCAGTCT 3'
"C" (SEQ ID NO. 3)
5' AGAGAGTGGGAAGCGGATCCTACTAATCC 3'
"D" (SEQ ID NO. 4)
5' TGGATACTCGATCGATATGATAATCCGT3'

"E" (SEQ ID NO. 5)

5' TAATAAGAGCTCCTATGT 3'

"F" (SEQ ID NO. 6)

5' TATCATATCGATCGAGTATCCAATTTAG 3'

"G" (SEQ ID NO. 7)

5' GTCACATAGCCAGCTGGT 3' pMYC1050 DNA was used as the template for PCR amplification using primer sets A/B, C/D, E/D, and F/G. Amplified DNA fragments were named AB, CD, ED, and FG. Amplified DNAs were purified by agarose-TBE gel electrophoresis, electroelution, and NACS column chromatography, methods all well-known in the art. Purified template DNAs were used in a second set of PCR reactions. Fragments AB and CD were mixed and amplified with primers A and D. In a separate reaction, fragments ED and FG were mixed and amplified with primers E and G. Amplified DNA was resolved by agarose-TBE gel electrophoresis and the fragments with the corresponding increase in size were excised, electroeluted, and purified over NACS columns by means well known in the art. Amplified DNA fragments are called AD or EG for reference.

DNA fragments AD or EG with the new restriction enzyme sites were incorporated into the toxin-containing DNA by several subcloning procedures (FIGS. 2 and 3). pGEMtox was digested with ClaI or HindIII. Vector-containing DNA was gel-purified. Fragment AD was digested with ClaI and ligated to ClaI-digested pGEMtox vector DNA. Fragment EG was digested with HindIII and ligated to HindIII-digested pGEMtox vector DNA. *E. coli* strain NM522 was transformed with ligation mixes. Correctly assembled constructs were identified by restriction enzyme digestion of plasmid DNA from isolated colonies. The plasmid with the new BamHI site was called pGEM tox BamHI. The plasmid with the new PvuI site was called pGEMtox PvuI. The ClaI fragment containing the BamHI site from plasmid pGEMtox BamHI was ligated to the phosphatased ClaI vector-containing fragment from pGEMtox PvuI. *E. coli* strain NM522 was transformed with ligation mixes. Correctly assembled constructs were identified by PCR analysis with primer set C/D, and by restriction digestion. The plasmid with both new restriction enzyme sites was called pGEMtox BamHI/PvuI.

A completed expression vector was assembled with insert from pGEMtox BamHI/PvuI and vector from pMYC1050ΔBamHI (FIGS. 3 and 4). Gel-purified insert was prepared from pGEMtox BamHI/PvuI by NsiI digestion, and ScaI digestion (to remove contaminating vector). It was ligated to gel-purified NsiI-digested vector-containing pMYC1050ΔBamHI DNA. *E. coli* strain NM522 was transformed with the ligation mixes, and transformation mixes were plated on LB agar containing tetracycline at 12 μg/ml. Colonies containing the NsiI insert were identified by colony hybridization and autoradiography. Inserts were oriented by PCR, using primer set A/D, which bridges an NsiI cloning site, and agarose-TBE gel electrophoresis. The correctly assembled plasmid is called pMYC2224. DNA and protein sequences of the toxin are found in SEQ ID NOS. 18 and 19, respectively. A lactose-inducible *P. fluorescens* strain was electroporated with correctly assembled plasmid DNA. Transformation mixes were plated on LB agar containing tetracycline at 20 μg/ml. Plasmid DNA was prepared from *P. fluorescens* for use in subsequent cloning experiments.

EXAMPLE 2

Subcloning the cryIF Hypervariable Region into pMYC2224

A DNA fragment containing the hypervariable region from cryIF (pMYC1260) was exchanged for the BamHI-PvuI toxin-containing DNA fragment from pMYC2224 (FIG. 4). Since the coding sequence contains a preexisting BamHI site, BglII was chosen for cloning. The 4-base overhangs of BamHI and BglII are compatible, permitting ligation while eliminating both sites from the junction. It was necessary to synthesize a new primer for PCR:

"L" (SEQ ID NO. 8)

5' GAGTGGGAAGCAGATCTTAATAATGCACAATTAAGG 3'

A toxin-containing DNA fragment was generated by PCR with primers L/D on template pMYC1260. The DNA was digested with BglII and PvuI for subcloning. Since the tetAR locus contains multiple PvuI sites, it was necessary to isolate the vector-containing DNA on two separate fragments. To obtain the first fragment, pMYC2224 was digested with BamHI×BstEII, and the large DNA fragment containing the Ptac-tetAR locus-rep functions was gel-purified. To obtain the second fragment, pMYC2224 was digested with BstEII×PvuI, and the DNA fragment containing the vector-protoxin module was gel-purified. A three-piece ligation was set up and used for *E. coli* strain NM522 transformation. Grossly correct plasmids were identified by PCR analysis and agarose-TBE gel electrophoresis using the primer set N/O, which bridges the BamHI/BglII fusion junction.
"N" (tac promoter) (SEQ ID NO. 9)
5' TTAATCATCGGCTCGTA 3'
"O" (SEQ ID NO. 10)
5' ACTCGATCGATATGATA(GA)TCCGT 3'

The correct plasmid was named pMYC2239. It consists of cryIA(c) at the amino-terminus, cryIF up to the toxin/protoxin junction, and cryIA(b) through the protoxin segment. The toxin DNA and protein sequences are in SEQ ID NOS. 20 and 21, respectively.

EXAMPLE 3
Construction of the *P. fluorescens* Expression Plasmids pMYC1260 and pMYC2047

The cloned toxin gene cryIF can be modified for expression in *P. fluorescens* in the following way:

1. A plasmid containing the pKK223-3 rrnB termination sequences in the pTJS260-derived vector (Dr. Donald Helinski, U.C. San Diego) can be made by ligating the BamHI-ScaI fragment containing the Ptac promoter and rrnB terminator from pKK223-3 (Pharmacia *E. coli* vector) into the BamHI to blunted KpnI vector fragment of pMYC1197 (described in EP 0 417 564). The assembled plasmid is recovered following transformation of *E. coli* and growth under tetracycline selection.

2. A plasmid containing the Ptac-promoted cryIF toxin gene can be made by ligating toxin gene-containing NdeI-Nde-I fragment (with ends blunted using DNA polymerase and dNTPs) of about 3800 bp from pMYC1603 (from NRRL B-18517) into the blunted EcoRI and HindIII sites of pKK223-3. The Ptac-promoted cryIF toxin plasmid can be recovered following transformation of *E. coli*, grown under ampicillin selection, and screening for plasmids with inserts in the proper orientation for expression from the Ptac promoter by techniques well known in the art.

3. The Ptac-promoted cryIF toxin can be assembled into the pTJS260-derived vector in a three-piece ligation using the 2.4 kb DNA fragment having BamHI and ApaI ends from the plasmid pTJS260, ApaI to HindIII fragment of 8.5 kb containing the replication region of the plasmid from step 1 above, and a HindIII to partial BamHI fragment containing the Ptac promoter and cryIF toxin gene from step 2 above.

The resulting pTJS260-derived cryIF toxin expression plasmid (pMYC1260) can be introduced into *P. fluorescens* by electroporation.

4. pMYC2047 can be constructed by ligating an SpeI to KpnI fragment obtained through PCR of a suitable cryIF template with primers H and K followed by digestion with SpeI and KpnI and gel purification, an ApaI to KpnI fragment of ca. 10 kb from the plasmid of step 3, and the ApaI to SpeI fragment of ca. 2600 bp from pMYC1197 containing the Ptac promoter. The correct cryIF toxin expression plasmids are determined by restriction enzyme digestion of plasmids following electroporation into *Pseudomonas fluorescens*.

EXAMPLE 4
Construction of a cryIF/cryIA(b) Chimera

Figure 5:
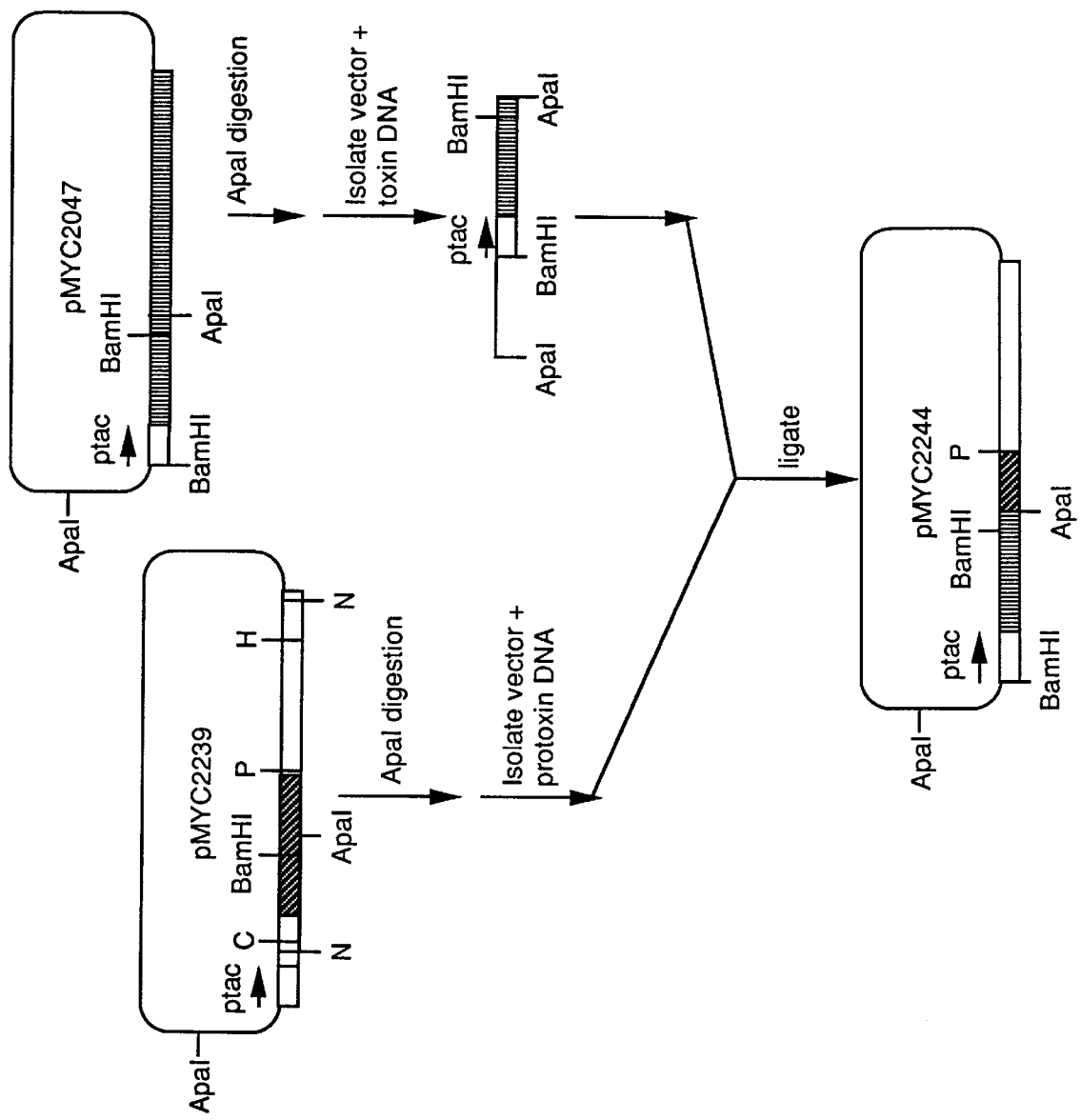
FIG. 5 The small ApaI DNA fragment of pMYC2047 is substituted for the homologous region of pMYC2239 to give plasmid pMYC2244. This chimera consists of cryIF in the toxin region and cryIA(b) in the protoxin. C=ClaI, H=HindIII, N=NsiI, P=PvuI.

The cryIA(c) segment at the amino-terminus can be replaced by the cryIF coding sequence by a simple, straightforward swap (FIG. 5). Both the tetAR locus and cryIF coding sequence contain an ApaI site. A small ApaI fragment containing a portion of the tetAR genes and the amino-terminus of cryIF can be isolated from pMYC2047 and ligated to the large ApaI vector-containing fragment from pMYC2239. A *P. fluorescens* lactose-inducible strain can be electroporated with the ligation mix and plated on LB agar containing tetracycline at 20 µg/ml. Lactose-inducible strains are known to those skilled in the art and are described, for example, in U.S. Pat. No. 5,169,760. Correct orientation of the ApaI fragment reconstitutes tetracycline resistance. A clone produced in this manner was shown to be grossly correct by restriction enzyme digestion, and it was named pMYC2244. The toxin DNA sequence is shown in SEQ ID NO. 22, and the predicted protein sequence is shown in SEQ ID NO. 23.

EXAMPLE 5
Construction of a Limited Codon Rework of cryIF

Figure 6:
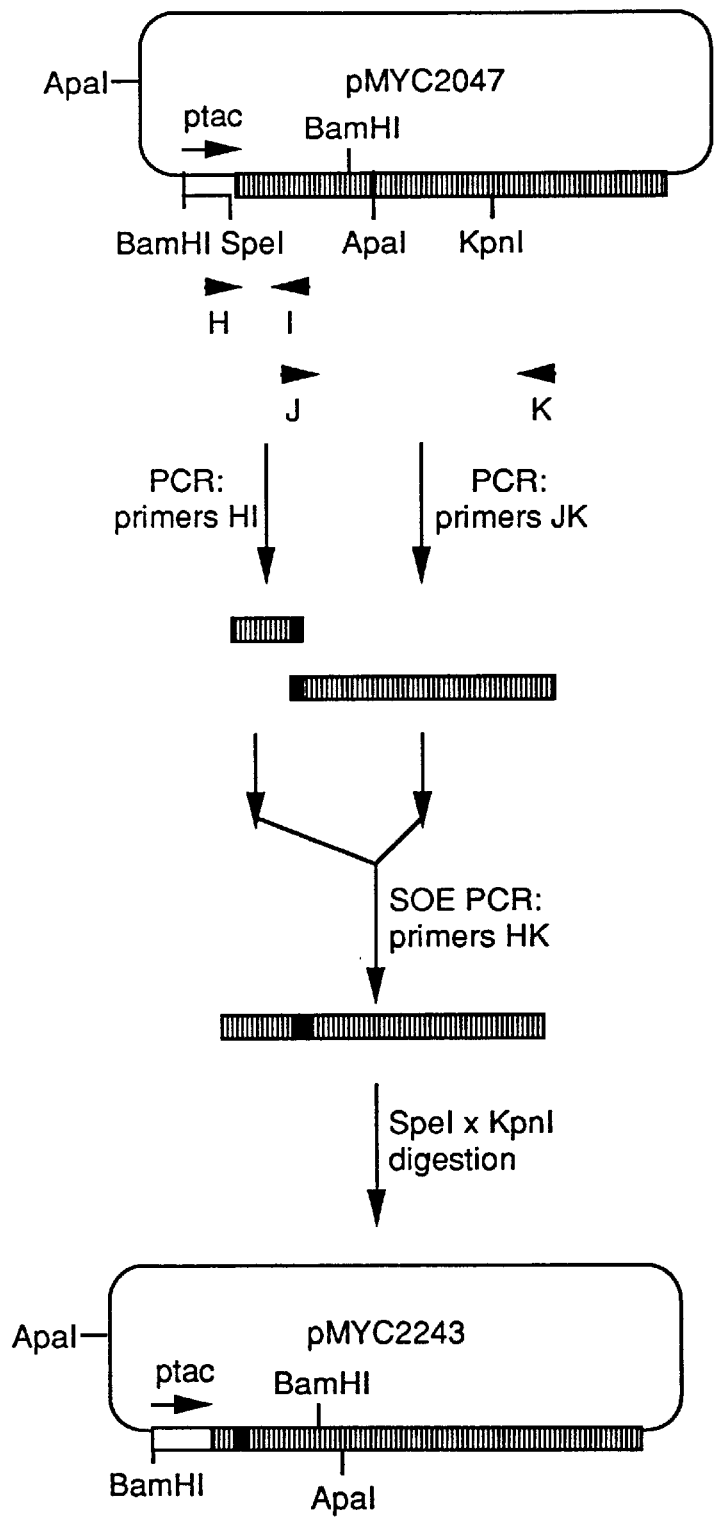
FIG. 6 Silent codon changes are introduced into the cryIF toxin by SOE. The SpeI-KpnI PCR DNA fragment with the changes is substituted for the homologous toxin-containing fragment in pMYC2047. The resulting plasmid is pMYC2243. Letters H through K below the arrows correspond to oligonucleotide primers in the text.
Figure 7:
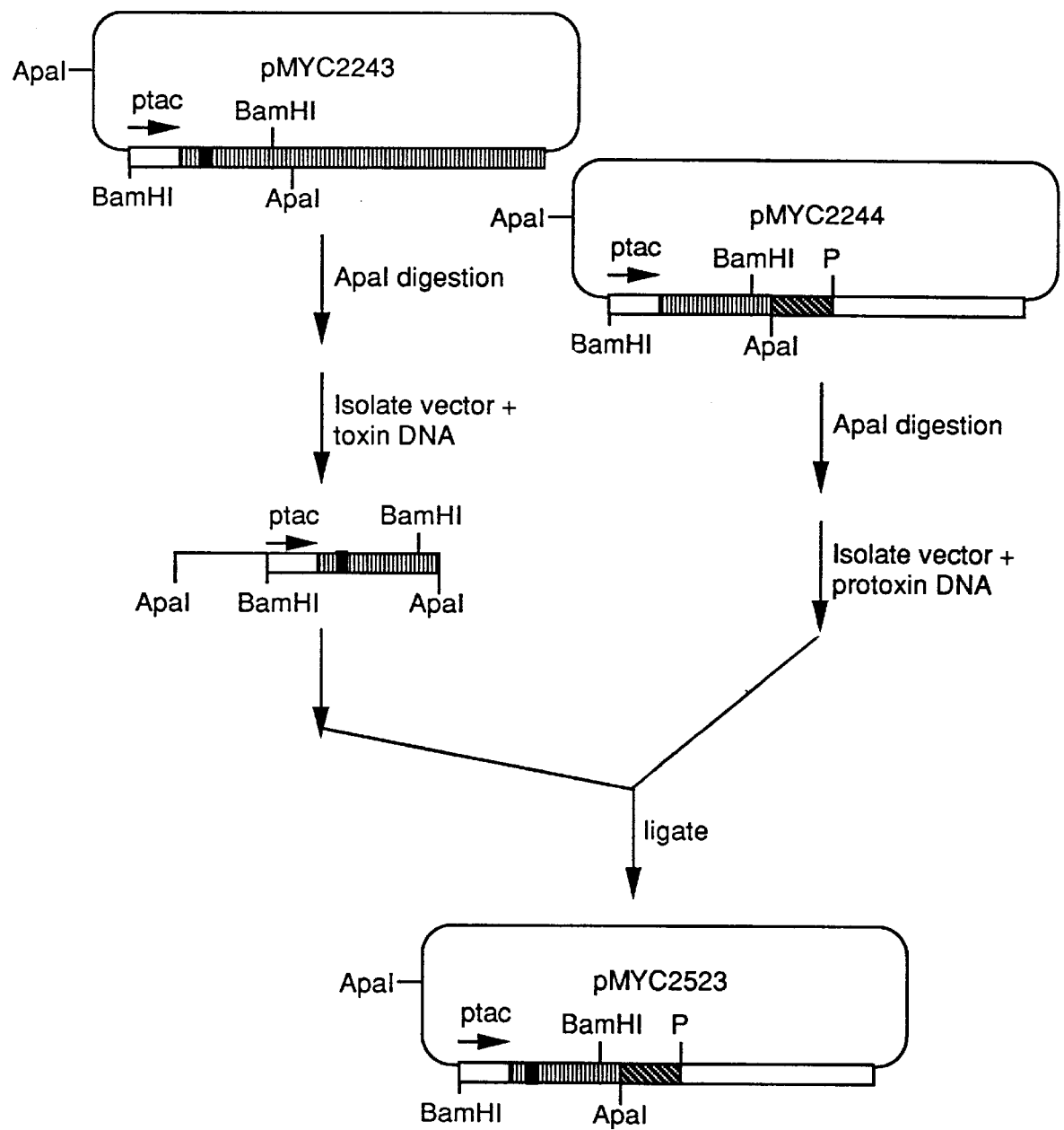
FIG. 7 Silent codon changes are introduced into pMYC2244 by substitution of the homologous fragment with the small ApaI DNA fragment of pMYC2243. The final plasmid is pMYC2523. P=PvuI.

Codon usage in Pseudomonas spp. favors G or C in the wobble position of triplet codons, as determined by analysis of genes in the GenBank/EMBL sequence libraries. A limited region of the cryIF gene was reworked by SOE to incorporate favored wobble position changes that were silent (FIG. 6). Oligos used are shown below:

"H" (SEQ ID NO. 11)
5' GGACTAGTAAAAAGGAGATAACCATGGAAAATAATATTCAAAATC 3'
"I" (SEQ ID NO. 12)
5' TCCAGCGGCAGGCGGCCGGTGCTGCGTTCTTCGTTCAGTATTTCTACT
TCAGGATTATTTAAAC 3'
"J" (SEQ ID NO. 13)
5' AACGCAGCACCGGCCGCCTGCCGCTGGACATCAGCCTGAGCCTTACAC
GTTTCCTTTTGAGTGAA 3'
"K" (SEQ ID NO. 14)
5' CATCAAAGGTACCTGGT 3'

Two separate PCR reactions were done on pMYC2047 template with primer sets H/I or J/K. Amplified DNA fragments were called HI or JK. A second PCR reaction was set up by mixing fragments HI and JK and PCR amplifying with primer set H/K. The larger SOE DNA was gel-purified and digested with SpeIxKpnI. A three-piece ligation was set up with SpeI-ApaI Ptac-tetAR locus DNA, ApaI-KpnI vector-protoxin module DNA, and SpeI-KpnI PCR DNA. A *P. fluorescens* lactose-inducible strain can be electroporated with the ligation mix. Grossly correct clones can be identified by PCR analysis using the primer set P/Q and agarose-TBE gel electrophoresis. Oligo P (SEQ ID NO. 15) was designed to discriminate between the wild-type and codon-reworked gene.

"P" (SEQ ID NO. 15)
5' TGCCGCTGGACATCAGCCTGAG 3'
"Q" (SEQ ID NO. 16)
5'        TCTAGAGCGGCCGCTTATAC(CT)
CGATCGATATGATA(GA)TCCGT 3'

The complete plasmid was named pMYC2243. The toxin DNA sequence is shown in SEQ ID NO. 24. The toxin protein sequence is predicted to be unchanged, and is shown in SEQ ID NO. 25.

EXAMPLE 6
Construction of the cryIF/crvIA(b) Chimera Containing the Limited Codon Rework The construct was assembled (FIG. 7) using the same ApaI fragment exchange strategy as for pMYC2244 (cryIF/ cryIA(b)) above. The small, toxin-tetAR locus ApaI DNA fragment was gel-purified from pMYC2243. The larger vector-protoxin module ApaI DNA fragment was gel-purified from pMYC2244. The completed plasmid was named pMYC2523. Predicted DNA and protein sequences are in SEQ ID NOS. 26 and 27, respectively.

EXAMPLE 7
Comparative Expression of Toxins from pMYC2244 and pMYC2523

Toxin expression in *P. fluorescens* was analyzed as described above. At 24 and 48 hours post-induction, the pMYC2523-containing strain produced more toxin than the pMYC2244-containing strain. Toxin specific activity on *Spodoptera exigua* was statistically unchanged.

Figure 8:
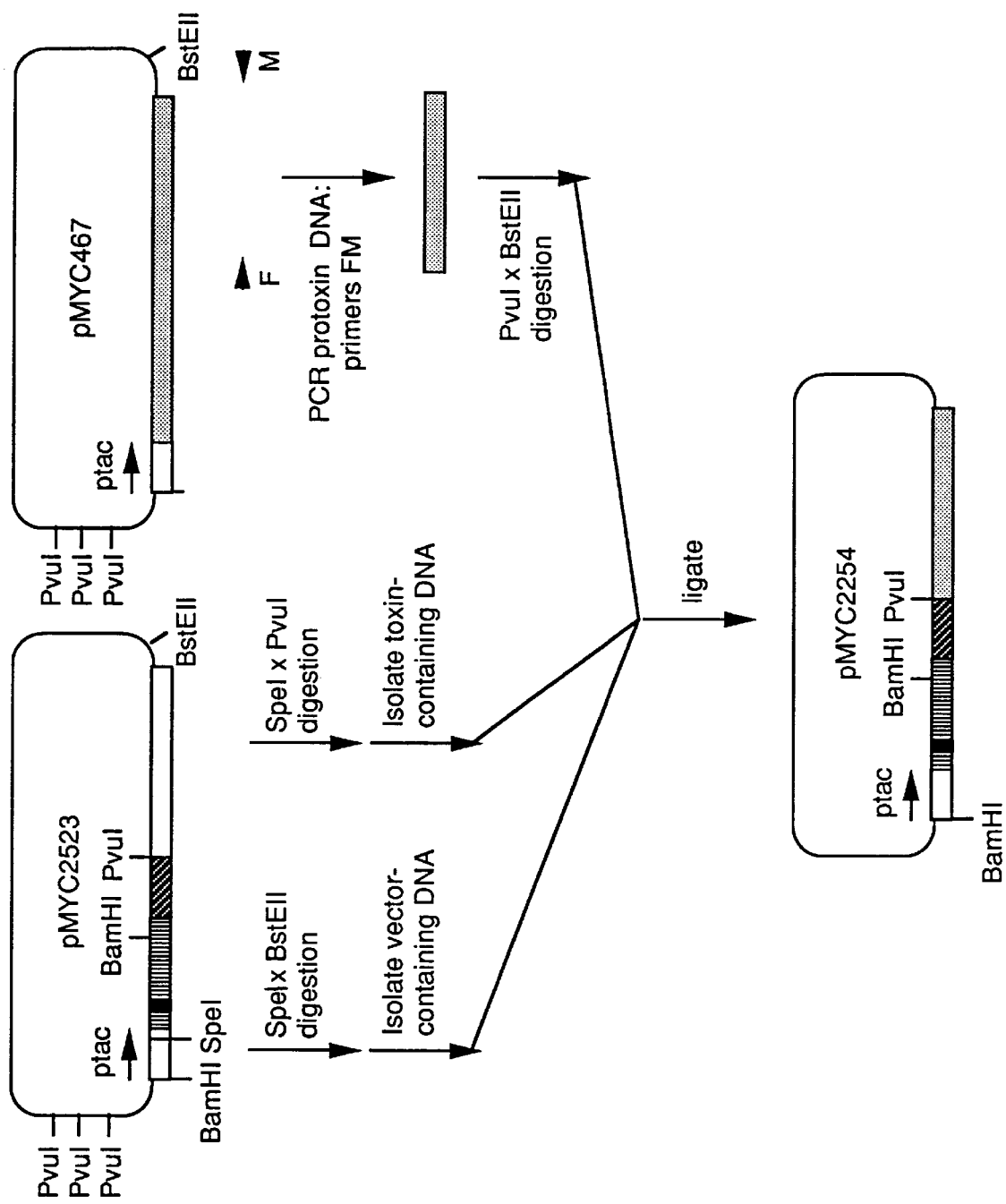
FIG. 8 A chimeric toxin containing the 436 protoxin is constructed by substituting a PCR-generated PvuI-BstEII protoxin DNA for the homologous fragment in pMYC2523. The final plasmid is pMYC2254. Letters F and M below the arrows correspond to oligonucleotide primers in the text.

EXAMPLE 8
Construction of the cryIF/436 Chimera Containing the Limited Codon Rework A second type of chimeric toxin was assembled by substituting the 436 protoxin module for the cryIA(b) protoxin in pMYC2523 (FIG. 8). The 436 protoxin sequence consists of cryIA(c) sequence except at the very C-terminus (See U.S. Pat. Nos. 5,128,130 and 5,169,760, incorporated herein by reference in their entirety). Protoxin DNA for cloning was generated by PCR with the primer set F/M using a plasmid such as pMYC467 (U.S. Pat. No. 5,169,760) as a template.

"M" (SEQ ID NO. 17)
5' AGGCTTCCATAGATACCTTGTGCG 3'

PCR DNA was digested with PvuI×BstEII. A three-piece ligation was set up with SpeI-PvuI toxin DNA from pMYC2523, SpeI-BstEII vector DNA from pMYC2523, and PvuI-BstEII PCR protoxin module DNA. A lactose-inducible *P. fluorescens* strain was electroporated with the ligation mix. Grossly correct plasmids were identified by PCR with primer set F/G and screening for slight size increase by agarose-TBE gel electrophoresis. The construct was named pMYC2254. Predicted DNA and protein sequences are found in SEQ ID NOS. 28 and 29, respectively.

EXAMPLE 9
Comparative Expression of Toxins from pMYC2243 and pMYC2254

Toxin expression in *P. fluorescens* was analyzed as described above. Toxin expression from pMYC2254 was improved over pMYC2243 expression.

EXAMPLE 10
Analysis for Synergy Between CryIF Chimeric Toxin and CryIA(c) Chimeric Toxin Against the Corn Earworm, *Heliothis zea*

Twenty-four *Heliothis zea* first instar larvae were exposed to agar diet containing various concentrations of toxin. At 7 days post treatment, assays were graded for growth inhibition. Larvae were inhibited if the molt from first to second instar was inhibited. Calculations for estimating synergy factor (SF) and expected activity (E[exp]) are shown below.

$$SF = E(obs)/E(exp)$$

where,

SF=synergy factor
E(obs)=observed mortality
E(exp)=expected mortality $$E(exp) = a + b - (ab/100)$$

where, a=activity from compound A
b=activity from compound B

TABLE 2

| | % INHIBITION | | | | |
|---|---|---|---|---|---|
| Rate | cryIF/ cryIA(b) | cryIA(c)/ cryIA(b) | 1:1 mix of the two chimeric toxins | | |
| μg toxin/g diet | a | b | E(exp) | E(obs) | SF |
| 50.0 | — | — | 50 | 78 | 1.6 |
| 25.0 | 13 | 23 | 22 | 62 | 2.8 |
| 12.5 | 9 | 14 | 22 | 31 | 1.4 |
| 6.25 | 9 | 14 | — | — | — |

An SF greater than 1 indicates synergy (Levy, Y., M. Benderly, Y. Cohen, U. Gisi, D. Bassard [1986] Bulletin OEPP/EPPO Bulletin 16:651–657).
Abbott, W. S. (1925) J. Economic Entomology 18:265–267.

EXAMPLE 11
Analysis for Synergy Between CryIF Chimeric Toxin and CryIA(c) Chimeric Toxin Against the Corn Earworm, *Heliothis zea*

Twenty-four *Heliothis zea* first instar larvae were exposed to agar diet containing various concentrations of toxin. At 7 days post treatment, assays were graded for growth inhibition. Larvae were inhibited if the molt from first to second instar was inhibited. The dosage required to inhibit 50 percent of the populations ($ED_{50}$) was estimated using standard probit analysis techniques. Calculations for estimating synergy factor (SF) and expected effective dosages (ED[exp]) are shown below.

$$SF = ED(exp)/ED(obs)$$

where,

ED(exp)=expected effective dose of a mixture
ED(obs)=observed effective dose of a mixture $$ED(exp) = (a+b)/a/ED_A + b/ED_B$$

where, a=proportion of compound A in mixture
b=proportion of compound B in mixture
$ED_A$ and $ED_B$=equally effective doses of A and B in mixture.

TABLE 3

| Treatment | | ED(obs) (μg toxin/g diet) | ED(exp) | SF |
|---|---|---|---|---|
| cryIA(c)/cryIA(b) | (A) | 36 | — | — |
| cryIF/cryIA(b) | (B) | 135 | — | — |
| A:B (1:1) | | 21 | 57 | 2.6 |
| A:B (3:1) | | 14 | 44 | 3.1 |
| A:B (1:3) | | 35 | 80 | 2.3 |

A SF greater than 1 indicates synergy (Levy et al. [1986], supra).
[CITE for Wadley method]

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A composition for controlling lepidopteran pests, wherein said composition comprises cells which express a CryIF chimeric core toxin-containing protein and a CryIA(c) chimeric core toxin-containing protein.

2. The composition, according to claim 1, comprising a cell expressing a CryIF chimeric core toxin-containing protein and a cell expressing a CryIA(c) chimeric core toxin-containing protein.

3. The composition, according to claim 1, comprising a cell expressing a CryIF chimeric core toxin-containing protein and a CryIA(c) chimeric core toxin-containing protein.

4. The composition, according to claim 1, wherein said CryIF chimeric core toxin-containing protein comprises a CryIF core N-terminal protein portion and a heterologous C-terminal toxin portion from a CryIA(b) toxin or CryIA(b)/CryIA(c) chimeric toxin.

5. The composition, according to claim 4, wherein said CryIF chimeric core toxin-containing protein has approximately 1150 to 1200 amino acids and comprises a CryIF core N-terminal sequence of at least about 590 amino acids and no more than about 1100 amino acids, wherein said CryIA(b) or CryIA(c)/CryIA(b) portion comprises at least 100 amino acids at the C-terminus of said protein.

6. The composition, according to claim 4, wherein the transition from CryIF core N-terminal toxin portion to heterologous portion occurs after the sequence shown in SEQ ID NO. 30 and before the end of the peptide sequence of SEQ ID NO. 31.

7. The composition, according to claim 6, wherein said core toxin portion comprises the first about 601 amino acids of a CryIF toxin and wherein said C-terminal protoxin portion comprises the CryIA(b) or CryIA(c)/CryIA(b) amino acid sequence which follows the peptide sequence shown in SEQ ID NO. 31.

8. The composition, according to claim 6, wherein said core toxin-containing protein comprises the amino acid sequence shown in SEQ ID NO. 23.

9. The composition, according to claim 6, wherein said core toxin-containing protein comprises the amino acid sequence shown in SEQ ID NO. 29.

10. The composition, according to claim 6, wherein said CryIF chimeric core toxin-containing protein comprises an amino acid sequence selected from the group consisting of SEQ ID NO. 35, SEQ ID NO. 36, SEQ ID NO. 37, and SEQ ID NO. 38.

11. The composition, according to claim 1, wherein said CryIA(c) chimeric core toxin-containing protein has an amino acid sequence shown in SEQ ID NO. 34.

12. The composition, according to claim 3, wherein said cell expresses SEQ ID NO. 23 and SEQ ID NO. 34.

13. The composition, according to claim 3, wherein said cell expresses SEQ ID NO. 29 and SEQ ID NO. 34.

14. A host transformed to express both a CryIF chimeric core toxin-containing protein and a CryIA(c) chimeric core toxin-containing protein, wherein said host is a microorganism or a plant cell.

15. A method for controlling lepidopteran pests comprising contacting said pests, or the environment of said pests, with an effective amount of a composition comprising cells which produce a CryIF chimeric core toxin-containing protein and a CryIA(c) chimeric core toxin-containing protein.

16. The method, according to claim 15, wherein said composition comprises a cell expressing a CryIF chimeric core toxin-containing protein and a cell expressing a CryIA(c) chimeric core toxin-containing protein.

17. The method, according to claim 15, wherein said composition comprises a cell expressing a CryIF chimeric core toxin-containing protein and a CryIA(c) chimeric core toxin-containing protein.

18. The method, according to claim 15, wherein said CryIF chimeric core toxin-containing protein comprises a CryIF core N-terminal toxin portion and a heterologous C-terminal protoxin portion from a CryIA(b) toxin or CryIA(b)/CryIA(c) chimeric toxin.

19. The method, according to claim 18, wherein said CryIF chimeric core toxin-containing protein has approximately 1150 to 1200 amino acids and comprises a CryIF core N-terminal sequence of at least about 590 amino acids and no more than about 1100 amino acids, wherein said CryIA(b) or CryIA(c)/CryIA(b) protoxin portion comprises at least 100 amino acids at the C-terminus of said protein.

20. The method, according to claim 18, wherein the transition from CryIF core N-terminal toxin portion to heterologous protoxin portion occurs after the sequence shown in SEQ ID NO. 30 and before the end of the peptide sequence of SEQ ID NO. 31.

21. The method, according to claim 20, wherein said core toxin portion comprises the first about 601 amino acids of a CryIF toxin and wherein said C-terminal protoxin portion comprises the CryIA(b) or CryIA(c)/CryIA(b) amino acid sequence which follows the peptide sequence shown in SEQ ID NO. 31.

22. The method, according to claim 20, wherein said core toxin-containing protein comprises the amino acid sequence shown in SEQ ID NO. 23.

23. The method, according to claim 20, wherein said core toxin-containing protein comprises the amino acid sequence shown in SEQ ID NO. 29.

24. The method, according to claim 20, wherein said CryIF chimeric core toxin-containing protein comprises an amino acid sequence selected from the group consisting of SEQ ID NO. 35, SEQ ID NO. 36, SEQ ID NO. 37, and SEQ ID NO. 38.

25. The method, according to claim 18, wherein said CryIA(c) chimeric core toxin-containing protein has an amino acid sequence shown in SEQ ID NO. 34.

26. The method, according to claim 17, wherein said cell expresses SEQ ID NO. 23 and SEQ ID NO. 34.

27. The method, according to claim 17, wherein said cell expresses SEQ ID NO. 29 and SEQ ID NO. 34.

28. The composition, according to claim 10, wherein said amino acid sequence is shown in SEQ ID NO. 35.

29. The composition, according to claim 10, wherein said amino acid sequence is shown in SEQ ID NO. 36.

30. The composition, according to claim 10, wherein said amino acid sequence is shown in SEQ ID NO. 37.

31. The composition, according to claim 10, wherein said amino acid sequence is shown in SEQ ID NO. 38.

32. The method, according to claim 24, wherein said amino acid sequence is shown in SEQ ID NO. 35.

33. The method, according to claim 24, wherein said amino acid sequence is shown in SEQ ID NO. 36.

34. The method, according to claim 24, wherein said amino acid sequence is shown in SEQ ID NO. 37.

35. The method, according to claim 24, wherein said amino acid sequence is shown in SEQ ID NO. 38.

* * * * *

UNITED STATES PATENT AND TRADEMARK OFFICE
CERTIFICATE OF CORRECTION

PATENT NO. : 5,827,514
DATED : October 27, 1998
INVENTOR(S) : Gregory A. Bradfisch, Mark Thompson, George E. Schwab It is certified that error appears in the above-identified patent and that said Letters Patent is hereby corrected as shown below:

Column 5, line 58: "show" should read --shown--; and line 63: "show" should read --shown--.

Column 11, line 35: "Agrobactenum" should read --*Agrobacterium*--.

Signed and Sealed this

Fifteenth Day of June, 1999

Attest:

Q. TODD DICKINSON

*Attesting Officer*    *Acting Commissioner of Patents and Trademarks*

SEQUENCE LISTING ( 1 ) GENERAL INFORMATION:

( i i i ) NUMBER OF SEQUENCES: 38

( 2 ) INFORMATION FOR SEQ ID NO:1:

( i ) SEQUENCE CHARACTERISTICS:
        ( A ) LENGTH: 39 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:1:

GCATACTAGT AGGAGATTTC CATGGATAAC AATCCGAAC    39

( 2 ) INFORMATION FOR SEQ ID NO:2:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:2:

GGATCCGCTT CCCAGTCT    18

( 2 ) INFORMATION FOR SEQ ID NO:3:

( i ) SEQUENCE CHARACTERISTICS:
        ( A ) LENGTH: 29 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:3:

AGAGAGTGGG AAGCGGATCC TACTAATCC    29

( 2 ) INFORMATION FOR SEQ ID NO:4:

( i ) SEQUENCE CHARACTERISTICS:
        ( A ) LENGTH: 28 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:4:

TGGATACTCG ATCGATATGA TAATCCGT    28

( 2 ) INFORMATION FOR SEQ ID NO:5:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:5:

TAATAAGAGC TCCTATGT                                                                                    18

( 2 ) INFORMATION FOR SEQ ID NO:6:

( i ) SEQUENCE CHARACTERISTICS:
        ( A ) LENGTH: 28 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:6:

TATCATATCG ATCGAGTATC CAATTTAG                                                                         28

( 2 ) INFORMATION FOR SEQ ID NO:7:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:7:

GTCACATAGC CAGCTGGT                                                                                    18

( 2 ) INFORMATION FOR SEQ ID NO:8:

( i ) SEQUENCE CHARACTERISTICS:
        ( A ) LENGTH: 36 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:8:

GAGTGGGAAG CAGATCTTAA TAATGCACAA TTAAGG                                                                36

( 2 ) INFORMATION FOR SEQ ID NO:9:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:9:

TTAATCATCG GCTCGTA                                                                                     17

( 2 ) INFORMATION FOR SEQ ID NO:10:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:10:

ACTCGATCGA TATGATARTC CGT                                                                              23

( 2 ) INFORMATION FOR SEQ ID NO:11:

( i ) SEQUENCE CHARACTERISTICS:
 ( A ) LENGTH: 45 bases
 ( B ) TYPE: nucleic acid
 ( C ) STRANDEDNESS: single
 ( D ) TOPOLOGY: linear ( i i ) MOLECULE TYPE: DNA (synthetic)

( x i ) SEQUENCE DESCRIPTION: SEQ ID NO:11:

GGACTAGTAA AAAGGAGATA ACCATGGAAA ATAATATTCA AAATC          45

( 2 ) INFORMATION FOR SEQ ID NO:12:

( i ) SEQUENCE CHARACTERISTICS:
  ( A ) LENGTH: 64 bases
  ( B ) TYPE: nucleic acid
  ( C ) STRANDEDNESS: single
  ( D ) TOPOLOGY: linear ( i i ) MOLECULE TYPE: DNA (synthetic)

( x i ) SEQUENCE DESCRIPTION: SEQ ID NO:12:

TCCAGCGGCA GGCGGCCGGT GCTGCGTTCT TCGTTCAGTA TTTCTACTTC AGGATTATTT          60

AAAC          64

( 2 ) INFORMATION FOR SEQ ID NO:13:

( i ) SEQUENCE CHARACTERISTICS:
  ( A ) LENGTH: 65 bases
  ( B ) TYPE: nucleic acid
  ( C ) STRANDEDNESS: single
  ( D ) TOPOLOGY: linear ( i i ) MOLECULE TYPE: DNA (synthetic)

( x i ) SEQUENCE DESCRIPTION: SEQ ID NO:13:

AACGCAGCAC CGGCCGCCTG CCGCTGGACA TCAGCCTGAG CCTTACACGT TTCCTTTTGA          60

GTGAA          65

( 2 ) INFORMATION FOR SEQ ID NO:14:

( i ) SEQUENCE CHARACTERISTICS:
  ( A ) LENGTH: 17 bases
  ( B ) TYPE: nucleic acid
  ( C ) STRANDEDNESS: single
  ( D ) TOPOLOGY: linear ( i i ) MOLECULE TYPE: DNA (synthetic)

( x i ) SEQUENCE DESCRIPTION: SEQ ID NO:14:

CATCAAAGGT ACCTGGT          17

( 2 ) INFORMATION FOR SEQ ID NO:15:

( i ) SEQUENCE CHARACTERISTICS:
  ( A ) LENGTH: 22 bases
  ( B ) TYPE: nucleic acid
  ( C ) STRANDEDNESS: single
  ( D ) TOPOLOGY: linear ( i i ) MOLECULE TYPE: DNA (synthetic)

( x i ) SEQUENCE DESCRIPTION: SEQ ID NO:15:

TGCCGCTGGA CATCAGCCTG AG          22

( 2 ) INFORMATION FOR SEQ ID NO:16:

( i ) SEQUENCE CHARACTERISTICS:

(A) LENGTH: 41 bases
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:16:

| TCTAGAGCGG | CCGCTTATAC | YCGATCGATA | TGATARTCCG | T | | 41 |
|---|---|---|---|---|---|---|

(2) INFORMATION FOR SEQ ID NO:17:

(i) SEQUENCE CHARACTERISTICS:
(A) LENGTH: 24 bases
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:17:

| AGGCTTCCAT | AGATACCTTG | TGCG | | | | 24 |
|---|---|---|---|---|---|---|

(2) INFORMATION FOR SEQ ID NO:18:

(i) SEQUENCE CHARACTERISTICS:
(A) LENGTH: 3465 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:18:

| ATGGATAACA | ATCCGAACAT | CAATGAATGC | ATTCCTTATA | ATTGTTTAAG | TAACCCTGAA | 60 |
|---|---|---|---|---|---|---|
| GTAGAAGTAT | TAGGTGGAGA | AAGAATAGAA | ACTGGTTACA | CCCCAATCGA | TATTTCCTTG | 120 |
| TCGCTAACGC | AATTTCTTTT | GAGTGAATTT | GTTCCCGGTG | CTGGATTTGT | GTTAGGACTA | 180 |
| GTTGATATAA | TATGGGGAAT | TTTTGGTCCC | TCTCAATGGG | ACGCATTTCT | TGTACAAATT | 240 |
| GAACAGTTAA | TTAACCAAAG | AATAGAAGAA | TTCGCTAGGA | ACCAAGCCAT | TTCTAGATTA | 300 |
| GAAGGACTAA | GCAATCTTTA | TCAAATTTAC | GCAGAATCTT | TTAGAGAGTG | GGAAGCGGAT | 360 |
| CCTACTAATC | CAGCATTAAG | AGAAGAGATG | CGTATTCAAT | TCAATGACAT | GAACAGTGCC | 420 |
| CTTACAACCG | CTATTCCTCT | TTTTGCAGTT | CAAAATTATC | AAGTTCCTCT | TTTATCAGTA | 480 |
| TATGTTCAAG | CTGCAAATTT | ACATTATCA | GTTTTGAGAG | ATGTTTCAGT | GTTTGGACAA | 540 |
| AGGTGGGGAT | TTGATGCCGC | GACTATCAAT | AGTCGTTATA | ATGATTTAAC | TAGGCTTATT | 600 |
| GGCAACTATA | CAGATTATGC | TGTACGCTGG | TACAATACGG | GATTAGAACG | TGTATGGGGA | 660 |
| CCGGATTCTA | GAGATTGGGT | AAGGTATAAT | CAATTTAGAA | GAGAATTAAC | ACTAACTGTA | 720 |
| TTAGATATCG | TTGCTCTGTT | CCCGAATTAT | GATAGTAGAA | GATATCCAAT | TCGAACAGTT | 780 |
| TCCCAATTAA | CAAGAGAAAT | TTATACAAAC | CCAGTATTAG | AAAATTTTGA | TGGTAGTTTT | 840 |
| CGAGGCTCGG | CTCAGGGCAT | AGAAAGAAGT | ATTAGGAGTC | CACATTTGAT | GGATATACTT | 900 |
| AACAGTATAA | CCATCTATAC | GGATGCTCAT | AGGGGTTATT | ATTATTGGTC | AGGGCATCAA | 960 |
| ATAATGGCTT | CTCCTGTAGG | GTTTTCGGGG | CCAGAATTCA | CTTTTCCGCT | ATATGGAACT | 1020 |
| ATGGGAAATG | CAGCTCCACA | ACAACGTATT | GTTGCTCAAC | TAGGTCAGGG | CGTGTATAGA | 1080 |
| ACATTATCGT | CCACTTTATA | TAGAAGACCT | TTTAATATAG | GGATAAATAA | TCAACAACTA | 1140 |
| TCTGTTCTTG | ACGGGACAGA | ATTTGCTTAT | GGAACCTCCT | CAAATTTGCC | ATCCGCTGTA | 1200 |
| TACAGAAAAA | GCGGAACGGT | AGATTCGCTG | GATGAAATAC | CGCCACAGAA | TAACAACGTG | 1260 |

| | | | | | |
|---|---|---|---|---|---|
|CCACCTAGGC|AAGGATTTAG|TCATCGATTA|AGCCATGTTT|CAATGTTTCG|TTCAGGCTTT|1320
|AGTAATAGTA|GTGTAAGTAT|AATAAGAGCT|CCTATGTTCT|CTTGGATACA|TCGTAGTGCT|1380
|GAATTTAATA|ATATAATTCC|TTCATCACAA|ATTACACAAA|TACCTTTAAC|AAAATCTACT|1440
|AATCTTGGCT|CTGGAACTTC|TGTCGTTAAA|GGACCAGGAT|TTACAGGAGG|AGATATTCTT|1500
|CGAAGAACTT|CACCTGGCCA|GATTTCAACC|TTAAGAGTAA|ATATTACTGC|ACCATTATCA|1560
|CAAAGATATC|GGGTAAGAAT|TCGCTACGCT|TCTACCACAA|ATTTACAATT|CCATACATCA|1620
|ATTGACGGAA|GACCTATTAA|TCAGGGGAAT|TTTTCAGCAA|CTATGAGTAG|TGGGAGTAAT|1680
|TTACAGTCCG|GAAGCTTTAG|GACTGTAGGT|TTTACTACTC|CGTTAACTT|TTCAAATGGA|1740
|TCAAGTGTAT|TTACGTTAAG|TGCTCATGTC|TTCAATTCAG|GCAATGAAGT|TTATATAGAT|1800
|CGAATTGAAT|TTGTTCCGGC|AGAAGTAACC|TTTGAGGCAG|AATATGATTT|AGAAAGAGCA|1860
|CAAAAGGCGG|TGAATGAGCT|GTTTACTTCT|TCCAATCAAA|TCGGGTAAA|AACAGATGTG|1920
|ACGGATTATC|ATATCGATCG|AGTATCCAAT|TTAGTTGAGT|GTTTATCTGA|TGAATTTTGT|1980
|CTGGATGAAA|AAAAAGAATT|GTCCGAGAAA|GTCAAACATG|CGAAGCGACT|TAGTGATGAG|2040
|CGGAATTTAC|TTCAAGATCC|AAACTTTAGA|GGGATCAATA|GACAACTAGA|CCGTGGCTGG|2100
|AGAGGAAGTA|CGGATATTAC|CATCCAAGGA|GGCGATGACG|TATTCAAAGA|GAATTACGTT|2160
|ACGCTATTGG|GTACCTTTGA|TGAGTGCTAT|CCAACGTATT|TATATCAAAA|AATAGATGAG|2220
|TCGAAATTAA|AAGCCTATAC|CCGTTACCAA|TTAAGAGGGT|ATATCGAAGA|TAGTCAAGAC|2280
|TTAGAAATCT|ATTTAATTCG|CTACAATGCC|AAACACGAAA|CAGTAAATGT|GCCAGGTACG|2340
|GGTTCCTTAT|GGCCGCTTTC|AGCCCCAAGT|CCAATCGGAA|AATGTGCCCA|TCATTCCCAT|2400
|CATTTCTCCT|TGGACATTGA|TGTTGGATGT|ACAGACTTAA|ATGAGGACTT|AGGTGTATGG|2460
|GTGATATTCA|AGATTAAGAC|GCAAGATGGC|CATGCAAGAC|TAGGAAATCT|AGAATTTCTC|2520
|GAAGAGAAAC|CATTAGTAGG|AGAAGCACTA|GCTCGTGTGA|AAAGAGCGGA|GAAAAAATGG|2580
|AGAGACAAAC|GTGAAAAATT|GGAATGGGAA|ACAAATATTG|TTTATAAAGA|GGCAAAGAA|2640
|TCTGTAGATG|CTTTATTTGT|AAACTCTCAA|TATGATAGAT|TACAAGCGGA|TACCAACATC|2700
|GCGATGATTC|ATGCGGCAGA|TAAACGCGTT|CATAGCATTC|GAGAAGCTTA|TCTGCCTGAG|2760
|CTGTCTGTGA|TTCCGGGTGT|CAATGCGGCT|ATTTTTGAAG|AATTAGAAGG|GCGTATTTTC|2820
|ACTGCATTCT|CCCTATATGA|TGCGAGAAAT|GTCATTAAAA|ATGGTGATTT|TAATAATGGC|2880
|TTATCCTGCT|GGAACGTGAA|AGGGCATGTA|GATGTAGAAG|AACAAAACAA|CCACCGTTCG|2940
|GTCCTTGTTG|TTCCGGAATG|GGAAGCAGAA|GTGTCACAAG|AAGTTCGTGT|CTGTCCGGGT|3000
|CGTGGCTATA|TCCTTCGTGT|CACAGCGTAC|AAGGAGGGAT|ATGGAGAAGG|TTGCGTAACC|3060
|ATTCATGAGA|TCGAGAACAA|TACAGACGAA|CTGAAGTTTA|GCAACTGTGT|AGAAGAGGAA|3120
|GTATATCCAA|ACAACACGGT|AACGTGTAAT|GATTATACTG|CGACTCAAGA|AGAATATGAG|3180
|GGTACGTACA|CTTCTCGTAA|TCGAGGATAT|GACGGAGCCT|ATGAAAGCAA|TTCTTCTGTA|3240
|CCAGCTGATT|ATGCATCAGC|CTATGAAGAA|AAAGCATATA|CAGATGGACG|AAGAGACAAT|3300
|CCTTGTGAAT|CTAACAGAGG|ATATGGGGAT|TACACACCAC|TACCAGCTGG|CTATGTGACA|3360
|AAAGAATTAG|AGTACTTCCC|AGAAACCGAT|AAGGTATGGA|TTGAGATCGG|AGAAACGGAA|3420
|GGAACATTCA|TCGTGGACAG|CGTGGAATTA|CTTCTTATGG|AGGAA| |3465

( 2 ) INFORMATION FOR SEQ ID NO:19:

( i ) SEQUENCE CHARACTERISTICS:
        ( A ) LENGTH: 1155 amino acids (B) TYPE: amino acid
(C) STRANDEDNESS: single
(D) TOPOLOGY: linear (ii) MOLECULE TYPE: protein (xi) SEQUENCE DESCRIPTION: SEQ ID NO:19:

```
Met  Asp  Asn  Asn  Pro  Asn  Ile  Asn  Glu  Cys  Ile  Pro  Tyr  Asn  Cys  Leu
 1                  5                    10                       15

Ser  Asn  Pro  Glu  Val  Glu  Val  Leu  Gly  Glu  Arg  Ile  Glu  Thr  Gly
                20                  25                       30

Tyr  Thr  Pro  Ile  Asp  Ile  Ser  Leu  Ser  Leu  Thr  Gln  Phe  Leu  Leu  Ser
           35                       40                       45

Glu  Phe  Val  Pro  Gly  Ala  Gly  Phe  Val  Leu  Gly  Leu  Val  Asp  Ile  Ile
      50                       55                       60

Trp  Gly  Ile  Phe  Gly  Pro  Ser  Gln  Trp  Asp  Ala  Phe  Leu  Val  Gln  Ile
65                       70                  75                            80

Glu  Gln  Leu  Ile  Asn  Gln  Arg  Ile  Glu  Glu  Phe  Ala  Arg  Asn  Gln  Ala
                85                       90                       95

Ile  Ser  Arg  Leu  Glu  Gly  Leu  Ser  Asn  Leu  Tyr  Gln  Ile  Tyr  Ala  Glu
               100                      105                      110

Ser  Phe  Arg  Glu  Trp  Glu  Ala  Asp  Pro  Thr  Asn  Pro  Ala  Leu  Arg  Glu
               115                      120                      125

Glu  Met  Arg  Ile  Gln  Phe  Asn  Asp  Met  Asn  Ser  Ala  Leu  Thr  Thr  Ala
          130                      135                      140

Ile  Pro  Leu  Phe  Ala  Val  Gln  Asn  Tyr  Gln  Val  Pro  Leu  Leu  Ser  Val
145                      150                      155                      160

Tyr  Val  Gln  Ala  Ala  Asn  Leu  His  Leu  Ser  Val  Leu  Arg  Asp  Val  Ser
                    165                      170                      175

Val  Phe  Gly  Gln  Arg  Trp  Gly  Phe  Asp  Ala  Ala  Thr  Ile  Asn  Ser  Arg
               180                      185                      190

Tyr  Asn  Asp  Leu  Thr  Arg  Leu  Ile  Gly  Asn  Tyr  Thr  Asp  Tyr  Ala  Val
               195                      200                      205

Arg  Trp  Tyr  Asn  Thr  Gly  Leu  Glu  Arg  Val  Trp  Gly  Pro  Asp  Ser  Arg
     210                      215                      220

Asp  Trp  Val  Arg  Tyr  Asn  Gln  Phe  Arg  Arg  Glu  Leu  Thr  Leu  Thr  Val
225                      230                      235                      240

Leu  Asp  Ile  Val  Ala  Leu  Phe  Pro  Asn  Tyr  Asp  Ser  Arg  Arg  Tyr  Pro
                    245                      250                      255

Ile  Arg  Thr  Val  Ser  Gln  Leu  Thr  Arg  Glu  Ile  Tyr  Thr  Asn  Pro  Val
               260                      265                      270

Leu  Glu  Asn  Phe  Asp  Gly  Ser  Phe  Arg  Gly  Ser  Ala  Gln  Gly  Ile  Glu
          275                      280                      285

Arg  Ser  Ile  Arg  Ser  Pro  His  Leu  Met  Asp  Ile  Leu  Asn  Ser  Ile  Thr
     290                      295                      300

Ile  Tyr  Thr  Asp  Ala  His  Arg  Gly  Tyr  Tyr  Tyr  Trp  Ser  Gly  His  Gln
305                      310                      315                      320

Ile  Met  Ala  Ser  Pro  Val  Gly  Phe  Ser  Gly  Pro  Glu  Phe  Thr  Phe  Pro
                    325                      330                      335

Leu  Tyr  Gly  Thr  Met  Gly  Asn  Ala  Ala  Pro  Gln  Gln  Arg  Ile  Val  Ala
               340                      345                      350

Gln  Leu  Gly  Gln  Gly  Val  Tyr  Arg  Thr  Leu  Ser  Ser  Thr  Leu  Tyr  Arg
          355                      360                      365

Arg  Pro  Phe  Asn  Ile  Gly  Ile  Asn  Asn  Gln  Gln  Leu  Ser  Val  Leu  Asp
     370                      375                      380
```

```
Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
                500                 505                 510

Val Asn Ile Thr Ala Pro Leu Ser Gln Arg Tyr Arg Val Arg Ile Arg
            515                 520                 525

Tyr Ala Ser Thr Thr Asn Leu Gln Phe His Thr Ser Ile Asp Gly Arg
        530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
            580                 585                 590

Ser Gly Asn Glu Val Tyr Ile Asp Arg Ile Glu Phe Val Pro Ala Glu
        595                 600                 605

Val Thr Phe Glu Ala Glu Tyr Asp Leu Glu Arg Ala Gln Lys Ala Val
    610                 615                 620

Asn Glu Leu Phe Thr Ser Ser Asn Gln Ile Gly Leu Lys Thr Asp Val
625                 630                 635                 640

Thr Asp Tyr His Ile Asp Arg Val Ser Asn Leu Val Glu Cys Leu Ser
                645                 650                 655

Asp Glu Phe Cys Leu Asp Glu Lys Lys Glu Leu Ser Glu Lys Val Lys
            660                 665                 670

His Ala Lys Arg Leu Ser Asp Glu Arg Asn Leu Leu Gln Asp Pro Asn
        675                 680                 685

Phe Arg Gly Ile Asn Arg Gln Leu Asp Arg Gly Trp Arg Gly Ser Thr
    690                 695                 700

Asp Ile Thr Ile Gln Gly Gly Asp Asp Val Phe Lys Glu Asn Tyr Val
705                 710                 715                 720

Thr Leu Leu Gly Thr Phe Asp Glu Cys Tyr Pro Thr Tyr Leu Tyr Gln
                725                 730                 735

Lys Ile Asp Glu Ser Lys Leu Lys Ala Tyr Thr Arg Tyr Gln Leu Arg
            740                 745                 750

Gly Tyr Ile Glu Asp Ser Gln Asp Leu Glu Ile Tyr Leu Ile Arg Tyr
        755                 760                 765

Asn Ala Lys His Glu Thr Val Asn Val Pro Gly Thr Gly Ser Leu Trp
    770                 775                 780

Pro Leu Ser Ala Pro Ser Pro Ile Gly Lys Cys Ala His His Ser His
785                 790                 795                 800

His Phe Ser Leu Asp Ile Asp Val Gly Cys Thr Asp Leu Asn Glu Asp
                805                 810                 815
```

-continued

| | | | | | | | | | | | | | | |
|---|---|---|---|---|---|---|---|---|---|---|---|---|---|---|
| Leu | Gly | Val | Trp<br>820 | Val | Ile | Phe | Lys<br>825 | Ile | Lys | Thr | Gln | Asp | Gly<br>830 | His | Ala |
| Arg | Leu | Gly<br>835 | Asn | Leu | Glu | Phe | Leu<br>840 | Glu | Glu | Lys | Pro | Leu<br>845 | Val | Gly | Glu |
| Ala | Leu<br>850 | Ala | Arg | Val | Lys | Arg<br>855 | Ala | Glu | Lys | Lys | Trp<br>860 | Arg | Asp | Lys | Arg |
| Glu<br>865 | Lys | Leu | Glu | Trp | Glu<br>870 | Thr | Asn | Ile | Val | Tyr<br>875 | Lys | Glu | Ala | Lys | Glu<br>880 |
| Ser | Val | Asp | Ala | Leu<br>885 | Phe | Val | Asn | Ser | Gln<br>890 | Tyr | Asp | Arg | Leu | Gln<br>895 | Ala |
| Asp | Thr | Asn | Ile<br>900 | Ala | Met | Ile | His | Ala<br>905 | Ala | Asp | Lys | Arg | Val<br>910 | His | Ser |
| Ile | Arg | Glu<br>915 | Ala | Tyr | Leu | Pro | Glu<br>920 | Leu | Ser | Val | Ile | Pro<br>925 | Gly | Val | Asn |
| Ala | Ala<br>930 | Ile | Phe | Glu | Glu | Leu<br>935 | Glu | Gly | Arg | Ile | Phe<br>940 | Thr | Ala | Phe | Ser |
| Leu<br>945 | Tyr | Asp | Ala | Arg | Asn<br>950 | Val | Ile | Lys | Asn | Gly<br>955 | Asp | Phe | Asn | Asn | Gly<br>960 |
| Leu | Ser | Cys | Trp | Asn<br>965 | Val | Lys | Gly | His | Val<br>970 | Asp | Val | Glu | Glu | Gln<br>975 | Asn |
| Asn | His | Arg | Ser<br>980 | Val | Leu | Val | Val | Pro<br>985 | Glu | Trp | Glu | Ala | Glu<br>990 | Val | Ser |
| Gln | Glu | Val<br>995 | Arg | Val | Cys | Pro | Gly<br>1000 | Arg | Gly | Tyr | Ile | Leu<br>1005 | Arg | Val | Thr |
| Ala | Tyr | Lys<br>1010 | Glu | Gly | Tyr | Gly<br>1015 | Glu | Gly | Cys | Val | Thr<br>1020 | Ile | His | Glu | Ile |
| Glu<br>1025 | Asn | Asn | Thr | Asp | Glu<br>1030 | Leu | Lys | Phe | Ser | Asn<br>1035 | Cys | Val | Glu | Glu | Glu<br>1040 |
| Val | Tyr | Pro | Asn | Asn<br>1045 | Thr | Val | Thr | Cys | Asn<br>1050 | Asp | Tyr | Thr | Ala | Thr<br>1055 | Gln |
| Glu | Glu | Tyr | Glu<br>1060 | Gly | Thr | Tyr | Thr | Ser<br>1065 | Arg | Asn | Arg | Gly | Tyr<br>1070 | Asp | Gly |
| Ala | Tyr | Glu<br>1075 | Ser | Asn | Ser | Ser | Val<br>1080 | Pro | Ala | Asp | Tyr | Ala<br>1085 | Ser | Ala | Tyr |
| Glu | Glu<br>1090 | Lys | Ala | Tyr | Thr | Asp<br>1095 | Gly | Arg | Arg | Asp | Asn<br>1100 | Pro | Cys | Glu | Ser |
| Asn | Arg<br>1105 | Gly | Tyr | Gly | Asp | Tyr<br>1110 | Thr | Pro | Leu | Pro | Ala<br>1115 | Gly | Tyr | Val | Thr<br>1120 |
| Lys | Glu | Leu | Glu | Tyr<br>1125 | Phe | Pro | Glu | Thr | Asp<br>1130 | Lys | Val | Trp | Ile | Glu<br>1135 | Ile |
| Gly | Glu | Thr | Glu<br>1140 | Gly | Thr | Phe | Ile | Val<br>1145 | Asp | Ser | Val | Glu | Leu<br>1150 | Leu | Leu |
| Met | Glu | Glu<br>1155 | | | | | | | | | | | | | |

( 2 ) INFORMATION FOR SEQ ID NO:20:

( i ) SEQUENCE CHARACTERISTICS:
        ( A ) LENGTH: 3450 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

-continued

| | | | | | | |
|---|---|---|---|---|---|---|
| ATGGATAACA | ATCCGAACAT | CAATGAATGC | ATTCCTTATA | ATTGTTTAAG | TAACCCTGAA | 60 |
| GTAGAAGTAT | TAGGTGGAGA | AAGAATAGAA | ACTGGTTACA | CCCCAATCGA | TATTTCCTTG | 120 |
| TCGCTAACGC | AATTTCTTTT | GAGTGAATTT | GTTCCGGTG | CTGGATTTGT | GTTAGGACTA | 180 |
| GTTGATATAA | TATGGGGAAT | TTTTGGTCCC | TCTCAATGGG | ACGCATTTCT | TGTACAAATT | 240 |
| GAACAGTTAA | TTAACCAAAG | AATAGAAGAA | TTCGCTAGGA | ACCAAGCCAT | TTCTAGATTA | 300 |
| GAAGGACTAA | GCAATCTTTA | TCAAATTTAC | GCAGAATCTT | TTAGAGAGTG | GGAAGCGGAT | 360 |
| CTTAATAATG | CACAATTAAG | GGAAGATGTG | CGTATTCGAT | TGCTAATAC | AGACGACGCT | 420 |
| TTAATAACAG | CAATAAATAA | TTTTACACTT | ACAAGTTTTG | AAATCCCTCT | TTTATCGGTC | 480 |
| TATGTTCAAG | CGGCGAATTT | ACATTATCA | CTATTAAGAG | ACGCTGTATC | GTTTGGGCAG | 540 |
| GGTTGGGGAC | TGGATATAGC | TACTGTTAAT | AATCATTATA | ATAGATTAAT | AAATCTTATT | 600 |
| CATAGATATA | CGAAACATTG | TTTGGACACA | TACAATCAAG | GATTAGAAAA | CTTAAGAGGT | 660 |
| ACTAATACTC | GACAATGGGC | AAGATTCAAT | CAGTTTAGGA | GAGATTTAAC | ACTTACTGTA | 720 |
| TTAGATATCG | TTGCTCTTTT | TCCGAACTAC | GATGTTAGAA | CATATCCAAT | TCAAACGTCA | 780 |
| TCCCAATTAA | CAAGGGAAAT | TTATACAAGT | TCAGTAATTG | AGGATTCTCC | AGTTCTGCT | 840 |
| AATATACCTA | ATGGTTTTAA | TAGGGCGGAA | TTTGGAGTTA | GACCGCCCCA | TCTTATGGAC | 900 |
| TTTATGAATT | CTTTGTTTGT | AACTGCAGAG | ACTGTTAGAA | GTCAAACTGT | GTGGGGAGGA | 960 |
| CACTTAGTTA | GTTCACGAAA | TACGGCTGGT | AACCGTATAA | ATTTCCCTAG | TTACGGGGTC | 1020 |
| TTCAATCCTG | GTGGCGCCAT | TTGGATTGCA | GATGAGGATC | CACGTCCTTT | TATCGGACA | 1080 |
| TTATCAGATC | CTGTTTTTGT | CCGAGGAGGA | TTTGGGAATC | CTCATTATGT | ACTGGGGCTT | 1140 |
| AGGGAGTAG | CATTTCAACA | AACTGGTACG | AACCACACCC | GAACATTTAG | AAATAGTGGG | 1200 |
| ACCATAGATT | CTCTAGATGA | AATCCCACCT | CAGGATAATA | GTGGGGCACC | TTGGAATGAT | 1260 |
| TATAGTCATG | TATTAAATCA | TGTTACATTT | GTACGATGGC | CAGGTGAGAT | TCAGGAAGT | 1320 |
| GATTCATGGA | GAGCTCCAAT | GTTTTCTTGG | ACGCACCGTA | GTGCAACCCC | TACAAATACA | 1380 |
| ATTGATCCGG | AGAGGATTAC | TCAAATACCA | TTGGTAAAAG | CACATACACT | TCAGTCAGGT | 1440 |
| ACTACTGTTG | TAAGAGGGCC | CGGGTTTACG | GGAGGAGATA | TTCTTCGACG | AACAAGTGGA | 1500 |
| GGACCATTTG | CTTATACTAT | TGTTAATATA | AATGGGCAAT | TACCCCAAAG | GTATCGTGCA | 1560 |
| AGAATACGCT | ATGCCTCTAC | TACAAATCTA | GAATTTACG | TAACGGTTGC | AGGTGAACGG | 1620 |
| ATTTTGCTG | GTCAATTTAA | CAAAACAATG | GATACCGGTG | ACCCATTAAC | ATTCCAATCT | 1680 |
| TTTAGTTACG | CAACTATTAA | TACAGCTTTT | ACATTCCCAA | TGAGCCAGAG | TAGTTTCACA | 1740 |
| GTAGGTGCTG | ATACTTTTAG | TTCAGGGAAT | GAAGTTTATA | TAGACAGATT | TGAATTGATT | 1800 |
| CCAGTTACTG | CAACATTTGA | AGCAGAATAT | GATTTAGAAA | GAGCACAAAA | GGCGGTGAAT | 1860 |
| GCGCTGTTTA | CTTCTATAAA | CCAAATAGGG | ATAAAAACAG | ATGTGACGGA | TTATCATATC | 1920 |
| GATCGAGTAT | CCAATTTAGT | TGAGTGTTTA | TCTGATGAAT | TTTGTCTGGA | TGAAAAAAAA | 1980 |
| GAATTGTCCG | AGAAAGTCAA | ACATGCGAAG | CGACTTAGTG | ATGAGCGGAA | TTTACTTCAA | 2040 |
| GATCCAAACT | TTAGAGGGAT | CAATAGACAA | CTAGACCGTG | GCTGGAGAGG | AAGTACGGAT | 2100 |
| ATTACCATCC | AAGGAGGCGA | TGACGTATTC | AAAGAGAATT | ACGTTACGCT | ATTGGGTACC | 2160 |
| TTTGATGAGT | GCTATCCAAC | GTATTTATAT | CAAAAAATAG | ATGAGTCGAA | ATTAAAAGCC | 2220 |
| TATACCCGTT | ACCAATTAAG | AGGGTATATC | GAAGATAGTC | AAGACTTAGA | AATCTATTTA | 2280 |
| ATTCGCTACA | ATGCCAAACA | CGAAACAGTA | AATGTGCCAG | GTACGGGTTC | CTTATGGCCG | 2340 |
| CTTTCAGCCC | CAAGTCCAAT | CGGAAAATGT | GCCCATCATT | CCCATCATTT | CTCCTTGGAC | 2400 |

```
ATTGATGTTG  GATGTACAGA  CTTAAATGAG  GACTTAGGTG  TATGGGTGAT  ATTCAAGATT    2460

AAGACGCAAG  ATGGCCATGC  AAGACTAGGA  AATCTAGAAT  TTCTCGAAGA  GAAACCATTA    2520

GTAGGAGAAG  CACTAGCTCG  TGTGAAAAGA  GCGGAGAAAA  AATGGAGAGA  CAAACGTGAA    2580

AAATTGGAAT  GGGAAACAAA  TATTGTTTAT  AAAGAGGCAA  AAGAATCTGT  AGATGCTTTA    2640

TTTGTAAACT  CTCAATATGA  TAGATTACAA  GCGGATACCA  ACATCGCGAT  GATTCATGCG    2700

GCAGATAAAC  GCGTTCATAG  CATTCGAGAA  GCTTATCTGC  CTGAGCTGTC  TGTGATTCCG    2760

GGTGTCAATG  CGGCTATTTT  TGAAGAATTA  GAAGGGCGTA  TTTTCACTGC  ATTCTCCCTA    2820

TATGATGCGA  GAAATGTCAT  TAAAAATGGT  GATTTTAATA  ATGGCTTATC  CTGCTGGAAC    2880

GTGAAAGGGC  ATGTAGATGT  AGAAGAACAA  AACAACCACC  GTTCGGTCCT  TGTTGTTCCG    2940

GAATGGGAAG  CAGAAGTGTC  ACAAGAAGTT  CGTGTCTGTC  CGGGTCGTGG  CTATATCCTT    3000

CGTGTCACAG  CGTACAAGGA  GGGATATGGA  GAAGGTTGCG  TAACCATTCA  TGAGATCGAG    3060

AACAATACAG  ACGAACTGAA  GTTTAGCAAC  TGTGTAGAAG  AGGAAGTATA  TCCAAACAAC    3120

ACGGTAACGT  GTAATGATTA  TACTGCGACT  CAAGAAGAAT  ATGAGGGTAC  GTACACTTCT    3180

CGTAATCGAG  GATATGACGG  AGCCTATGAA  AGCAATTCTT  CTGTACCAGC  TGATTATGCA    3240

TCAGCCTATG  AAGAAAAAGC  ATATACAGAT  GGACGAAGAG  ACAATCCTTG  TGAATCTAAC    3300

AGAGGATATG  GGGATTACAC  ACCACTACCA  GCTGGCTATG  TGACAAAAGA  ATTAGAGTAC    3360

TTCCCAGAAA  CCGATAAGGT  ATGGATTGAG  ATCGGAGAAA  CGGAAGGAAC  ATTCATCGTG    3420

GACAGCGTGG  AATTACTTCT  TATGGAGGAA                                        3450
```

( 2 ) INFORMATION FOR SEQ ID NO:21:

( i ) SEQUENCE CHARACTERISTICS:
        ( A ) LENGTH: 1150 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:21:

```
Met  Asp  Asn  Asn  Pro  Asn  Ile  Asn  Glu  Cys  Ile  Pro  Tyr  Asn  Cys  Leu
 1                 5                     10                      15

Ser  Asn  Pro  Glu  Val  Glu  Val  Leu  Gly  Gly  Glu  Arg  Ile  Glu  Thr  Gly
              20                      25                      30

Tyr  Thr  Pro  Ile  Asp  Ile  Ser  Leu  Ser  Leu  Thr  Gln  Phe  Leu  Leu  Ser
              35                      40                      45

Glu  Phe  Val  Pro  Gly  Ala  Gly  Phe  Val  Leu  Gly  Leu  Val  Asp  Ile  Ile
         50                      55                      60

Trp  Gly  Ile  Phe  Gly  Pro  Ser  Gln  Trp  Asp  Ala  Phe  Leu  Val  Gln  Ile
 65                      70                      75                      80

Glu  Gln  Leu  Ile  Asn  Gln  Arg  Ile  Glu  Glu  Phe  Ala  Arg  Asn  Gln  Ala
                   85                      90                      95

Ile  Ser  Arg  Leu  Glu  Gly  Leu  Ser  Asn  Leu  Tyr  Gln  Ile  Tyr  Ala  Glu
                  100                     105                     110

Ser  Phe  Arg  Glu  Trp  Glu  Ala  Asp  Leu  Asn  Asn  Ala  Gln  Leu  Arg  Glu
              115                     120                     125

Asp  Val  Arg  Ile  Arg  Phe  Ala  Asn  Thr  Asp  Asp  Ala  Leu  Ile  Thr  Ala
         130                     135                     140

Ile  Asn  Asn  Phe  Thr  Leu  Thr  Ser  Phe  Glu  Ile  Pro  Leu  Leu  Ser  Val
145                     150                     155                     160

Tyr  Val  Gln  Ala  Ala  Asn  Leu  His  Leu  Ser  Leu  Leu  Arg  Asp  Ala  Val
```

-continued

|   |   |   |   | 165 |   |   |   | 170 |   |   |   | 175 |   |   |
|---|---|---|---|---|---|---|---|---|---|---|---|---|---|---|
| Ser | Phe | Gly | Gln<br>180 | Gly | Trp | Gly | Leu<br>185 | Asp | Ile | Ala | Thr | Val<br>190 | Asn | His |
| Tyr | Asn | Arg<br>195 | Leu | Ile | Asn | Leu<br>200 | Ile | His | Arg | Tyr | Thr<br>205 | Lys | His | Cys | Leu |
| Asp | Thr<br>210 | Tyr | Asn | Gln | Gly<br>215 | Leu | Glu | Asn | Leu | Arg<br>220 | Gly | Thr | Asn | Thr | Arg |
| Gln<br>225 | Trp | Ala | Arg | Phe | Asn<br>230 | Gln | Phe | Arg | Arg<br>235 | Asp | Leu | Thr | Leu | Thr | Val<br>240 |
| Leu | Asp | Ile | Val | Ala<br>245 | Leu | Phe | Pro | Asn | Tyr<br>250 | Asp | Val | Arg | Thr | Tyr<br>255 | Pro |
| Ile | Gln | Thr | Ser<br>260 | Ser | Gln | Leu | Thr | Arg<br>265 | Glu | Ile | Tyr | Thr | Ser<br>270 | Ser | Val |
| Ile | Glu | Asp<br>275 | Ser | Pro | Val | Ser | Ala<br>280 | Asn | Ile | Pro | Asn | Gly<br>285 | Phe | Asn | Arg |
| Ala | Glu<br>290 | Phe | Gly | Val | Arg | Pro<br>295 | Pro | His | Leu | Met | Asp<br>300 | Phe | Met | Asn | Ser |
| Leu<br>305 | Phe | Val | Thr | Ala | Glu<br>310 | Thr | Val | Arg | Ser | Gln<br>315 | Thr | Val | Trp | Gly | Gly<br>320 |
| His | Leu | Val | Ser | Ser<br>325 | Arg | Asn | Thr | Ala | Gly<br>330 | Asn | Arg | Ile | Asn | Phe<br>335 | Pro |
| Ser | Tyr | Gly | Val<br>340 | Phe | Asn | Pro | Gly | Gly<br>345 | Ala | Ile | Trp | Ile | Ala<br>350 | Asp | Glu |
| Asp | Pro | Arg<br>355 | Pro | Phe | Tyr | Arg | Thr<br>360 | Leu | Ser | Asp | Pro | Val<br>365 | Phe | Val | Arg |
| Gly | Gly<br>370 | Phe | Gly | Asn | Pro | His<br>375 | Tyr | Val | Leu | Gly | Leu<br>380 | Arg | Gly | Val | Ala |
| Phe<br>385 | Gln | Gln | Thr | Gly | Thr<br>390 | Asn | His | Thr | Arg | Thr<br>395 | Phe | Arg | Asn | Ser | Gly<br>400 |
| Thr | Ile | Asp | Ser | Leu<br>405 | Asp | Glu | Ile | Pro | Pro<br>410 | Gln | Asp | Asn | Ser | Gly<br>415 | Ala |
| Pro | Trp | Asn | Asp<br>420 | Tyr | Ser | His | Val | Leu<br>425 | Asn | His | Val | Thr | Phe<br>430 | Val | Arg |
| Trp | Pro | Gly<br>435 | Glu | Ile | Ser | Gly | Ser<br>440 | Asp | Ser | Trp | Arg | Ala<br>445 | Pro | Met | Phe |
| Ser | Trp<br>450 | Thr | His | Arg | Ser | Ala<br>455 | Thr | Pro | Thr | Asn | Thr<br>460 | Ile | Asp | Pro | Glu |
| Arg<br>465 | Ile | Thr | Gln | Ile | Pro<br>470 | Leu | Val | Lys | Ala | His<br>475 | Thr | Leu | Gln | Ser | Gly<br>480 |
| Thr | Thr | Val | Val | Arg<br>485 | Gly | Pro | Gly | Phe | Thr<br>490 | Gly | Gly | Asp | Ile | Leu<br>495 | Arg |
| Arg | Thr | Ser | Gly<br>500 | Gly | Pro | Phe | Ala | Tyr<br>505 | Thr | Ile | Val | Asn | Ile<br>510 | Asn | Gly |
| Gln | Leu | Pro<br>515 | Gln | Arg | Tyr | Arg | Ala<br>520 | Arg | Ile | Arg | Tyr | Ala<br>525 | Ser | Thr | Thr |
| Asn | Leu<br>530 | Arg | Ile | Tyr | Val | Thr<br>535 | Val | Ala | Gly | Glu | Arg<br>540 | Ile | Phe | Ala | Gly |
| Gln<br>545 | Phe | Asn | Lys | Thr | Met<br>550 | Asp | Thr | Gly | Asp | Pro<br>555 | Leu | Thr | Phe | Gln | Ser<br>560 |
| Phe | Ser | Tyr | Ala | Thr<br>565 | Ile | Asn | Thr | Ala | Phe<br>570 | Thr | Phe | Pro | Met | Ser<br>575 | Gln |
| Ser | Ser | Phe | Thr<br>580 | Val | Gly | Ala | Asp | Thr<br>585 | Phe | Ser | Ser | Gly | Asn<br>590 | Glu | Val |

```
Tyr  Ile  Asp  Arg  Phe  Glu  Leu  Ile  Pro  Val  Thr  Ala  Thr  Phe  Glu  Ala
          595                      600                      605

Glu  Tyr  Asp  Leu  Glu  Arg  Ala  Gln  Lys  Ala  Val  Asn  Ala  Leu  Phe  Thr
     610                      615                      620

Ser  Ile  Asn  Gln  Ile  Gly  Ile  Lys  Thr  Asp  Thr  Asp  Tyr  His  Ile
625                           630                      635                      640

Asp  Arg  Val  Ser  Asn  Leu  Val  Glu  Cys  Leu  Ser  Asp  Glu  Phe  Cys  Leu
                    645                      650                           655

Asp  Glu  Lys  Lys  Glu  Leu  Ser  Glu  Lys  Val  Lys  His  Ala  Lys  Arg  Leu
               660                      665                      670

Ser  Asp  Glu  Arg  Asn  Leu  Leu  Gln  Asp  Pro  Asn  Phe  Arg  Gly  Ile  Asn
          675                      680                      685

Arg  Gln  Leu  Asp  Arg  Gly  Trp  Arg  Gly  Ser  Thr  Asp  Ile  Thr  Ile  Gln
     690                      695                      700

Gly  Gly  Asp  Asp  Val  Phe  Lys  Glu  Asn  Tyr  Val  Thr  Leu  Leu  Gly  Thr
705                           710                      715                      720

Phe  Asp  Glu  Cys  Tyr  Pro  Thr  Tyr  Leu  Tyr  Gln  Lys  Ile  Asp  Glu  Ser
                    725                      730                      735

Lys  Leu  Lys  Ala  Tyr  Thr  Arg  Tyr  Gln  Leu  Arg  Gly  Tyr  Ile  Glu  Asp
               740                      745                      750

Ser  Gln  Asp  Leu  Glu  Ile  Tyr  Leu  Ile  Arg  Tyr  Asn  Ala  Lys  His  Glu
          755                      760                      765

Thr  Val  Asn  Val  Pro  Gly  Thr  Gly  Ser  Leu  Trp  Pro  Leu  Ser  Ala  Pro
770                           775                      780

Ser  Pro  Ile  Gly  Lys  Cys  Ala  His  His  Ser  His  His  Phe  Ser  Leu  Asp
785                      790                      795                           800

Ile  Asp  Val  Gly  Cys  Thr  Asp  Leu  Asn  Glu  Asp  Leu  Gly  Val  Trp  Val
                    805                      810                      815

Ile  Phe  Lys  Ile  Lys  Thr  Gln  Asp  Gly  His  Ala  Arg  Leu  Gly  Asn  Leu
               820                      825                      830

Glu  Phe  Leu  Glu  Glu  Lys  Pro  Leu  Val  Gly  Glu  Ala  Leu  Ala  Arg  Val
          835                      840                      845

Lys  Arg  Ala  Glu  Lys  Lys  Trp  Arg  Asp  Lys  Arg  Glu  Lys  Leu  Glu  Trp
     850                      855                      860

Glu  Thr  Asn  Ile  Val  Tyr  Lys  Glu  Ala  Lys  Glu  Ser  Val  Asp  Ala  Leu
865                           870                      875                      880

Phe  Val  Asn  Ser  Gln  Tyr  Asp  Arg  Leu  Gln  Ala  Asp  Thr  Asn  Ile  Ala
                    885                      890                      895

Met  Ile  His  Ala  Ala  Asp  Lys  Arg  Val  His  Ser  Ile  Arg  Glu  Ala  Tyr
               900                      905                      910

Leu  Pro  Glu  Leu  Ser  Val  Ile  Pro  Gly  Val  Asn  Ala  Ala  Ile  Phe  Glu
          915                      920                      925

Glu  Leu  Glu  Gly  Arg  Ile  Phe  Thr  Ala  Phe  Ser  Leu  Tyr  Asp  Ala  Arg
     930                      935                      940

Asn  Val  Ile  Lys  Asn  Gly  Asp  Phe  Asn  Asn  Gly  Leu  Ser  Cys  Trp  Asn
945                           950                      955                      960

Val  Lys  Gly  His  Val  Asp  Val  Glu  Glu  Gln  Asn  Asn  His  Arg  Ser  Val
                    965                      970                      975

Leu  Val  Val  Pro  Glu  Trp  Glu  Ala  Glu  Val  Ser  Gln  Glu  Val  Arg  Val
               980                      985                      990

Cys  Pro  Gly  Arg  Gly  Tyr  Ile  Leu  Arg  Val  Thr  Ala  Tyr  Lys  Glu  Gly
          995                      1000                     1005

Tyr  Gly  Glu  Gly  Cys  Val  Thr  Ile  His  Glu  Ile  Glu  Asn  Asn  Thr  Asp
     1010                     1015                     1020
```

-continued

```
Glu Leu Lys Phe Ser Asn Cys Val Glu Glu Val Tyr Pro Asn Asn
1025                1030            1035            1040

Thr Val Thr Cys Asn Asp Tyr Thr Ala Thr Gln Glu Glu Tyr Glu Gly
            1045            1050            1055

Thr Tyr Thr Ser Arg Asn Arg Gly Tyr Asp Gly Ala Tyr Glu Ser Asn
            1060            1065            1070

Ser Ser Val Pro Ala Asp Tyr Ala Ser Ala Tyr Glu Glu Lys Ala Tyr
        1075            1080            1085

Thr Asp Gly Arg Arg Asp Asn Pro Cys Glu Ser Asn Arg Gly Tyr Gly
    1090            1095            1100

Asp Tyr Thr Pro Leu Pro Ala Gly Tyr Val Thr Lys Glu Leu Glu Tyr
1105            1110            1115            1120

Phe Pro Glu Thr Asp Lys Val Trp Ile Glu Ile Gly Glu Thr Glu Gly
                1125            1130            1135

Thr Phe Ile Val Asp Ser Val Glu Leu Leu Leu Met Glu Glu
            1140            1145            1150
```

( 2 ) INFORMATION FOR SEQ ID NO:22:

( i ) SEQUENCE CHARACTERISTICS:
        ( A ) LENGTH: 3444 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

```
ATGGAGAATA ATATTCAAAA TCAATGCGTA CCTTACAATT GTTTAAATAA TCCTGAAGTA      60
GAAATATTAA ATGAAGAAAG AAGTACTGGC AGATTACCGT TAGATATATC CTTATCGCTT     120
ACACGTTTCC TTTTGAGTGA ATTTGTTCCA GGTGTGGGAG TTGCGTTTGG ATTATTTGAT     180
TTAATATGGG GTTTTATAAC TCCTTCTGAT GGAGCTTAT  TTCTTTTACA GATTGAACAA     240
TTGATTGAGC AAAGAATAGA AACATTGGAA AGGAACCGGG CAATTACTAC ATTACGAGGG     300
TTAGCAGATA GCTATGAAAT TTATATTGAA GCACTAAGAG AGTGGGAAGC AAATCCTAAT     360
AATGCACAAT TAAGGGAAGA TGTGCGTATT CGATTGCTA  ATACAGACGA CGCTTTAATA     420
ACAGCAATAA ATAATTTTAC ACTTACAAGT TTTGAAATCC CTCTTTTATC GGTCTATGTT     480
CAAGCGGCGA ATTTACATTT ATCACTATTA AGAGACGCTG TATCGTTTGG GCAGGGTTGG     540
GGACTGGATA TAGCTACTGT TAATAATCAT TATAATAGAT TAATAAATCT TATTCATAGA     600
TATACGAAAC ATTGTTTGGA CACATACAAT CAAGGATTAG AAAACTTAAG AGGTACTAAT     660
ACTCGACAAT GGGCAAGATT CAATCAGTTT AGGAGAGATT TAACACTTAC TGTATTAGAT     720
ATCGTTGCTC TTTTTCCGAA CTACGATGTT AGAACATATC CAATTCAAAC GTCATCCAA      780
TTAACAAGGG AAATTTATAC AAGTTCAGTA ATTGAGGATT CTCCAGTTTC TGCTAATATA     840
CCTAATGGTT TTAATAGGGC GGAATTTGGA GTTAGACCGC CCATCTTAT  GGACTTTATG     900
AATTCTTTGT TTGTAACTGC AGAGACTGTT AGAAGTCAAA CTGTGTGGGG AGGACACTTA     960
GTTAGTTCAC GAAATACGGC TGGTAACCGT ATAAATTTCC CTAGTTACGG GGTCTTCAAT    1020
CCTGGTGGCG CCATTTGGAT TGCAGATGAG GATCCACGTC CTTTTTATCG GACATTATCA    1080
GATCCTGTTT TTGTCCGAGG AGGATTTGGG AATCCTCATT ATGTACTGGG GCTTAGGGGA    1140
GTAGCATTTC AACAAACTGG TACGAACCAC ACCCGAACAT TTAGAAATAG TGGGACCATA    1200
GATTCTCTAG ATGAAATCCC ACCTCAGGAT AATAGTGGGG CACCTTGGAA TGATTATAGT    1260
```

| | | | | | | |
|---|---|---|---|---|---|---|
| CATGTATTAA | ATCATGTTAC | ATTTGTACGA | TGGCCAGGTG | AGATTTCAGG | AAGTGATTCA | 1320 |
| TGGAGAGCTC | CAATGTTTTC | TTGGACGCAC | CGTAGTGCAA | CCCCTACAAA | TACAATTGAT | 1380 |
| CCGGAGAGGA | TTACTCAAAT | ACCATTGGTA | AAAGCACATA | CACTTCAGTC | AGGTACTACT | 1440 |
| GTTGTAAGAG | GGCCCGGGTT | TACGGGAGGA | GATATTCTTC | GACGAACAAG | TGGAGGACCA | 1500 |
| TTTGCTTATA | CTATTGTTAA | TATAAATGGG | CAATTACCCC | AAAGGTATCG | TGCAAGAATA | 1560 |
| CGCTATGCCT | CTACTACAAA | TCTAAGAATT | TACGTAACGG | TTGCAGGTGA | ACGGATTTTT | 1620 |
| GCTGGTCAAT | TTAACAAAAC | AATGGATACC | GGTGACCCAT | TAACATTCCA | ATCTTTTAGT | 1680 |
| TACGCAACTA | TTAATACAGC | TTTTACATTC | CCAATGAGCC | AGAGTAGTTT | CACAGTAGGT | 1740 |
| GCTGATACTT | TTAGTTCAGG | GAATGAAGTT | TATATAGACA | GATTTGAATT | GATTCCAGTT | 1800 |
| ACTGCAACAT | TTGAAGCAGA | ATATGATTTA | GAAAGAGCAC | AAAAGGCGGT | GAATGCGCTG | 1860 |
| TTTACTTCTA | TAAACCAAAT | AGGGATAAAA | ACAGATGTGA | CGGATTATCA | TATCGATCGA | 1920 |
| GTATCCAATT | TAGTTGAGTG | TTTATCTGAT | GAATTTTGTC | TGGATGAAAA | AAAAGAATTG | 1980 |
| TCCGAGAAAG | TCAAACATGC | GAAGCGACTT | AGTGATGAGC | GGAATTTACT | TCAAGATCCA | 2040 |
| AACTTTAGAG | GGATCAATAG | ACAACTAGAC | CGTGGCTGGA | GAGGAAGTAC | GGATATTACC | 2100 |
| ATCCAAGGAG | GCGATGACGT | ATTCAAAGAG | AATTACGTTA | CGCTATTGGG | TACCTTTGAT | 2160 |
| GAGTGCTATC | CAACGTATTT | ATATCAAAAA | ATAGATGAGT | CGAAATTAAA | AGCCTATACC | 2220 |
| CGTTACCAAT | TAAGAGGGTA | TATCGAAGAT | AGTCAAGACT | TAGAAATCTA | TTTAATTCGC | 2280 |
| TACAATGCCA | AACACGAAAC | AGTAAATGTG | CCAGGTACGG | GTTCCTTATG | GCCGCTTTCA | 2340 |
| GCCCCAAGTC | CAATCGGAAA | ATGTGCCCAT | CATTCCCATC | ATTTCTCCTT | GGACATTGAT | 2400 |
| GTTGGATGTA | CAGACTTAAA | TGAGGACTTA | GGTGTATGGG | TGATATTCAA | GATTAAGACG | 2460 |
| CAAGATGGCC | ATGCAAGACT | AGGAAATCTA | GAATTTCTCG | AAGAGAAACC | ATTAGTAGGA | 2520 |
| GAAGCACTAG | CTCGTGTGAA | AAGAGCGGAG | AAAAAATGGA | GAGACAAACG | TGAAAAATTG | 2580 |
| GAATGGGAAA | CAAATATTGT | TTATAAAGAG | GCAAAAGAAT | CTGTAGATGC | TTTATTTGTA | 2640 |
| AACTCTCAAT | ATGATAGATT | ACAAGCGGAT | ACCAACATCG | CGATGATTCA | TGCGGCAGAT | 2700 |
| AAACGCGTTC | ATAGCATTCG | AGAAGCTTAT | CTGCCTGAGC | TGTCTGTGAT | TCCGGGTGTC | 2760 |
| AATGCGGCTA | TTTTTGAAGA | ATTAGAAGGG | CGTATTTTCA | CTGCATTCTC | CCTATATGAT | 2820 |
| GCGAGAAATG | TCATTAAAAA | TGGTGATTTT | AATAATGGCT | TATCCTGCTG | GAACGTGAAA | 2880 |
| GGGCATGTAG | ATGTAGAAGA | ACAAAACAAC | CACCGTTCGG | TCCTTGTTGT | TCCGGAATGG | 2940 |
| GAAGCAGAAG | TGTCACAAGA | AGTTCGTGTC | TGTCCGGGTC | GTGGCTATAT | CCTTCGTGTC | 3000 |
| ACAGCGTACA | AGGAGGGATA | TGGAGAAGGT | TGCGTAACCA | TTCATGAGAT | CGAGAACAAT | 3060 |
| ACAGACGAAC | TGAAGTTTAG | CAACTGTGTA | GAAGAGGAAG | TATATCCAAA | CAACACGGTA | 3120 |
| ACGTGTAATG | ATTATACTGC | GACTCAAGAA | GAATATGAGG | GTACGTACAC | TTCTCGTAAT | 3180 |
| CGAGGATATG | ACGGAGCCTA | TGAAAGCAAT | TCTTCTGTAC | CAGCTGATTA | TGCATCAGCC | 3240 |
| TATGAAGAAA | AAGCATATAC | AGATGGACGA | AGAGACAATC | CTTGTGAATC | TAACAGAGGA | 3300 |
| TATGGGGATT | ACACACCACT | ACCAGCTGGC | TATGTGACAA | AAGAATTAGA | GTACTTCCCA | 3360 |
| GAAACCGATA | AGGTATGGAT | TGAGATCGGA | GAAACGGAAG | GAACATTCAT | CGTGGACAGC | 3420 |
| GTGGAATTAC | TTCTTATGGA | GGAA | | | | 3444 |

( 2 ) INFORMATION FOR SEQ ID NO:23:

( i ) SEQUENCE CHARACTERISTICS:
        ( A ) LENGTH: 1148 amino acids
        ( B ) TYPE: amino acid -continued (C) STRANDEDNESS: single
(D) TOPOLOGY: linear (ii) MOLECULE TYPE: protein (xi) SEQUENCE DESCRIPTION: SEQ ID NO:23:

```
Met  Glu  Asn  Asn  Ile  Gln  Asn  Gln  Cys  Val  Pro  Tyr  Asn  Cys  Leu  Asn
 1               5                        10                       15

Asn  Pro  Glu  Val  Glu  Ile  Leu  Asn  Glu  Glu  Arg  Ser  Thr  Gly  Arg  Leu
           20                       25                            30

Pro  Leu  Asp  Ile  Ser  Leu  Ser  Leu  Thr  Arg  Phe  Leu  Leu  Ser  Glu  Phe
           35                       40                       45

Val  Pro  Gly  Val  Gly  Val  Ala  Phe  Gly  Leu  Phe  Asp  Leu  Ile  Trp  Gly
 50                            55                       60

Phe  Ile  Thr  Pro  Ser  Asp  Trp  Ser  Leu  Phe  Leu  Gln  Ile  Glu  Gln
 65                       70                       75                       80

Leu  Ile  Glu  Gln  Arg  Ile  Glu  Thr  Leu  Glu  Arg  Asn  Arg  Ala  Ile  Thr
                     85                       90                       95

Thr  Leu  Arg  Gly  Leu  Ala  Asp  Ser  Tyr  Glu  Ile  Tyr  Ile  Glu  Ala  Leu
                100                       105                      110

Arg  Glu  Trp  Glu  Ala  Asn  Pro  Asn  Asn  Ala  Gln  Leu  Arg  Glu  Asp  Val
           115                      120                      125

Arg  Ile  Arg  Phe  Ala  Asn  Thr  Asp  Asp  Ala  Leu  Ile  Thr  Ala  Ile  Asn
     130                      135                      140

Asn  Phe  Thr  Leu  Thr  Ser  Phe  Glu  Ile  Pro  Leu  Leu  Ser  Val  Tyr  Val
145                      150                      155                      160

Gln  Ala  Ala  Asn  Leu  His  Leu  Ser  Leu  Leu  Arg  Asp  Ala  Val  Ser  Phe
                     165                      170                      175

Gly  Gln  Gly  Trp  Gly  Leu  Asp  Ile  Ala  Thr  Val  Asn  Asn  His  Tyr  Asn
                180                      185                      190

Arg  Leu  Ile  Asn  Leu  Ile  His  Arg  Tyr  Thr  Lys  His  Cys  Leu  Asp  Thr
           195                      200                      205

Tyr  Asn  Gln  Gly  Leu  Glu  Asn  Leu  Arg  Gly  Thr  Asn  Thr  Arg  Gln  Trp
     210                      215                      220

Ala  Arg  Phe  Asn  Gln  Phe  Arg  Arg  Asp  Leu  Thr  Leu  Thr  Val  Leu  Asp
225                      230                      235                      240

Ile  Val  Ala  Leu  Phe  Pro  Asn  Tyr  Asp  Val  Arg  Thr  Tyr  Pro  Ile  Gln
                245                      250                      255

Thr  Ser  Ser  Gln  Leu  Thr  Arg  Glu  Ile  Tyr  Thr  Ser  Ser  Val  Ile  Glu
                260                      265                      270

Asp  Ser  Pro  Val  Ser  Ala  Asn  Ile  Pro  Asn  Gly  Phe  Asn  Arg  Ala  Glu
           275                      280                      285

Phe  Gly  Val  Arg  Pro  Pro  His  Leu  Met  Asp  Phe  Met  Asn  Ser  Leu  Phe
     290                      295                      300

Val  Thr  Ala  Glu  Thr  Val  Arg  Ser  Gln  Thr  Val  Trp  Gly  Gly  His  Leu
305                      310                      315                      320

Val  Ser  Ser  Arg  Asn  Thr  Ala  Gly  Asn  Arg  Ile  Asn  Phe  Pro  Ser  Tyr
                325                      330                      335

Gly  Val  Phe  Asn  Pro  Gly  Gly  Ala  Ile  Trp  Ile  Ala  Asp  Glu  Asp  Pro
                340                      345                      350

Arg  Pro  Phe  Tyr  Arg  Thr  Leu  Ser  Asp  Pro  Val  Phe  Val  Arg  Gly  Gly
           355                      360                      365

Phe  Gly  Asn  Pro  His  Tyr  Val  Leu  Gly  Leu  Arg  Gly  Val  Ala  Phe  Gln
           370                      375                      380

Gln  Thr  Gly  Thr  Asn  His  Thr  Arg  Thr  Phe  Arg  Asn  Ser  Gly  Thr  Ile
```

```
                385                      390                      395                      400

Asp  Ser  Leu  Asp  Glu  Ile  Pro  Pro  Gln  Asn  Ser  Gly  Ala  Pro  Trp
                           405                      410                      415

Asn  Asp  Tyr  Ser  His  Val  Leu  Asn  His  Val  Thr  Phe  Val  Arg  Trp  Pro
                      420                      425                      430

Gly  Glu  Ile  Ser  Gly  Ser  Asp  Ser  Trp  Arg  Ala  Pro  Met  Phe  Ser  Trp
                      435                      440                      445

Thr  His  Arg  Ser  Ala  Thr  Pro  Thr  Asn  Thr  Ile  Asp  Pro  Glu  Arg  Ile
             450                      455                      460

Thr  Gln  Ile  Pro  Leu  Val  Lys  Ala  His  Thr  Leu  Gln  Ser  Gly  Thr  Thr
        465                      470                      475                      480

Val  Val  Arg  Gly  Pro  Gly  Phe  Thr  Gly  Gly  Asp  Ile  Leu  Arg  Arg  Thr
                           485                      490                      495

Ser  Gly  Gly  Pro  Phe  Ala  Tyr  Thr  Ile  Val  Asn  Ile  Asn  Gly  Gln  Leu
                      500                      505                      510

Pro  Gln  Arg  Tyr  Arg  Ala  Arg  Ile  Arg  Tyr  Ala  Ser  Thr  Thr  Asn  Leu
                      515                      520                      525

Arg  Ile  Tyr  Val  Thr  Val  Ala  Gly  Glu  Arg  Ile  Phe  Ala  Gly  Gln  Phe
                      530                      535                      540

Asn  Lys  Thr  Met  Asp  Thr  Gly  Asp  Pro  Leu  Thr  Phe  Gln  Ser  Phe  Ser
        545                      550                      555                      560

Tyr  Ala  Thr  Ile  Asn  Thr  Ala  Phe  Thr  Phe  Pro  Met  Ser  Gln  Ser  Ser
                           565                      570                      575

Phe  Thr  Val  Gly  Ala  Asp  Thr  Phe  Ser  Ser  Gly  Asn  Glu  Val  Tyr  Ile
                      580                      585                      590

Asp  Arg  Phe  Glu  Leu  Ile  Pro  Val  Thr  Ala  Thr  Phe  Glu  Ala  Glu  Tyr
                      595                      600                      605

Asp  Leu  Glu  Arg  Ala  Gln  Lys  Ala  Val  Asn  Ala  Leu  Phe  Thr  Ser  Ile
        610                      615                      620

Asn  Gln  Ile  Gly  Ile  Lys  Thr  Asp  Val  Thr  Asp  Tyr  His  Ile  Asp  Arg
        625                      630                      635                      640

Val  Ser  Asn  Leu  Val  Glu  Cys  Leu  Ser  Asp  Glu  Phe  Cys  Leu  Asp  Glu
                           645                      650                      655

Lys  Lys  Glu  Leu  Ser  Glu  Lys  Val  Lys  His  Ala  Lys  Arg  Leu  Ser  Asp
                           660                      665                      670

Glu  Arg  Asn  Leu  Leu  Gln  Asp  Pro  Asn  Phe  Arg  Gly  Ile  Asn  Arg  Gln
                      675                      680                      685

Leu  Asp  Arg  Gly  Trp  Arg  Gly  Ser  Thr  Asp  Ile  Thr  Ile  Gln  Gly  Gly
                           690                      695                      700

Asp  Asp  Val  Phe  Lys  Glu  Asn  Tyr  Val  Thr  Leu  Leu  Gly  Thr  Phe  Asp
        705                      710                      715                      720

Glu  Cys  Tyr  Pro  Thr  Tyr  Leu  Tyr  Gln  Lys  Ile  Asp  Glu  Ser  Lys  Leu
                           725                      730                      735

Lys  Ala  Tyr  Thr  Arg  Tyr  Gln  Leu  Arg  Gly  Tyr  Ile  Glu  Asp  Ser  Gln
                           740                      745                      750

Asp  Leu  Glu  Ile  Tyr  Leu  Ile  Arg  Tyr  Asn  Ala  Lys  His  Glu  Thr  Val
                      755                      760                      765

Asn  Val  Pro  Gly  Thr  Gly  Ser  Leu  Trp  Pro  Leu  Ser  Ala  Pro  Ser  Pro
        770                      775                      780

Ile  Gly  Lys  Cys  Ala  His  His  Ser  His  His  Phe  Ser  Leu  Asp  Ile  Asp
        785                      790                      795                      800

Val  Gly  Cys  Thr  Asp  Leu  Asn  Glu  Asp  Leu  Gly  Val  Trp  Val  Ile  Phe
                           805                      810                      815
```

| | | | | | | | | | | | | | | | |
|---|---|---|---|---|---|---|---|---|---|---|---|---|---|---|---|
| Lys | Ile | Lys | Thr | Gln | Asp | Gly | His | Ala | Arg | Leu | Gly | Asn | Leu | Glu | Phe |
| | | | 820 | | | | 825 | | | | | | 830 | | |
| Leu | Glu | Glu | Lys | Pro | Leu | Val | Gly | Glu | Ala | Leu | Ala | Arg | Val | Lys | Arg |
| | | 835 | | | | | 840 | | | | | 845 | | | |
| Ala | Glu | Lys | Lys | Trp | Arg | Asp | Lys | Arg | Glu | Lys | Leu | Glu | Trp | Glu | Thr |
| | 850 | | | | | 855 | | | | | 860 | | | | |
| Asn | Ile | Val | Tyr | Lys | Glu | Ala | Lys | Glu | Ser | Val | Asp | Ala | Leu | Phe | Val |
| 865 | | | | | 870 | | | | 875 | | | | | | 880 |
| Asn | Ser | Gln | Tyr | Asp | Arg | Leu | Gln | Ala | Asp | Thr | Asn | Ile | Ala | Met | Ile |
| | | | | 885 | | | | | 890 | | | | | 895 | |
| His | Ala | Ala | Asp | Lys | Arg | Val | His | Ser | Ile | Arg | Glu | Ala | Tyr | Leu | Pro |
| | | | 900 | | | | | 905 | | | | | 910 | | |
| Glu | Leu | Ser | Val | Ile | Pro | Gly | Val | Asn | Ala | Ala | Ile | Phe | Glu | Glu | Leu |
| | | 915 | | | | | 920 | | | | | 925 | | | |
| Glu | Gly | Arg | Ile | Phe | Thr | Ala | Phe | Ser | Leu | Tyr | Asp | Ala | Arg | Asn | Val |
| | 930 | | | | | 935 | | | | | 940 | | | | |
| Ile | Lys | Asn | Gly | Asp | Phe | Asn | Asn | Gly | Leu | Ser | Cys | Trp | Asn | Val | Lys |
| 945 | | | | | 950 | | | | | 955 | | | | | 960 |
| Gly | His | Val | Asp | Val | Glu | Glu | Gln | Asn | Asn | His | Arg | Ser | Val | Leu | Val |
| | | | | 965 | | | | | 970 | | | | | 975 | |
| Val | Pro | Glu | Trp | Glu | Ala | Glu | Val | Ser | Gln | Glu | Val | Arg | Val | Cys | Pro |
| | | | 980 | | | | | 985 | | | | | 990 | | |
| Gly | Arg | Gly | Tyr | Ile | Leu | Arg | Val | Thr | Ala | Tyr | Lys | Glu | Gly | Tyr | Gly |
| | | 995 | | | | | 1000 | | | | | 1005 | | | |
| Glu | Gly | Cys | Val | Thr | Ile | His | Glu | Ile | Glu | Asn | Asn | Thr | Asp | Glu | Leu |
| | 1010 | | | | | 1015 | | | | | 1020 | | | | |
| Lys | Phe | Ser | Asn | Cys | Val | Glu | Glu | Val | Tyr | Pro | Asn | Asn | Thr | Val | |
| 1025 | | | | | 1030 | | | | 1035 | | | | | 1040 | |
| Thr | Cys | Asn | Asp | Tyr | Thr | Ala | Thr | Gln | Glu | Glu | Tyr | Glu | Gly | Thr | Tyr |
| | | | | 1045 | | | | | 1050 | | | | | 1055 | |
| Thr | Ser | Arg | Asn | Arg | Gly | Tyr | Asp | Gly | Ala | Tyr | Glu | Ser | Asn | Ser | Ser |
| | | | 1060 | | | | | 1065 | | | | | 1070 | | |
| Val | Pro | Ala | Asp | Tyr | Ala | Ser | Ala | Tyr | Glu | Glu | Lys | Ala | Tyr | Thr | Asp |
| | | | 1075 | | | | | 1080 | | | | | 1085 | | |
| Gly | Arg | Arg | Asp | Asn | Pro | Cys | Glu | Ser | Asn | Arg | Gly | Tyr | Gly | Asp | Tyr |
| | | | 1090 | | | | | 1095 | | | | | 1100 | | |
| Thr | Pro | Leu | Pro | Ala | Gly | Tyr | Val | Thr | Lys | Glu | Leu | Glu | Tyr | Phe | Pro |
| 1105 | | | | | 1110 | | | | | 1115 | | | | | 1120 |
| Glu | Thr | Asp | Lys | Val | Trp | Ile | Glu | Ile | Gly | Glu | Thr | Glu | Gly | Thr | Phe |
| | | | | | 1125 | | | | | 1130 | | | | | 1135 |
| Ile | Val | Asp | Ser | Val | Glu | Leu | Leu | Leu | Met | Glu | Glu | | | | |
| | | | | 1140 | | | | | 1145 | | | | | | |

(2) INFORMATION FOR SEQ ID NO:24:

(i) SEQUENCE CHARACTERISTICS:
        (A) LENGTH: 3522 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

```
ATGGAAAATA ATATTCAAAA TCAATGCGTA CCTTACAATT GTTTAAATAA TCCTGAAGTA    60
GAAATACTGA ACGAAGAACG CAGCACCGGC CGCCTGCCGC TGGACATCAG CCTGAGCCTT   120
```

| | | | | | | |
|---|---|---|---|---|---|---|
| ACACGTTTCC | TTTTGAGTGA | ATTTGTTCCA | GGTGTGGGAG | TTGCGTTTGG | ATTATTTGAT | 180 |
| TTAATATGGG | GTTTTATAAC | TCCTTCTGAT | TGGAGCTTAT | TTCTTTTACA | GATTGAACAA | 240 |
| TTGATTGAGC | AAAGAATAGA | AACATTGGAA | AGGAACCGGG | CAATTACTAC | ATTACGAGGG | 300 |
| TTAGCAGATA | GCTATGAAAT | TTATATTGAA | GCACTAAGAG | AGTGGGAAGC | AAATCCTAAT | 360 |
| AATGCACAAT | TAAGGGAAGA | TGTGCGTATT | CGATTGCTA | ATACAGACGA | CGCTTTAATA | 420 |
| ACAGCAATAA | ATAATTTTAC | ACTTACAAGT | TTTGAAATCC | CTCTTTTATC | GGTCTATGTT | 480 |
| CAAGCGGCGA | ATTTACATTT | ATCACTATTA | AGAGACGCTG | TATCGTTTGG | GCAGGGTTGG | 540 |
| GGACTGGATA | TAGCTACTGT | TAATAATCAT | TATAATAGAT | TAATAAATCT | TATTCATAGA | 600 |
| TATACGAAAC | ATTGTTTGGA | CACATACAAT | CAAGGATTAG | AAAACTTAAG | AGGTACTAAT | 660 |
| ACTCGACAAT | GGGCAAGATT | CAATCAGTTT | AGGAGAGATT | TAACACTTAC | TGTATTAGAT | 720 |
| ATCGTTGCTC | TTTTTCCGAA | CTACGATGTT | AGAACATATC | CAATTCAAAC | GTCATCCAA | 780 |
| TTAACAAGGG | AAATTTATAC | AAGTTCAGTA | ATTGAGGATT | CTCCAGTTTC | TGCTAATATA | 840 |
| CCTAATGGTT | TTAATAGGGC | GGAATTTGGA | GTTAGACCGC | CCCATCTTAT | GGACTTTATG | 900 |
| AATTCTTTGT | TTGTAACTGC | AGAGACTGTT | AGAAGTCAAA | CTGTGTGGGG | AGGACACTTA | 960 |
| GTTAGTTCAC | GAAATACGGC | TGGTAACCGT | ATAAATTTCC | CTAGTTACGG | GGTCTTCAAT | 1020 |
| CCTGGTGGCG | CCATTTGGAT | TGCAGATGAG | GATCCACGTC | CTTTTTATCG | GACATTATCA | 1080 |
| GATCCTGTTT | TTGTCCGAGG | AGGATTTGGG | AATCCTCATT | ATGTACTGGG | GCTTAGGGGA | 1140 |
| GTAGCATTTC | AACAAACTGG | TACGAACCAC | ACCCGAACAT | TTAGAAATAG | TGGGACCATA | 1200 |
| GATTCTCTAG | ATGAAATCCC | ACCTCAGGAT | AATAGTGGGG | CACCTTGGAA | TGATTATAGT | 1260 |
| CATGTATTAA | ATCATGTTAC | ATTTGTACGA | TGGCCAGGTG | AGATTTCAGG | AAGTGATTCA | 1320 |
| TGGAGAGCTC | CAATGTTTTC | TTGGACGCAC | CGTAGTGCAA | CCCCTACAAA | TACAATTGAT | 1380 |
| CCGGAGAGGA | TTACTCAAAT | ACCATTGGTA | AAAGCACATA | CACTTCAGTC | AGGTACTACT | 1440 |
| GTTGTAAGAG | GGCCCGGGTT | TACGGGAGGA | GATATTCTTC | GACGAACAAG | TGGAGGACCA | 1500 |
| TTTGCTTATA | CTATTGTTAA | TATAAATGGG | CAATTACCCC | AAAGGTATCG | TGCAAGAATA | 1560 |
| CGCTATGCCT | CTACTACAAA | TCTAAGAATT | TACGTAACGG | TTGCAGGTGA | ACGGATTTTT | 1620 |
| GCTGGTCAAT | TTAACAAAAC | AATGGATACC | GGTGACCCAT | TAACATTCCA | ATCTTTTAGT | 1680 |
| TACGCAACTA | TTAATACAGC | TTTTACATTC | CCAATGAGCC | AGAGTAGTTT | CACAGTAGGT | 1740 |
| GCTGATACTT | TTAGTTCAGG | GAATGAAGTT | TATATAGACA | GATTTGAATT | GATTCCAGTT | 1800 |
| ACTGCAACAT | TTGAAGCAGA | ATATGATTTA | GAAAGAGCAC | AAAAGGCGGT | GAATGCGCTG | 1860 |
| TTTACTTCTA | TAAACCAAAT | AGGGATAAAA | ACAGATGTGA | CGGATTATCA | TATTGATCAA | 1920 |
| GTATCCAATT | TAGTGGATTG | TTTATCAGAT | GAATTTTGTC | TGGATGAAAA | GCGAGAATTG | 1980 |
| TCCGAGAAAG | TCAAACATGC | GAAGCGACTC | AGTGATGAGC | GGAATTTACT | TCAAGATCCA | 2040 |
| AACTTCAAAG | GCATCAATAG | GCAACTAGAC | CGTGGTTGGA | GAGGAAGTAC | GGATATTACC | 2100 |
| ATCCAAAGAG | GAGATGACGT | ATTCAAAGAA | AATTATGTCA | CACTACCAGG | TACCTTTGAT | 2160 |
| GAGTGCTATC | CAACGTATTT | ATATCAAAAA | ATAGATGAGT | CGAAATTAAA | ACCCTATACT | 2220 |
| CGTTATCAAT | TAAGAGGGTA | TATCGAGGAT | AGTCAAGACT | TAGAAATCTA | TTTGATCCGC | 2280 |
| TATAATGCAA | AACACGAAAC | AGTAAATGTG | CTAGGTACGG | GTTCTTTATG | GCCGCTTTCA | 2340 |
| GTCCAAAGTC | CAATCAGAAA | GTGTGGAGAA | CCGAATCGAT | GCGCGCCACA | CCTTGAATGG | 2400 |
| AATCCTGATC | TAGATTGTTC | CTGCAGAGAC | GGGGAAAAAT | GTGCACATCA | TTCGCATCAT | 2460 |
| TTCTCCTTGG | ACATTGATGT | TGGATGTACA | GACTTAAATG | AGGACTTAGA | TGTATGGGTG | 2520 |

-continued

```
ATATTCAAGA TTAAGACGCA AGATGGCCAT GCAAGACTAG GAAATCTAGA GTTTCTCGAA      2580
GAGAAACCAT TAGTCGGGGA AGCACTAGCT CGTGTGAAAA GAGCAGAGAA AAAATGGAGA      2640
GATAAACGTG AAAAATTGGA ATTGGAAACA AATATTGTTT ATAAAGAGGC AAAAGAATCT      2700
GTAGATGCTT TATTTGTAAA CTCTCAATAT GATCAATTAC AAGCGGATAC GAATATTGCC      2760
ATGATTCATG CGGCAGATAA ACGTGTTCAT AGAATTCGGG AAGCGTATCT TCCAGAGTTA      2820
TCTGTGATTC CGGGTGTAAA TGTAGACATT TTCGAAGAAT TAAAAGGGCG TATTTTCACT      2880
GCATTCTTCC TATATGATGC GAGAAATGTC ATTAAAAACG GTGATTTCAA TAATGGCTTA      2940
TCATGCTGGA ACGTGAAAGG GCATGTAGAT GTAGAAGAAC AAAACAACCA CCGTTCGGTC      3000
CTTGTTGTTC CGGAATGGGA AGCAGAAGTG TCACAAGAAG TTCGTGTCTG TCCGGGTCGT      3060
GGCTATATCC TTCGTGTCAC AGCGTACAAG GAGGGATATG GAGAAGGTTG CGTAACCATT      3120
CATGAGATCG AGAACAATAC AGACGAACTG AAGTTTAGCA ACTGCGTAGA AGAGGAAGTC      3180
TATCCAAACA ACACGGTAAC GTGTAATGAT TATACTGCAA ATCAAGAAGA ATACGGGGGT      3240
GCGTACACTT CCCGTAATCG TGGATATGAC GAAACTTATG GAAGCAATTC TTCTGTACCA      3300
GCTGATTATG CGTCAGTCTA TGAAGAAAAA TCGTATACAG ATGGACGAAG AGACAATCCT      3360
TGTGAATCTA ACAGAGGATA TGGGGATTAC ACACCACTAC CAGCTGGCTA TGTGACAAAA      3420
GAATTAGAGT ACTTCCCAGA AACCGATAAG GTATGGATTG AGATCGGAGA AACGGAAGGA      3480
ACATTCATCG TGGACAGCGT GGAATTACTC CTTATGGAGG AA                        3522
```

( 2 ) INFORMATION FOR SEQ ID NO:25:

( i ) SEQUENCE CHARACTERISTICS:
  ( A ) LENGTH: 1174 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:25:

```
Met Glu Asn Asn Ile Gln Asn Gln Cys Val Pro Tyr Asn Cys Leu Asn
 1               5                  10                  15

Asn Pro Glu Val Glu Ile Leu Asn Glu Glu Arg Ser Thr Gly Arg Leu
                20                  25                  30

Pro Leu Asp Ile Ser Leu Ser Leu Thr Arg Phe Leu Leu Ser Glu Phe
            35                  40                  45

Val Pro Gly Val Gly Val Ala Phe Gly Leu Phe Asp Leu Ile Trp Gly
        50                  55                  60

Phe Ile Thr Pro Ser Asp Trp Ser Leu Phe Leu Leu Gln Ile Glu Gln
 65                  70                  75                  80

Leu Ile Glu Gln Arg Ile Glu Thr Leu Glu Arg Asn Arg Ala Ile Thr
                85                  90                  95

Thr Leu Arg Gly Leu Ala Asp Ser Tyr Glu Ile Tyr Ile Glu Ala Leu
            100                 105                 110

Arg Glu Trp Glu Ala Asn Pro Asn Asn Ala Gln Leu Arg Glu Asp Val
        115                 120                 125

Arg Ile Arg Phe Ala Asn Thr Asp Asp Ala Leu Ile Thr Ala Ile Asn
    130                 135                 140

Asn Phe Thr Leu Thr Ser Phe Glu Ile Pro Leu Leu Ser Val Tyr Val
145                 150                 155                 160

Gln Ala Ala Asn Leu His Leu Ser Leu Leu Arg Asp Ala Val Ser Phe
                165                 170                 175
```

```
Gly Gln Gly Trp Gly Leu Asp Ile Ala Thr Val Asn Asn His Tyr Asn
            180                 185                 190

Arg Leu Ile Asn Leu Ile His Arg Tyr Thr Lys His Cys Leu Asp Thr
        195                 200                 205

Tyr Asn Gln Gly Leu Glu Asn Leu Arg Gly Thr Thr Arg Gln Trp
    210                 215                 220

Ala Arg Phe Asn Gln Phe Arg Arg Asp Leu Thr Leu Thr Val Leu Asp
225                 230                 235                 240

Ile Val Ala Leu Phe Pro Asn Tyr Asp Val Arg Thr Tyr Pro Ile Gln
            245                 250                 255

Thr Ser Ser Gln Leu Thr Arg Glu Ile Tyr Thr Ser Ser Val Ile Glu
            260                 265                 270

Asp Ser Pro Val Ser Ala Asn Ile Pro Asn Gly Phe Asn Arg Ala Glu
        275                 280                 285

Phe Gly Val Arg Pro Pro His Leu Met Asp Phe Met Asn Ser Leu Phe
    290                 295                 300

Val Thr Ala Glu Thr Val Arg Ser Gln Thr Val Trp Gly Gly His Leu
305                 310                 315                 320

Val Ser Ser Arg Asn Thr Ala Gly Asn Arg Ile Asn Phe Pro Ser Tyr
            325                 330                 335

Gly Val Phe Asn Pro Gly Gly Ala Ile Trp Ile Ala Asp Glu Asp Pro
            340                 345                 350

Arg Pro Phe Tyr Arg Thr Leu Ser Asp Pro Val Phe Val Arg Gly Gly
        355                 360                 365

Phe Gly Asn Pro His Tyr Val Leu Gly Leu Arg Gly Val Ala Phe Gln
    370                 375                 380

Gln Thr Gly Thr Asn His Thr Arg Thr Phe Arg Asn Ser Gly Thr Ile
385                 390                 395                 400

Asp Ser Leu Asp Glu Ile Pro Pro Gln Asp Asn Ser Gly Ala Pro Trp
            405                 410                 415

Asn Asp Tyr Ser His Val Leu Asn His Val Thr Phe Val Arg Trp Pro
        420                 425                 430

Gly Glu Ile Ser Gly Ser Asp Ser Trp Arg Ala Pro Met Phe Ser Trp
    435                 440                 445

Thr His Arg Ser Ala Thr Pro Thr Asn Thr Ile Asp Pro Glu Arg Ile
450                 455                 460

Thr Gln Ile Pro Leu Val Lys Ala His Thr Leu Gln Ser Gly Thr Thr
465                 470                 475                 480

Val Val Arg Gly Pro Gly Phe Thr Gly Gly Asp Ile Leu Arg Arg Thr
            485                 490                 495

Ser Gly Gly Pro Phe Ala Tyr Thr Ile Val Asn Ile Asn Gly Gln Leu
        500                 505                 510

Pro Gln Arg Tyr Arg Ala Arg Ile Arg Tyr Ala Ser Thr Thr Asn Leu
    515                 520                 525

Arg Ile Tyr Val Thr Val Ala Gly Glu Arg Ile Phe Ala Gly Gln Phe
    530                 535                 540

Asn Lys Thr Met Asp Thr Gly Asp Pro Leu Thr Phe Gln Ser Phe Ser
545                 550                 555                 560

Tyr Ala Thr Ile Asn Thr Ala Phe Thr Phe Pro Met Ser Gln Ser Ser
            565                 570                 575

Phe Thr Val Gly Ala Asp Thr Phe Ser Ser Gly Asn Glu Val Tyr Ile
            580                 585                 590

Asp Arg Phe Glu Leu Ile Pro Val Thr Ala Thr Phe Glu Ala Glu Tyr
        595                 600                 605
```

-continued

```
Asp  Leu  Glu  Arg  Ala  Gln  Lys  Ala  Val  Asn  Ala  Leu  Phe  Thr  Ser  Ile
     610                 615                 620

Asn  Gln  Ile  Gly  Ile  Lys  Thr  Asp  Val  Thr  Asp  Tyr  His  Ile  Asp  Gln
625                      630                 635                           640

Val  Ser  Asn  Leu  Val  Asp  Cys  Leu  Ser  Asp  Glu  Phe  Cys  Leu  Asp  Glu
                    645                 650                           655

Lys  Arg  Glu  Leu  Ser  Glu  Lys  Val  Lys  His  Ala  Lys  Arg  Leu  Ser  Asp
               660                 665                      670

Glu  Arg  Asn  Leu  Leu  Gln  Asp  Pro  Asn  Phe  Lys  Gly  Ile  Asn  Arg  Gln
          675                 680                      685

Leu  Asp  Arg  Gly  Trp  Arg  Gly  Ser  Thr  Asp  Ile  Thr  Ile  Gln  Arg  Gly
     690                 695                 700

Asp  Asp  Val  Phe  Lys  Glu  Asn  Tyr  Val  Thr  Leu  Pro  Gly  Thr  Phe  Asp
705                      710                 715                           720

Glu  Cys  Tyr  Pro  Thr  Tyr  Leu  Tyr  Gln  Lys  Ile  Asp  Glu  Ser  Lys  Leu
                    725                 730                           735

Lys  Pro  Tyr  Thr  Arg  Tyr  Gln  Leu  Arg  Gly  Tyr  Ile  Glu  Asp  Ser  Gln
               740                 745                      750

Asp  Leu  Glu  Ile  Tyr  Leu  Ile  Arg  Tyr  Asn  Ala  Lys  His  Glu  Thr  Val
          755                 760                      765

Asn  Val  Leu  Gly  Thr  Gly  Ser  Leu  Trp  Pro  Leu  Ser  Val  Gln  Ser  Pro
770                      775                 780

Ile  Arg  Lys  Cys  Gly  Glu  Pro  Asn  Arg  Cys  Ala  Pro  His  Leu  Glu  Trp
785                      790                 795                           800

Asn  Pro  Asp  Leu  Asp  Cys  Ser  Cys  Arg  Asp  Gly  Glu  Lys  Cys  Ala  His
                    805                 810                           815

His  Ser  His  His  Phe  Ser  Leu  Asp  Ile  Asp  Val  Gly  Cys  Thr  Asp  Leu
               820                 825                      830

Asn  Glu  Asp  Leu  Asp  Val  Trp  Val  Ile  Phe  Lys  Ile  Lys  Thr  Gln  Asp
          835                 840                      845

Gly  His  Ala  Arg  Leu  Gly  Asn  Leu  Glu  Phe  Leu  Glu  Glu  Lys  Pro  Leu
     850                 855                 860

Val  Gly  Glu  Ala  Leu  Ala  Arg  Val  Lys  Arg  Ala  Glu  Lys  Lys  Trp  Arg
865                      870                 875                           880

Asp  Lys  Arg  Glu  Lys  Leu  Glu  Leu  Glu  Thr  Asn  Ile  Val  Tyr  Lys  Glu
               885                 890                      895

Ala  Lys  Glu  Ser  Val  Asp  Ala  Leu  Phe  Val  Asn  Ser  Gln  Tyr  Asp  Gln
               900                 905                      910

Leu  Gln  Ala  Asp  Thr  Asn  Ile  Ala  Met  Ile  His  Ala  Ala  Asp  Lys  Arg
          915                 920                      925

Val  His  Arg  Ile  Arg  Glu  Ala  Tyr  Leu  Pro  Glu  Leu  Ser  Val  Ile  Pro
     930                 935                 940

Gly  Val  Asn  Val  Asp  Ile  Phe  Glu  Glu  Leu  Lys  Gly  Arg  Ile  Phe  Thr
945                      950                 955                           960

Ala  Phe  Phe  Leu  Tyr  Asp  Ala  Arg  Asn  Val  Ile  Lys  Asn  Gly  Asp  Phe
                    965                 970                           975

Asn  Asn  Gly  Leu  Ser  Cys  Trp  Asn  Val  Lys  Gly  His  Val  Asp  Val  Glu
               980                 985                      990

Glu  Gln  Asn  Asn  His  Arg  Ser  Val  Leu  Val  Val  Pro  Glu  Trp  Glu  Ala
          995                 1000                    1005

Glu  Val  Ser  Gln  Glu  Val  Arg  Val  Cys  Pro  Gly  Arg  Gly  Tyr  Ile  Leu
     1010                1015                1020

Arg  Val  Thr  Ala  Tyr  Lys  Glu  Gly  Tyr  Gly  Glu  Gly  Cys  Val  Thr  Ile
```

|   |   |   |   |   |   |   |   |   |   |   |   |   |   |   |
|---|---|---|---|---|---|---|---|---|---|---|---|---|---|---|
| 1025 | | | | 1030 | | | | 1035 | | | | 1040 | | |
| His | Glu | Ile | Glu | Asn | Asn | Thr | Asp | Glu | Leu | Lys | Phe | Ser | Asn | Cys | Val |
| | | | | 1045 | | | | 1050 | | | | | | 1055 | |
| Glu | Glu | Glu | Val | Tyr | Pro | Asn | Asn | Thr | Val | Thr | Cys | Asn | Asp | Tyr | Thr |
| | | | | 1060 | | | | 1065 | | | | | | 1070 | |
| Ala | Asn | Gln | Glu | Glu | Tyr | Gly | Gly | Ala | Tyr | Thr | Ser | Arg | Asn | Arg | Gly |
| | | | | 1075 | | | | 1080 | | | | | | 1085 | |
| Tyr | Asp | Glu | Thr | Tyr | Gly | Ser | Asn | Ser | Ser | Val | Pro | Ala | Asp | Tyr | Ala |
| | | | | 1090 | | | | 1095 | | | | 1100 | | | |
| Ser | Val | Tyr | Glu | Glu | Lys | Ser | Tyr | Thr | Asp | Gly | Arg | Arg | Asp | Asn | Pro |
| 1105 | | | | | | 1110 | | | | 1115 | | | | | 1120 |
| Cys | Glu | Ser | Asn | Arg | Gly | Tyr | Gly | Asp | Tyr | Thr | Pro | Leu | Pro | Ala | Gly |
| | | | | 1125 | | | | 1130 | | | | | | 1135 | |
| Tyr | Val | Thr | Lys | Glu | Leu | Glu | Tyr | Phe | Pro | Glu | Thr | Asp | Lys | Val | Trp |
| | | | | 1140 | | | | 1145 | | | | | | 1150 | |
| Ile | Glu | Ile | Gly | Glu | Thr | Glu | Gly | Thr | Phe | Ile | Val | Asp | Ser | Val | Glu |
| | | | | 1155 | | | | 1160 | | | | | | 1165 | |
| Leu | Leu | Leu | Met | Glu | Glu |
| | | | | 1170 | |

(2) INFORMATION FOR SEQ ID NO:26:

(i) SEQUENCE CHARACTERISTICS:
        (A) LENGTH: 3444 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

```
ATGGAAAATA ATATTCAAAA TCAATGCGTA CCTTACAATT GTTTAAATAA TCCTGAAGTA      60
GAAATACTGA ACGAAGAACG CAGCACCGGC CGCCTGCCGC TGGACATCAG CCTGAGCCTT     120
ACACGTTTCC TTTTGAGTGA ATTTGTTCCA GGTGTGGGAG TTGCGTTTGG ATTATTTGAT     180
TTAATATGGG GTTTTATAAC TCCTTCTGAT TGGAGCTTAT TTCTTTTACA GATTGAACAA     240
TTGATTGAGC AAAGAATAGA AACATTGGAA AGGAACCGGG CAATTACTAC ATTACGAGGG     300
TTAGCAGATA GCTATGAAAT TTATATTGAA GCACTAAGAG AGTGGGAAGC AAATCCTAAT     360
AATGCACAAT TAAGGGAAGA TGTGCGTATT CGATTGCTA ATACAGACGA CGCTTTAATA     420
ACAGCAATAA ATAATTTTAC ACTTACAAGT TTTGAAATCC CTCTTTTATC GGTCTATGTT     480
CAAGCGGCGA ATTTACATTT ATCACTATTA GAGACGCTG TATCGTTTGG GCAGGGTTGG     540
GGACTGGATA TAGCTACTGT TAATAATCAT TATAATAGAT TAATAAATCT TATTCATAGA     600
TATACGAAAC ATTGTTTGGA CACATACAAT CAAGGATTAG AAAACTAAG AGGTACTAAT      660
ACTCGACAAT GGGCAAGATT CAATCAGTTT AGGAGAGATT TAACACTTAC TGTATTAGAT     720
ATCGTTGCTC TTTTTCCGAA CTACGATGTT AGAACATATC CAATTCAAAC GTCATCCAA      780
TTAACAAGGG AAATTTATAC AAGTTCAGTA ATTGAGGATT CTCCAGTTTC TGCTAATATA     840
CCTAATGGTT TTAATAGGGC GGAATTTGGA GTTAGACCGC CCATCTTAT GGACTTTATG      900
AATTCTTTGT TTGTAACTGC AGAGACTGTT AGAAGTCAAA CTGTGTGGGG AGGACACTTA     960
GTTAGTTCAC GAAATACGGC TGGTAACCGT ATAAATTTCC CTAGTTACGG GGTCTTCAAT    1020
CCTGGTGGCG CCATTTGGAT TGCAGATGAG GATCCACGTC CTTTTATCG GACATTATCA     1080
GATCCTGTTT TTGTCCGAGG AGGATTTGGG AATCCTCATT ATGTACTGGG GCTTAGGGGA    1140
```

-continued

```
GTAGCATTTC AACAAACTGG TACGAACCAC ACCCGAACAT TTAGAAATAG TGGGACCATA    1200
GATTCTCTAG ATGAAATCCC ACCTCAGGAT AATAGTGGGG CACCTTGGAA TGATTATAGT    1260
CATGTATTAA ATCATGTTAC ATTTGTACGA TGGCCAGGTG AGATTTCAGG AAGTGATTCA    1320
TGGAGAGCTC CAATGTTTTC TTGGACGCAC CGTAGTGCAA CCCCTACAAA TACAATTGAT    1380
CCGGAGAGGA TTACTCAAAT ACCATGGTA AAAGCACATA CACTTCAGTC AGGTACTACT     1440
GTTGTAAGAG GGCCCGGGTT TACGGGAGGA GATATTCTTC GACGAACAAG TGGAGGACCA    1500
TTTGCTTATA CTATTGTTAA TATAAATGGG CAATTACCCC AAAGGTATCG TGCAAGAATA    1560
CGCTATGCCT CTACTACAAA TCTAAGAATT TACGTAACGG TTGCAGGTGA ACGGATTTTT    1620
GCTGGTCAAT TTAACAAAAC AATGGATACC GGTGACCCAT TAACATTCCA ATCTTTTAGT    1680
TACGCAACTA TTAATACAGC TTTTACATTC CCAATGAGCC AGAGTAGTTT CACAGTAGGT    1740
GCTGATACTT TTAGTTCAGG GAATGAAGTT TATATAGACA GATTTGAATT GATTCCAGTT    1800
ACTGCAACAT TTGAAGCAGA ATATGATTTA GAAAGAGCAC AAAAGGCGGT GAATGCGCTG    1860
TTTACTTCTA TAAACCAAAT AGGGATAAAA ACAGATGTGA CGGATTATCA TATCGATCGA    1920
GTATCCAATT TAGTTGAGTG TTTATCTGAT GAATTTTGTC TGGATGAAAA AAAAGAATTG    1980
TCCGAGAAAG TCAAACATGC GAAGCGACTT AGTGATGAGC GGAATTTACT TCAAGATCCA    2040
AACTTTAGAG GGATCAATAG ACAACTAGAC CGTGGCTGGA GAGGAAGTAC GGATATTACC    2100
ATCCAAGGAG GCGATGACGT ATTCAAAGAG AATTACGTTA CGCTATTGGG TACCTTTGAT    2160
GAGTGCTATC CAACGTATTT ATATCAAAAA ATAGATGAGT CGAAATTAAA AGCCTATACC    2220
CGTTACCAAT TAAGAGGGTA TATCGAAGAT AGTCAAGACT TAGAAATCTA TTTAATTCGC    2280
TACAATGCCA AACACGAAAC AGTAAATGTG CCAGGTACGG GTTCCTTATG GCCGCTTTCA    2340
GCCCCAAGTC CAATCGGAAA ATGTGCCCAT CATTCCCATC ATTTCTCCTT GGACATTGAT    2400
GTTGGATGTA CAGACTTAAA TGAGGACTTA GGTGTATGGG TGATATTCAA GATTAAGACG    2460
CAAGATGGCC ATGCAAGACT AGGAAATCTA GAATTTCTCG AAGAGAAACC ATTAGTAGGA    2520
GAAGCACTAG CTCGTGTGAA AAGAGCGGAG AAAAAATGGA GAGACAAACG TGAAAAATTG    2580
GAATGGGAAA CAAATATTGT TTATAAAGAG GCAAAGAATT CTGTAGATGC TTTATTTGTA    2640
AACTCTCAAT ATGATAGATT ACAAGCGGAT ACCAACATCG CGATGATTCA TGCGGCAGAT    2700
AAACGCGTTC ATAGCATTCG AGAAGCTTAT CTGCCTGAGC TGTCTGTGAT TCCGGGTGTC    2760
AATGCGGCTA TTTTTGAAGA ATTAGAAGGG CGTATTTTCA CTGCATTCTC CCTATATGAT    2820
GCGAGAAATG TCATTAAAAA TGGTGATTTT AATAATGGCT TATCCTGCTG GAACGTGAAA    2880
GGGCATGTAG ATGTAGAAGA ACAAAACAAC CACCGTTCGG TCCTTGTTGT TCCGGAATGG    2940
GAAGCAGAAG TGTCACAAGA AGTTCGTGTC TGTCCGGGTC GTGGCTATAT CCTTCGTGTC    3000
ACAGCGTACA AGGAGGGATA TGGAGAAGGT TGCGTAACCA TCATGAGAT CGAGAACAAT     3060
ACAGACGAAC TGAAGTTTAG CAACTGTGTA GAAGAGGAAG TATATCCAAA CAACACGGTA    3120
ACGTGTAATG ATTATACTGC GACTCAAGAA GAATATGAGG GTACGTACAC TTCTCGTAAT    3180
CGAGGATATG ACGGAGCCTA TGAAAGCAAT TCTTCTGTAC CAGCTGATTA TGCATCAGCC    3240
TATGAAGAAA AAGCATATAC AGATGGACGA AGAGACAATC CTTGTGAATC TAACAGAGGA    3300
TATGGGGATT ACACACCACT ACCAGCTGGC TATGTGACAA AAGAATTAGA GTACTTCCCA    3360
GAAACCGATA AGGTATGGAT TGAGATCGGA GAAACGGAAG GAACATTCAT CGTGGACAGC    3420
GTGGAATTAC TTCTTATGGA GGAA                                          3444
```

( 2 ) INFORMATION FOR SEQ ID NO:27:

( i ) SEQUENCE CHARACTERISTICS:
    ( A ) LENGTH: 1148 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:27:

```
Met Glu Asn Asn Ile Gln Asn Gln Cys Val Pro Tyr Asn Cys Leu Asn
 1               5                  10                  15
Asn Pro Glu Val Glu Ile Leu Asn Glu Glu Arg Ser Thr Gly Arg Leu
            20                  25                  30
Pro Leu Asp Ile Ser Leu Ser Leu Thr Arg Phe Leu Leu Ser Glu Phe
        35                  40                  45
Val Pro Gly Val Gly Val Ala Phe Gly Leu Phe Asp Leu Ile Trp Gly
    50                  55                  60
Phe Ile Thr Pro Ser Asp Trp Ser Leu Phe Leu Leu Gln Ile Glu Gln
65                  70                  75                  80
Leu Ile Glu Gln Arg Ile Glu Thr Leu Glu Arg Asn Arg Ala Ile Thr
                85                  90                  95
Thr Leu Arg Gly Leu Ala Asp Ser Tyr Glu Ile Tyr Ile Glu Ala Leu
            100                 105                 110
Arg Glu Trp Glu Ala Asn Pro Asn Asn Ala Gln Leu Arg Glu Asp Val
        115                 120                 125
Arg Ile Arg Phe Ala Asn Thr Asp Asp Ala Leu Ile Thr Ala Ile Asn
130                 135                 140
Asn Phe Thr Leu Thr Ser Phe Glu Ile Pro Leu Leu Ser Val Tyr Val
145                 150                 155                 160
Gln Ala Ala Asn Leu His Leu Ser Leu Leu Arg Asp Ala Val Ser Phe
                165                 170                 175
Gly Gln Gly Trp Gly Leu Asp Ile Ala Thr Val Asn Asn His Tyr Asn
            180                 185                 190
Arg Leu Ile Asn Leu Ile His Arg Tyr Thr Lys His Cys Leu Asp Thr
        195                 200                 205
Tyr Asn Gln Gly Leu Glu Asn Leu Arg Gly Thr Asn Thr Arg Gln Trp
210                 215                 220
Ala Arg Phe Asn Gln Phe Arg Arg Asp Leu Thr Leu Thr Val Leu Asp
225                 230                 235                 240
Ile Val Ala Leu Phe Pro Asn Tyr Asp Val Arg Thr Tyr Pro Ile Gln
                245                 250                 255
Thr Ser Ser Gln Leu Thr Arg Glu Ile Tyr Thr Ser Ser Val Ile Glu
            260                 265                 270
Asp Ser Pro Val Ser Ala Asn Ile Pro Asn Gly Phe Asn Arg Ala Glu
        275                 280                 285
Phe Gly Val Arg Pro Pro His Leu Met Asp Phe Met Asn Ser Leu Phe
290                 295                 300
Val Thr Ala Glu Thr Val Arg Ser Gln Thr Val Trp Gly Gly His Leu
305                 310                 315                 320
Val Ser Ser Arg Asn Thr Ala Gly Asn Arg Ile Asn Phe Pro Ser Tyr
                325                 330                 335
Gly Val Phe Asn Pro Gly Gly Ala Ile Trp Ile Ala Asp Glu Asp Pro
            340                 345                 350
Arg Pro Phe Tyr Arg Thr Leu Ser Asp Pro Val Phe Val Arg Gly Gly
        355                 360                 365
```

```
Phe  Gly  Asn  Pro  His  Tyr  Val  Leu  Gly  Leu  Arg  Gly  Val  Ala  Phe  Gln
     370                 375                      380

Gln  Thr  Gly  Thr  Asn  His  Thr  Arg  Thr  Phe  Arg  Asn  Ser  Gly  Thr  Ile
385                      390                      395                      400

Asp  Ser  Leu  Asp  Glu  Ile  Pro  Pro  Gln  Asp  Asn  Ser  Gly  Ala  Pro  Trp
               405                      410                           415

Asn  Asp  Tyr  Ser  His  Val  Leu  Asn  His  Val  Thr  Phe  Val  Arg  Trp  Pro
               420                 425                           430

Gly  Glu  Ile  Ser  Gly  Ser  Asp  Ser  Trp  Arg  Ala  Pro  Met  Phe  Ser  Trp
          435                 440                      445

Thr  His  Arg  Ser  Ala  Thr  Pro  Thr  Asn  Thr  Ile  Asp  Pro  Glu  Arg  Ile
     450                 455                           460

Thr  Gln  Ile  Pro  Leu  Val  Lys  Ala  His  Thr  Leu  Gln  Ser  Gly  Thr  Thr
465                      470                      475                      480

Val  Val  Arg  Gly  Pro  Gly  Phe  Thr  Gly  Gly  Asp  Ile  Leu  Arg  Arg  Thr
                    485                      490                           495

Ser  Gly  Gly  Pro  Phe  Ala  Tyr  Thr  Ile  Val  Asn  Ile  Asn  Gly  Gln  Leu
               500                 505                      510

Pro  Gln  Arg  Tyr  Arg  Ala  Arg  Ile  Arg  Tyr  Ala  Ser  Thr  Asn  Leu
          515                      520                      525

Arg  Ile  Tyr  Val  Thr  Val  Ala  Gly  Glu  Arg  Ile  Phe  Ala  Gly  Gln  Phe
     530                      535                      540

Asn  Lys  Thr  Met  Asp  Thr  Gly  Asp  Pro  Leu  Thr  Phe  Gln  Ser  Phe  Ser
545                      550                      555                      560

Tyr  Ala  Thr  Ile  Asn  Thr  Ala  Phe  Thr  Phe  Pro  Met  Ser  Gln  Ser  Ser
               565                      570                      575

Phe  Thr  Val  Gly  Ala  Asp  Thr  Phe  Ser  Ser  Gly  Asn  Glu  Val  Tyr  Ile
               580                      585                      590

Asp  Arg  Phe  Glu  Leu  Ile  Pro  Val  Thr  Ala  Thr  Phe  Glu  Ala  Glu  Tyr
          595                      600                      605

Asp  Leu  Glu  Arg  Ala  Gln  Lys  Ala  Val  Asn  Ala  Leu  Phe  Thr  Ser  Ile
610                      615                      620

Asn  Gln  Ile  Gly  Ile  Lys  Thr  Asp  Val  Thr  Asp  Tyr  His  Ile  Asp  Arg
625                      630                      635                      640

Val  Ser  Asn  Leu  Val  Glu  Cys  Leu  Ser  Asp  Glu  Phe  Cys  Leu  Asp  Glu
                    645                      650                      655

Lys  Lys  Glu  Leu  Ser  Glu  Lys  Val  Lys  His  Ala  Lys  Arg  Leu  Ser  Asp
               660                      665                      670

Glu  Arg  Asn  Leu  Leu  Gln  Asp  Pro  Asn  Phe  Arg  Gly  Ile  Asn  Arg  Gln
          675                      680                      685

Leu  Asp  Arg  Gly  Trp  Arg  Gly  Ser  Thr  Asp  Ile  Thr  Ile  Gln  Gly  Gly
     690                      695                      700

Asp  Asp  Val  Phe  Lys  Glu  Asn  Tyr  Val  Thr  Leu  Leu  Gly  Thr  Phe  Asp
705                      710                      715                      720

Glu  Cys  Tyr  Pro  Thr  Tyr  Leu  Tyr  Gln  Lys  Ile  Asp  Glu  Ser  Lys  Leu
               725                      730                      735

Lys  Ala  Tyr  Thr  Arg  Tyr  Gln  Leu  Arg  Gly  Tyr  Ile  Glu  Asp  Ser  Gln
               740                      745                      750

Asp  Leu  Glu  Ile  Tyr  Leu  Ile  Arg  Tyr  Asn  Ala  Lys  His  Glu  Thr  Val
          755                      760                      765

Asn  Val  Pro  Gly  Thr  Gly  Ser  Leu  Trp  Pro  Leu  Ser  Ala  Pro  Ser  Pro
     770                      775                      780

Ile  Gly  Lys  Cys  Ala  His  His  Ser  His  His  Phe  Ser  Leu  Asp  Ile  Asp
785                      790                      795                      800
```

-continued

| | | | | | | | | | | | | | | |
|---|---|---|---|---|---|---|---|---|---|---|---|---|---|---|
| Val | Gly | Cys | Thr | Asp<br>805 | Leu | Asn | Glu | Asp<br>810 | Leu | Gly | Val | Trp | Val<br>815 | Ile | Phe |
| Lys | Ile | Lys | Thr<br>820 | Gln | Asp | Gly | His | Ala<br>825 | Arg | Leu | Gly | Asn | Leu<br>830 | Glu | Phe |
| Leu | Glu | Glu<br>835 | Lys | Pro | Leu | Val | Gly<br>840 | Glu | Ala | Leu | Ala | Arg<br>845 | Val | Lys | Arg |
| Ala | Glu<br>850 | Lys | Lys | Trp | Arg | Asp<br>855 | Lys | Arg | Glu | Lys | Leu<br>860 | Glu | Trp | Glu | Thr |
| Asn<br>865 | Ile | Val | Tyr | Lys | Glu<br>870 | Ala | Lys | Glu | Ser | Val<br>875 | Asp | Ala | Leu | Phe | Val<br>880 |
| Asn | Ser | Gln | Tyr | Asp<br>885 | Arg | Leu | Gln | Ala | Asp<br>890 | Thr | Asn | Ile | Ala | Met<br>895 | Ile |
| His | Ala | Ala | Asp<br>900 | Lys | Arg | Val | His | Ser<br>905 | Ile | Arg | Glu | Ala | Tyr<br>910 | Leu | Pro |
| Glu | Leu | Ser<br>915 | Val | Ile | Pro | Gly | Val<br>920 | Asn | Ala | Ala | Ile | Phe<br>925 | Glu | Glu | Leu |
| Glu | Gly<br>930 | Arg | Ile | Phe | Thr | Ala<br>935 | Phe | Ser | Leu | Tyr | Asp<br>940 | Ala | Arg | Asn | Val |
| Ile<br>945 | Lys | Asn | Gly | Asp | Phe<br>950 | Asn | Asn | Gly | Leu | Ser<br>955 | Cys | Trp | Asn | Val | Lys<br>960 |
| Gly | His | Val | Asp | Val<br>965 | Glu | Glu | Gln | Asn | Asn<br>970 | His | Arg | Ser | Val | Leu<br>975 | Val |
| Val | Pro | Glu<br>980 | Trp | Glu | Ala | Glu | Val<br>985 | Ser | Gln | Glu | Val | Arg<br>990 | Val | Cys | Pro |
| Gly | Arg | Gly<br>995 | Tyr | Ile | Leu | Arg | Val<br>1000 | Thr | Ala | Tyr | Lys | Glu<br>1005 | Gly | Tyr | Gly |
| Glu | Gly<br>1010 | Cys | Val | Thr | Ile | His<br>1015 | Glu | Ile | Glu | Asn | Asn<br>1020 | Thr | Asp | Glu | Leu |
| Lys<br>1025 | Phe | Ser | Asn | Cys | Val<br>1030 | Glu | Glu | Val | Tyr | Pro<br>1035 | Asn | Asn | Thr | Val<br>1040 |
| Thr | Cys | Asn | Asp | Tyr<br>1045 | Thr | Ala | Thr | Gln | Glu<br>1050 | Glu | Tyr | Glu | Gly | Thr<br>1055 | Tyr |
| Thr | Ser | Arg | Asn<br>1060 | Arg | Gly | Tyr | Asp | Gly<br>1065 | Ala | Tyr | Glu | Ser | Asn<br>1070 | Ser | Ser |
| Val | Pro | Ala<br>1075 | Asp | Tyr | Ala | Ser | Ala<br>1080 | Tyr | Glu | Glu | Lys | Ala<br>1085 | Tyr | Thr | Asp |
| Gly | Arg | Arg<br>1090 | Asp | Asn | Pro | Cys | Glu<br>1095 | Ser | Asn | Arg | Gly | Tyr<br>1100 | Gly | Asp | Tyr |
| Thr | Pro<br>1105 | Leu | Pro | Ala | Gly | Tyr<br>1110 | Val | Thr | Lys | Glu | Leu<br>1115 | Glu | Tyr | Phe | Pro<br>1120 |
| Glu | Thr | Asp | Lys | Val<br>1125 | Trp | Ile | Glu | Ile | Gly<br>1130 | Glu | Thr | Glu | Gly | Thr<br>1135 | Phe |
| Ile | Val | Asp | Ser | Val<br>1140 | Glu | Leu | Leu | Leu | Met<br>1145 | Glu | Glu | | | | |

( 2 ) INFORMATION FOR SEQ ID NO:28:

( i ) SEQUENCE CHARACTERISTICS:
        ( A ) LENGTH: 3522 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

-continued

| | | | | | | |
|---|---|---|---|---|---|---|
| ATGGAAAATA | ATATTCAAAA | TCAATGCGTA | CCTTACAATT | GTTTAAATAA | TCCTGAAGTA | 60 |
| GAAATACTGA | ACGAAGAACG | CAGCACCGGC | CGCCTGCCGC | TGGACATCAG | CCTGAGCCTT | 120 |
| ACACGTTTCC | TTTTGAGTGA | ATTTGTTCCA | GGTGTGGGAG | TTGCGTTTGG | ATTATTTGAT | 180 |
| TTAATATGGG | GTTTTATAAC | TCCTTCTGAT | TGGAGCTTAT | TTCTTTTACA | GATTGAACAA | 240 |
| TTGATTGAGC | AAAGAATAGA | AACATTGGAA | AGGAACCGGG | CAATTACTAC | ATTACGAGGG | 300 |
| TTAGCAGATA | GCTATGAAAT | TTATATTGAA | GCACTAAGAG | AGTGGGAAGC | AAATCCTAAT | 360 |
| AATGCACAAT | TAAGGGAAGA | TGTGCGTATT | CGATTGCTA | ATACAGACGA | CGCTTTAATA | 420 |
| ACAGCAATAA | ATAATTTTAC | ACTTACAAGT | TTTGAAATCC | CTCTTTTATC | GGTCTATGTT | 480 |
| CAAGCGGCGA | ATTTACATTT | ATCACTATTA | AGAGACGCTG | TATCGTTTGG | GCAGGGTTGG | 540 |
| GGACTGGATA | TAGCTACTGT | TAATAATCAT | TATAATAGAT | TAATAAATCT | TATTCATAGA | 600 |
| TATACGAAAC | ATTGTTTGGA | CACATACAAT | CAAGGATTAG | AAAACTTAAG | AGGTACTAAT | 660 |
| ACTCGACAAT | GGGCAAGATT | CAATCAGTTT | AGGAGAGATT | TAACACTTAC | TGTATTAGAT | 720 |
| ATCGTTGCTC | TTTTTCCGAA | CTACGATGTT | AGAACATATC | CAATTCAAAC | GTCATCCCAA | 780 |
| TTAACAAGGG | AAATTTATAC | AAGTTCAGTA | ATTGAGGATT | CTCCAGTTTC | TGCTAATATA | 840 |
| CCTAATGGTT | TTAATAGGGC | GGAATTTGGA | GTTAGACCGC | CCCATCTTAT | GGACTTTATG | 900 |
| AATTCTTTGT | TTGTAACTGC | AGAGACTGTT | AGAAGTCAAA | CTGTGTGGGG | AGGACACTTA | 960 |
| GTTAGTTCAC | GAAATACGGC | TGGTAACCGT | ATAAATTTCC | CTAGTTACGG | GGTCTTCAAT | 1020 |
| CCTGGTGGCG | CCATTTGGAT | TGCAGATGAG | GATCCACGTC | CTTTTATCG | GACATTATCA | 1080 |
| GATCCTGTTT | TTGTCCGAGG | AGGATTTGGG | AATCCTCATT | ATGTACTGGG | GCTTAGGGGA | 1140 |
| GTAGCATTTC | AACAAACTGG | TACGAACCAC | ACCCGAACAT | TTAGAAATAG | TGGGACCATA | 1200 |
| GATTCTCTAG | ATGAAATCCC | ACCTCAGGAT | AATAGTGGGG | CACCTTGGAA | TGATTATAGT | 1260 |
| CATGTATTAA | ATCATGTTAC | ATTTGTACGA | TGGCCAGGTG | AGATTTCAGG | AAGTGATTCA | 1320 |
| TGGAGAGCTC | CAATGTTTTC | TTGGACGCAC | CGTAGTGCAA | CCCCTACAAA | TACAATTGAT | 1380 |
| CCGGAGAGGA | TTACTCAAAT | ACCATTGGTA | AAAGCACATA | CACTTCAGTC | AGGTACTACT | 1440 |
| GTTGTAAGAG | GGCCCGGGTT | TACGGGAGGA | GATATTCTTC | GACGAACAAG | TGGAGGACCA | 1500 |
| TTTGCTTATA | CTATTGTTAA | TATAAATGGG | CAATTACCCC | AAAGGTATCG | TGCAAGAATA | 1560 |
| CGCTATGCCT | CTACTACAAA | TCTAAGAATT | TACGTAACGG | TTGCAGGTGA | ACGGATTTTT | 1620 |
| GCTGGTCAAT | TTAACAAAAC | AATGGATACC | GGTGACCCAT | TAACATTCCA | ATCTTTTAGT | 1680 |
| TACGCAACTA | TTAATACAGC | TTTTACATTC | CCAATGAGCC | AGAGTAGTTT | CACAGTAGGT | 1740 |
| GCTGATACTT | TTAGTTCAGG | GAATGAAGTT | TATATAGACA | GATTTGAATT | GATTCCAGTT | 1800 |
| ACTGCAACAT | TTGAAGCAGA | ATATGATTTA | GAAAGAGCAC | AAAAGGCGGT | GAATGCGCTG | 1860 |
| TTTACTTCTA | TAAACCAAAT | AGGGATAAAA | ACAGATGTGA | CGGATTATCA | TATCGATCGA | 1920 |
| GTGTCCAATT | TAGTTACGTA | TTTATCGGAT | GAATTTTGTC | TGGATGAAAA | GCGAGAATTG | 1980 |
| TCCGAGAAAG | TCAAACATGC | GAAGCGACTC | AGTGATGAAC | GCAATTTACT | CCAAGATTCA | 2040 |
| AATTTCAAAG | ACATTAATAG | GCAACCAGAA | CGTGGGTGGG | GCGGAAGTAC | AGGGATTACC | 2100 |
| ATCCAAGGAG | GGGATGACGT | ATTTAAAGAA | AATTACGTCA | CACTATCAGG | TACCTTTGAT | 2160 |
| GAGTGCTATC | CAACATATTT | GTATCAAAAA | ATCGATGAAT | CAAAATTAAA | AGCCTTTACC | 2220 |
| CGTTATCAAT | TAAGAGGGTA | TATCGAAGAT | AGTCAAGACT | TAGAAATCTA | TTTAATTCGC | 2280 |
| TACAATGCAA | AACATGAAAC | AGTAAATGTG | CCAGGTACGG | GTTCCTTATG | GCCGCTTTCA | 2340 |
| GCCCAAAGTC | CAATCGGAAA | GTGTGGAGAG | CCGAATCGAT | GCGCGCCACA | CCTTGAATGG | 2400 |

-continued

| | | | | | |
|---|---|---|---|---|---|
| AATCCTGACT | TAGATTGTTC | GTGTAGGGAT | GGAGAAAAGT | GTGCCCATCA | TTCGCATCAT | 2460 |
| TTCTCCTTAG | ACATTGATGT | AGGATGTACA | GACTTAAATG | AGGACCTAGG | TGTATGGGTG | 2520 |
| ATCTTTAAGA | TTAAGACGCA | AGATGGGCAC | GCAAGACTAG | GGAATCTAGA | GTTTCTCGAA | 2580 |
| GAGAAACCAT | TAGTAGGAGA | AGCGCTAGCT | CGTGTGAAAA | GAGCGGAGAA | AAAATGGAGA | 2640 |
| GACAAACGTG | AAAAATTGGA | ATGGGAAACA | AATATCGTTT | ATAAAGAGGC | AAAAGAATCT | 2700 |
| GTAGATGCTT | TATTTGTAAA | CTCTCAATAT | GATCAATTAC | AAGCGGATAC | GAATATTGCC | 2760 |
| ATGATTCATG | CGGCAGATAA | ACGTGTTCAT | AGCATTCGAG | AAGCTTATCT | GCCTGAGCTG | 2820 |
| TCTGTGATTC | CGGGTGTCAA | TGCGGCTATT | TTTGAAGAAT | TAGAAGGGCG | TATTTTCACT | 2880 |
| GCATTCTCCC | TATATGATGC | GAGAAATGTC | ATTAAAAATG | GTGATTTTAA | TAATGGCTTA | 2940 |
| TCCTGCTGGA | ACGTGAAAGG | GCATGTAGAT | GTAGAAGAAC | AAAACAACCA | CCGTTCGGTC | 3000 |
| CTTGTTGTTC | CGGAATGGGA | AGCAGAAGTG | TCACAAGAAG | TTCGTGTCTG | TCCGGGTCGT | 3060 |
| GGCTATATCC | TTCGTGTCAC | AGCGTACAAG | GAGGGATATG | GAGAAGGTTG | CGTAACCATT | 3120 |
| CATGAGATCG | AGAACAATAC | AGACGAACTG | AAGTTTAGCA | ACTGTGTAGA | AGAGGAAGTA | 3180 |
| TATCCAAACA | ACACGGTAAC | GTGTAATGAT | TATACTGCGA | CTCAAGAAGA | ATATGAGGGT | 3240 |
| ACGTACACTT | CTCGTAATCG | AGGATATGAC | GGAGCCTATG | AAAGCAATTC | TTCTGTACCA | 3300 |
| GCTGATTATG | CATCAGCCTA | TGAAGAAAAA | GCATATACAG | ATGGACGAAG | AGACAATCCT | 3360 |
| TGTGAATCTA | ACAGAGGATA | TGGGGATTAC | ACACCACTAC | CAGCTGGCTA | TGTGACAAAA | 3420 |
| GAATTAGAGT | ACTTCCCAGA | AACCGATAAG | GTATGGATTG | AGATCGGAGA | AACGGAAGGA | 3480 |
| ACATTCATCG | TGGACAGCGT | GGAATTACTT | CTTATGGAGG | AA | | 3522 |

( 2 ) INFORMATION FOR SEQ ID NO:29:

( i ) SEQUENCE CHARACTERISTICS:
        ( A ) LENGTH: 1174 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:29:

```
Met Glu Asn Asn Ile Gln Asn Gln Cys Val Pro Tyr Asn Cys Leu Asn
  1               5                  10                  15

Asn Pro Glu Val Glu Ile Leu Asn Glu Glu Arg Ser Thr Gly Arg Leu
                 20                  25                  30

Pro Leu Asp Ile Ser Leu Ser Leu Thr Arg Phe Leu Leu Ser Glu Phe
             35                  40                  45

Val Pro Gly Val Gly Val Ala Phe Gly Leu Phe Asp Leu Ile Trp Gly
         50                  55                  60

Phe Ile Thr Pro Ser Asp Trp Ser Leu Phe Leu Leu Gln Ile Glu Gln
 65                  70                  75                  80

Leu Ile Glu Gln Arg Ile Glu Thr Leu Glu Arg Asn Arg Ala Ile Thr
                 85                  90                  95

Thr Leu Arg Gly Leu Ala Asp Ser Tyr Glu Ile Tyr Ile Glu Ala Leu
                100                 105                 110

Arg Glu Trp Glu Ala Asn Pro Asn Asn Ala Gln Leu Arg Glu Asp Val
            115                 120                 125

Arg Ile Arg Phe Ala Asn Thr Asp Asp Ala Leu Ile Thr Ala Ile Asn
        130                 135                 140

Asn Phe Thr Leu Thr Ser Phe Glu Ile Pro Leu Leu Ser Val Tyr Val
145                 150                 155                 160
```

```
Gln  Ala  Ala  Asn  Leu  His  Leu  Ser  Leu  Leu  Arg  Asp  Ala  Val  Ser  Phe
               165                 170                      175

Gly  Gln  Gly  Trp  Gly  Leu  Asp  Ile  Ala  Thr  Val  Asn  Asn  His  Tyr  Asn
               180                 185                      190

Arg  Leu  Ile  Asn  Leu  Ile  His  Arg  Tyr  Thr  Lys  His  Cys  Leu  Asp  Thr
               195                 200                      205

Tyr  Asn  Gln  Gly  Leu  Glu  Asn  Leu  Arg  Gly  Thr  Asn  Thr  Arg  Gln  Trp
          210                      215                 220

Ala  Arg  Phe  Asn  Gln  Phe  Arg  Arg  Asp  Leu  Thr  Leu  Thr  Val  Leu  Asp
225                      230                 235                           240

Ile  Val  Ala  Leu  Phe  Pro  Asn  Tyr  Asp  Val  Arg  Thr  Tyr  Pro  Ile  Gln
               245                 250                      255

Thr  Ser  Ser  Gln  Leu  Thr  Arg  Glu  Ile  Tyr  Thr  Ser  Ser  Val  Ile  Glu
               260                 265                      270

Asp  Ser  Pro  Val  Ser  Ala  Asn  Ile  Pro  Asn  Gly  Phe  Asn  Arg  Ala  Glu
               275                 280                      285

Phe  Gly  Val  Arg  Pro  Pro  His  Leu  Met  Asp  Phe  Met  Asn  Ser  Leu  Phe
     290                      295                 300

Val  Thr  Ala  Glu  Thr  Val  Arg  Ser  Gln  Thr  Val  Trp  Gly  Gly  His  Leu
305                 310                 315                                320

Val  Ser  Ser  Arg  Asn  Thr  Ala  Gly  Asn  Arg  Ile  Asn  Phe  Pro  Ser  Tyr
               325                 330                      335

Gly  Val  Phe  Asn  Pro  Gly  Gly  Ala  Ile  Trp  Ile  Ala  Asp  Glu  Asp  Pro
               340                 345                      350

Arg  Pro  Phe  Tyr  Arg  Thr  Leu  Ser  Asp  Pro  Val  Phe  Val  Arg  Gly  Gly
               355                 360                      365

Phe  Gly  Asn  Pro  His  Tyr  Val  Leu  Gly  Leu  Arg  Gly  Val  Ala  Phe  Gln
     370                      375                 380

Gln  Thr  Gly  Thr  Asn  His  Thr  Arg  Thr  Phe  Arg  Asn  Ser  Gly  Thr  Ile
385                      390                 395                           400

Asp  Ser  Leu  Asp  Glu  Ile  Pro  Pro  Gln  Asp  Asn  Ser  Gly  Ala  Pro  Trp
               405                 410                      415

Asn  Asp  Tyr  Ser  His  Val  Leu  Asn  His  Val  Thr  Phe  Val  Arg  Trp  Pro
               420                 425                      430

Gly  Glu  Ile  Ser  Gly  Ser  Asp  Ser  Trp  Arg  Ala  Pro  Met  Phe  Ser  Trp
          435                      440                 445

Thr  His  Arg  Ser  Ala  Thr  Pro  Thr  Asn  Thr  Ile  Asp  Pro  Glu  Arg  Ile
450                      455                 460

Thr  Gln  Ile  Pro  Leu  Val  Lys  Ala  His  Thr  Leu  Gln  Ser  Gly  Thr  Thr
465                      470                 475                           480

Val  Val  Arg  Gly  Pro  Gly  Phe  Thr  Gly  Gly  Asp  Ile  Leu  Arg  Arg  Thr
               485                 490                      495

Ser  Gly  Gly  Pro  Phe  Ala  Tyr  Thr  Ile  Val  Asn  Ile  Asn  Gly  Gln  Leu
               500                 505                      510

Pro  Gln  Arg  Tyr  Arg  Ala  Arg  Ile  Arg  Tyr  Ala  Ser  Thr  Thr  Asn  Leu
          515                      520                 525

Arg  Ile  Tyr  Val  Thr  Val  Ala  Gly  Glu  Arg  Ile  Phe  Ala  Gly  Gln  Phe
     530                      535                 540

Asn  Lys  Thr  Met  Asp  Thr  Gly  Asp  Pro  Leu  Thr  Phe  Gln  Ser  Phe  Ser
545                 550                      555                           560

Tyr  Ala  Thr  Ile  Asn  Thr  Ala  Phe  Thr  Phe  Pro  Met  Ser  Gln  Ser  Ser
               565                 570                      575

Phe  Thr  Val  Gly  Ala  Asp  Thr  Phe  Ser  Ser  Gly  Asn  Glu  Val  Tyr  Ile
```

-continued

|   |   |   | 580 |   |   |   | 585 |   |   |   | 590 |   |   |
|---|---|---|---|---|---|---|---|---|---|---|---|---|---|

Asp Arg Phe Glu Leu Ile Pro Val Thr Ala Thr Phe Glu Ala Glu Tyr
        595                 600                 605

Asp Leu Glu Arg Ala Gln Lys Ala Val Asn Ala Leu Phe Thr Ser Ile
610                 615                 620

Asn Gln Ile Gly Ile Lys Thr Asp Val Thr Asp Tyr His Ile Asp Arg
625                 630                 635                 640

Val Ser Asn Leu Val Thr Tyr Leu Ser Asp Glu Phe Cys Leu Asp Glu
                645                 650                 655

Lys Arg Glu Leu Ser Glu Lys Val Lys His Ala Lys Arg Leu Ser Asp
                660                 665                 670

Glu Arg Asn Leu Leu Gln Asp Ser Asn Phe Lys Asp Ile Asn Arg Gln
        675                 680                 685

Pro Glu Arg Gly Trp Gly Gly Ser Thr Gly Ile Thr Ile Gln Gly Gly
690                 695                 700

Asp Asp Val Phe Lys Glu Asn Tyr Val Thr Leu Ser Gly Thr Phe Asp
705                 710                 715                 720

Glu Cys Tyr Pro Thr Tyr Leu Tyr Gln Lys Ile Asp Glu Ser Lys Leu
                725                 730                 735

Lys Ala Phe Thr Arg Tyr Gln Leu Arg Gly Tyr Ile Glu Asp Ser Gln
                740                 745                 750

Asp Leu Glu Ile Tyr Leu Ile Arg Tyr Asn Ala Lys His Glu Thr Val
                755                 760                 765

Asn Val Pro Gly Thr Gly Ser Leu Trp Pro Leu Ser Ala Gln Ser Pro
770                 775                 780

Ile Gly Lys Cys Gly Glu Pro Asn Arg Cys Ala Pro His Leu Glu Trp
785                 790                 795                 800

Asn Pro Asp Leu Asp Cys Ser Cys Arg Asp Gly Glu Lys Cys Ala His
                805                 810                 815

His Ser His His Phe Ser Leu Asp Ile Asp Val Gly Cys Thr Asp Leu
                820                 825                 830

Asn Glu Asp Leu Gly Val Trp Val Ile Phe Lys Ile Lys Thr Gln Asp
                835                 840                 845

Gly His Ala Arg Leu Gly Asn Leu Glu Phe Leu Glu Glu Lys Pro Leu
        850                 855                 860

Val Gly Glu Ala Leu Ala Arg Val Lys Arg Ala Glu Lys Lys Trp Arg
865                 870                 875                 880

Asp Lys Arg Glu Lys Leu Glu Trp Glu Thr Asn Ile Val Tyr Lys Glu
                885                 890                 895

Ala Lys Glu Ser Val Asp Ala Leu Phe Val Asn Ser Gln Tyr Asp Gln
                900                 905                 910

Leu Gln Ala Asp Thr Asn Ile Ala Met Ile His Ala Ala Asp Lys Arg
        915                 920                 925

Val His Ser Ile Arg Glu Ala Tyr Leu Pro Glu Leu Ser Val Ile Pro
        930                 935                 940

Gly Val Asn Ala Ala Ile Phe Glu Glu Leu Glu Gly Arg Ile Phe Thr
945                 950                 955                 960

Ala Phe Ser Leu Tyr Asp Ala Arg Asn Val Ile Lys Asn Gly Asp Phe
                965                 970                 975

Asn Asn Gly Leu Ser Cys Trp Asn Val Lys Gly His Val Asp Val Glu
                980                 985                 990

Glu Gln Asn Asn His Arg Ser Val Leu Val Val Pro Glu Trp Glu Ala
        995                 1000                1005

```
Glu  Val  Ser  Gln  Glu  Val  Arg  Val  Cys  Pro  Gly  Arg  Gly  Tyr  Ile  Leu
          1010                1015                1020

Arg  Val  Thr  Ala  Tyr  Lys  Glu  Gly  Tyr  Gly  Glu  Gly  Cys  Val  Thr  Ile
1025                1030                1035                               1040

His  Glu  Ile  Glu  Asn  Thr  Asp  Glu  Leu  Lys  Phe  Ser  Asn  Cys  Val
               1045                     1050                     1055

Glu  Glu  Glu  Val  Tyr  Pro  Asn  Asn  Thr  Val  Thr  Cys  Asn  Asp  Tyr  Thr
               1060                     1065                     1070

Ala  Thr  Gln  Glu  Glu  Tyr  Glu  Gly  Thr  Tyr  Thr  Ser  Arg  Asn  Arg  Gly
          1075                     1080                     1085

Tyr  Asp  Gly  Ala  Tyr  Glu  Ser  Asn  Ser  Ser  Val  Pro  Ala  Asp  Tyr  Ala
          1090                     1095                     1100

Ser  Ala  Tyr  Glu  Glu  Lys  Ala  Tyr  Thr  Asp  Gly  Arg  Arg  Asp  Asn  Pro
1105                     1110                     1115                     1120

Cys  Glu  Ser  Asn  Arg  Gly  Tyr  Gly  Asp  Tyr  Thr  Pro  Leu  Pro  Ala  Gly
                    1125                     1130                     1135

Tyr  Val  Thr  Lys  Glu  Leu  Glu  Tyr  Phe  Pro  Glu  Thr  Asp  Lys  Val  Trp
                    1140                     1145                     1150

Ile  Glu  Ile  Gly  Glu  Thr  Glu  Gly  Thr  Phe  Ile  Val  Asp  Ser  Val  Glu
                    1155                     1160                     1165

Leu  Leu  Leu  Met  Glu  Glu
                    1170
```

( 2 ) INFORMATION FOR SEQ ID NO:30:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:30:

```
Xaa  Xaa  Ile  Asp  Xaa  Xaa  Glu  Xaa  Xaa  Xaa  Xaa  Xaa
                    5                             10
```

( 2 ) INFORMATION FOR SEQ ID NO:31:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:31:

```
Tyr  Pro  Asn  Asn  Thr  Val  Thr  Cys
                    5
```

( 2 ) INFORMATION FOR SEQ ID NO:32:

( i ) SEQUENCE CHARACTERISTICS:
        ( A ) LENGTH: 1174 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:32:

```
Met  Glu  Asn  Asn  Ile  Gln  Asn  Gln  Cys  Val  Pro  Tyr  Asn  Cys  Leu  Asn
1                   5                   10                      15
```

```
Asn Pro Glu Val Glu Ile Leu Asn Glu Glu Arg Ser Thr Gly Arg Leu
            20                  25                      30

Pro Leu Asp Ile Ser Leu Ser Leu Thr Arg Phe Leu Leu Ser Glu Phe
            35                  40                      45

Val Pro Gly Val Gly Val Ala Phe Gly Leu Phe Asp Leu Ile Trp Gly
     50                  55                      60

Phe Ile Thr Pro Ser Asp Trp Ser Leu Phe Leu Gln Ile Glu Gln
 65                  70                      75                  80

Leu Ile Glu Gln Arg Ile Glu Thr Leu Glu Arg Asn Arg Ala Ile Thr
                 85                  90                      95

Thr Leu Arg Gly Leu Ala Asp Ser Tyr Glu Ile Tyr Ile Glu Ala Leu
             100                 105                     110

Arg Glu Trp Glu Ala Asn Pro Asn Ala Gln Leu Arg Glu Asp Val
             115                 120                     125

Arg Ile Arg Phe Ala Asn Thr Asp Ala Leu Ile Thr Ala Ile Asn
     130                 135                     140

Asn Phe Thr Leu Thr Ser Phe Glu Ile Pro Leu Leu Ser Val Tyr Val
145                 150                     155                 160

Gln Ala Ala Asn Leu His Leu Ser Leu Leu Arg Asp Ala Val Ser Phe
                165                 170                     175

Gly Gln Gly Trp Gly Leu Asp Ile Ala Thr Val Asn Asn His Tyr Asn
             180                 185                     190

Arg Leu Ile Asn Leu Ile His Arg Tyr Thr Lys His Cys Leu Asp Thr
         195                 200                     205

Tyr Asn Gln Gly Leu Glu Asn Leu Arg Gly Thr Asn Thr Arg Gln Trp
     210                 215                     220

Ala Arg Phe Asn Gln Phe Arg Arg Asp Leu Thr Leu Thr Val Leu Asp
225                 230                     235                 240

Ile Val Ala Leu Phe Pro Asn Tyr Asp Val Arg Thr Tyr Pro Ile Gln
             245                 250                     255

Thr Ser Ser Gln Leu Thr Arg Glu Ile Tyr Thr Ser Ser Val Ile Glu
             260                 265                     270

Asp Ser Pro Val Ser Ala Asn Ile Pro Asn Gly Phe Asn Arg Ala Glu
         275                 280                     285

Phe Gly Val Arg Pro Pro His Leu Met Asp Phe Met Asn Ser Leu Phe
    290                 295                     300

Val Thr Ala Glu Thr Val Arg Ser Gln Thr Val Trp Gly Gly His Leu
305                 310                     315                 320

Val Ser Ser Arg Asn Thr Ala Gly Asn Arg Ile Asn Phe Pro Ser Tyr
             325                 330                     335

Gly Val Phe Asn Pro Gly Gly Ala Ile Trp Ile Ala Asp Glu Asp Pro
             340                 345                     350

Arg Pro Phe Tyr Arg Thr Leu Ser Asp Pro Val Phe Val Arg Gly Gly
         355                 360                     365

Phe Gly Asn Pro His Tyr Val Leu Gly Leu Arg Gly Val Ala Phe Gln
    370                 375                     380

Gln Thr Gly Thr Asn His Thr Arg Thr Phe Arg Asn Ser Gly Thr Ile
385                 390                     395                 400

Asp Ser Leu Asp Glu Ile Pro Pro Gln Asp Asn Ser Gly Ala Pro Trp
             405                 410                     415

Asn Asp Tyr Ser His Val Leu Asn His Val Thr Phe Val Arg Trp Pro
         420                 425                     430

Gly Glu Ile Ser Gly Ser Asp Ser Trp Arg Ala Pro Met Phe Ser Trp
```

-continued

```
                435                          440                          445
Thr His Arg Ser Ala Thr Pro Thr Asn Thr Ile Asp Pro Glu Arg Ile
    450                     455                 460
Thr Gln Ile Pro Leu Val Lys Ala His Thr Leu Gln Ser Gly Thr Thr
465                     470                 475                     480
Val Val Arg Gly Pro Gly Phe Thr Gly Gly Asp Ile Leu Arg Arg Thr
                    485                 490                     495
Ser Gly Gly Pro Phe Ala Tyr Thr Ile Val Asn Ile Asn Gly Gln Leu
                500                 505                     510
Pro Gln Arg Tyr Arg Ala Arg Ile Arg Tyr Ala Ser Thr Thr Asn Leu
            515                 520                 525
Arg Ile Tyr Val Thr Val Ala Gly Glu Arg Ile Phe Ala Gly Gln Phe
        530                 535                 540
Asn Lys Thr Met Asp Thr Gly Asp Pro Leu Thr Phe Gln Ser Phe Ser
545                 550                 555                     560
Tyr Ala Thr Ile Asn Thr Ala Phe Thr Phe Pro Met Ser Gln Ser Ser
                    565                 570                     575
Phe Thr Val Gly Ala Asp Thr Phe Ser Ser Gly Asn Glu Val Tyr Ile
                580                 585                     590
Asp Arg Phe Glu Leu Ile Pro Val Thr Ala Thr Phe Glu Ala Glu Tyr
        595                 600                 605
Asp Leu Glu Arg Ala Gln Lys Ala Val Asn Ala Leu Phe Thr Ser Ile
    610                 615                     620
Asn Gln Ile Gly Ile Lys Thr Asp Val Thr Asp Tyr His Ile Asp Gln
625                     630                 635                     640
Val Ser Asn Leu Val Asp Cys Leu Ser Asp Glu Phe Cys Leu Asp Glu
                    645                 650                     655
Lys Arg Glu Leu Ser Glu Lys Val Lys His Ala Lys Arg Leu Ser Asp
                660                 665                 670
Glu Arg Asn Leu Leu Gln Asp Pro Asn Phe Lys Gly Ile Asn Arg Gln
            675                 680                 685
Leu Asp Arg Gly Trp Arg Gly Ser Thr Asp Ile Thr Ile Gln Arg Gly
690                     695                 700
Asp Asp Val Phe Lys Glu Asn Tyr Val Thr Leu Pro Gly Thr Phe Asp
705                 710                 715                     720
Glu Cys Tyr Pro Thr Tyr Leu Tyr Gln Lys Ile Asp Glu Ser Lys Leu
                725                 730                     735
Lys Pro Tyr Thr Arg Tyr Gln Leu Arg Gly Tyr Ile Glu Asp Ser Gln
            740                 745                     750
Asp Leu Glu Ile Tyr Leu Ile Arg Tyr Asn Ala Lys His Glu Thr Val
    755                 760                 765
Asn Val Leu Gly Thr Gly Ser Leu Trp Pro Leu Ser Val Gln Ser Pro
770                 775                     780
Ile Arg Lys Cys Gly Glu Pro Asn Arg Cys Ala Pro His Leu Glu Trp
785                 790                 795                     800
Asn Pro Asp Leu Asp Cys Ser Cys Arg Asp Gly Glu Lys Cys Ala His
                805                 810                     815
His Ser His His Phe Ser Leu Asp Ile Asp Val Gly Cys Thr Asp Leu
                820                 825                     830
Asn Glu Asp Leu Asp Val Trp Val Ile Phe Lys Ile Lys Thr Gln Asp
            835                 840                     845
Gly His Ala Arg Leu Gly Asn Leu Glu Phe Leu Glu Glu Lys Pro Leu
850                     855                 860
```

|     |     |     |     |     |     |     |     |     |     |     |     |     |     |     |     |
| --- | --- | --- | --- | --- | --- | --- | --- | --- | --- | --- | --- | --- | --- | --- | --- |
| Val | Gly | Glu | Ala | Leu | Ala | Arg | Val | Lys | Arg | Ala | Glu | Lys | Lys | Trp | Arg |
| 865 |     |     |     | 870 |     |     |     | 875 |     |     |     |     |     |     | 880 |
| Asp | Lys | Arg | Glu | Lys | Leu | Glu | Leu | Glu | Thr | Asn | Ile | Val | Tyr | Lys | Glu |
|     |     |     |     | 885 |     |     |     |     | 890 |     |     |     |     | 895 |     |
| Ala | Lys | Glu | Ser | Val | Asp | Ala | Leu | Phe | Val | Asn | Ser | Gln | Tyr | Asp | Gln |
|     |     |     | 900 |     |     |     |     | 905 |     |     |     |     | 910 |     |     |
| Leu | Gln | Ala | Asp | Thr | Asn | Ile | Ala | Met | Ile | His | Ala | Ala | Asp | Lys | Arg |
|     |     | 915 |     |     |     |     |     | 920 |     |     |     |     | 925 |     |     |
| Val | His | Arg | Ile | Arg | Glu | Ala | Tyr | Leu | Pro | Glu | Leu | Ser | Val | Ile | Pro |
|     |     | 930 |     |     |     |     | 935 |     |     |     |     | 940 |     |     |     |
| Gly | Val | Asn | Val | Asp | Ile | Phe | Glu | Glu | Leu | Lys | Gly | Arg | Ile | Phe | Thr |
| 945 |     |     |     |     | 950 |     |     |     |     | 955 |     |     |     |     | 960 |
| Ala | Phe | Phe | Leu | Tyr | Asp | Ala | Arg | Asn | Val | Ile | Lys | Asn | Gly | Asp | Phe |
|     |     |     |     | 965 |     |     |     |     | 970 |     |     |     |     | 975 |     |
| Asn | Asn | Gly | Leu | Ser | Cys | Trp | Asn | Val | Lys | Gly | His | Val | Asp | Val | Glu |
|     |     |     | 980 |     |     |     |     | 985 |     |     |     |     | 990 |     |     |
| Glu | Gln | Asn | Asn | His | Arg | Ser | Val | Leu | Val | Val | Pro | Glu | Trp | Glu | Ala |
|     |     |     | 995 |     |     |     | 1000|     |     |     |     | 1005|     |     |     |
| Glu | Val | Ser | Gln | Glu | Val | Arg | Val | Cys | Pro | Gly | Arg | Gly | Tyr | Ile | Leu |
|     |     | 1010|     |     |     |     | 1015|     |     |     |     | 1020|     |     |     |
| Arg | Val | Thr | Ala | Tyr | Lys | Glu | Gly | Tyr | Gly | Glu | Gly | Cys | Val | Thr | Ile |
| 1025|     |     |     |     | 1030|     |     |     |     | 1035|     |     |     |     | 1040|
| His | Glu | Ile | Glu | Asn | Asn | Thr | Asp | Glu | Leu | Lys | Phe | Ser | Asn | Cys | Val |
|     |     |     |     | 1045|     |     |     |     | 1050|     |     |     |     | 1055|     |
| Glu | Glu | Glu | Val | Tyr | Pro | Asn | Asn | Thr | Val | Thr | Cys | Asn | Asp | Tyr | Thr |
|     |     |     | 1060|     |     |     |     | 1065|     |     |     |     | 1070|     |     |
| Ala | Asn | Gln | Glu | Glu | Tyr | Gly | Gly | Ala | Tyr | Thr | Ser | Arg | Asn | Arg | Gly |
|     |     |     | 1075|     |     |     |     | 1080|     |     |     |     | 1085|     |     |
| Tyr | Asp | Glu | Thr | Tyr | Gly | Ser | Asn | Ser | Ser | Val | Pro | Ala | Asp | Tyr | Ala |
|     |     |     | 1090|     |     |     |     | 1095|     |     |     |     | 1100|     |     |
| Ser | Val | Tyr | Glu | Glu | Lys | Ser | Tyr | Thr | Asp | Gly | Arg | Arg | Asp | Asn | Pro |
| 1105|     |     |     |     | 1110|     |     |     |     | 1115|     |     |     |     | 1120|
| Cys | Glu | Ser | Asn | Arg | Gly | Tyr | Gly | Asp | Tyr | Thr | Pro | Leu | Pro | Ala | Gly |
|     |     |     |     | 1125|     |     |     |     | 1130|     |     |     |     | 1135|     |
| Tyr | Val | Thr | Lys | Glu | Leu | Glu | Tyr | Phe | Pro | Glu | Thr | Asp | Lys | Val | Trp |
|     |     |     |     | 1140|     |     |     |     | 1145|     |     |     |     | 1150|     |
| Ile | Glu | Ile | Gly | Glu | Thr | Glu | Gly | Thr | Phe | Ile | Val | Asp | Ser | Val | Glu |
|     |     |     |     | 1155|     |     |     |     | 1160|     |     |     |     | 1165|     |
| Leu | Leu | Leu | Met | Glu | Glu |     |     |     |     |     |     |     |     |     |     |
|     |     |     | 1170|     |     |     |     |     |     |     |     |     |     |     |     |

( 2 ) INFORMATION FOR SEQ ID NO:33:

( i ) SEQUENCE CHARACTERISTICS:
        ( A ) LENGTH: 1155 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:33:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Asp | Asn | Asn | Pro | Asn | Ile | Asn | Glu | Cys | Ile | Pro | Tyr | Asn | Cys | Leu |
| 1   |     |     |     | 5   |     |     |     |     | 10  |     |     |     |     | 15  |     |
| Ser | Asn | Pro | Glu | Val | Glu | Val | Leu | Gly | Gly | Glu | Arg | Ile | Glu | Thr | Gly |
|     |     |     |     | 20  |     |     |     |     | 25  |     |     |     |     | 30  |     |
| Tyr | Thr | Pro | Ile | Asp | Ile | Ser | Leu | Ser | Leu | Thr | Gln | Phe | Leu | Leu | Ser |

-continued

|     | 35  |     |     |     |     | 40  |     |     |     |     | 45  |     |     |     |
|-----|-----|-----|-----|-----|-----|-----|-----|-----|-----|-----|-----|-----|-----|-----|
| Glu | Phe 50 | Val | Pro | Gly | Ala | Gly 55 | Phe | Val | Leu | Gly | Leu 60 | Val | Asp | Ile | Ile |
| Trp 65 | Gly | Ile | Phe | Gly | Pro 70 | Ser | Gln | Trp | Asp | Ala 75 | Phe | Leu | Val | Gln | Ile 80 |
| Glu | Gln | Leu | Ile | Asn 85 | Gln | Arg | Ile | Glu | Glu 90 | Phe | Ala | Arg | Asn | Gln 95 | Ala |
| Ile | Ser | Arg | Leu 100 | Glu | Gly | Leu | Ser | Asn 105 | Leu | Tyr | Gln | Ile | Tyr 110 | Ala | Glu |
| Ser | Phe | Arg 115 | Glu | Trp | Glu | Ala | Asp 120 | Pro | Thr | Asn | Pro | Ala 125 | Leu | Arg | Glu |
| Glu | Met 130 | Arg | Ile | Gln | Phe | Asn 135 | Asp | Met | Asn | Ser | Ala 140 | Leu | Thr | Thr | Ala |
| Ile 145 | Pro | Leu | Phe | Ala | Val 150 | Gln | Asn | Tyr | Gln | Val 155 | Pro | Leu | Leu | Ser | Val 160 |
| Tyr | Val | Gln | Ala | Ala 165 | Asn | Leu | His | Leu | Ser 170 | Val | Leu | Arg | Asp | Val 175 | Ser |
| Val | Phe | Gly | Gln 180 | Arg | Trp | Gly | Phe | Asp 185 | Ala | Ala | Thr | Ile | Asn 190 | Ser | Arg |
| Tyr | Asn | Asp 195 | Leu | Thr | Arg | Leu | Ile 200 | Gly | Asn | Tyr | Thr | Asp 205 | His | Ala | Val |
| Arg | Trp 210 | Tyr | Asn | Thr | Gly | Leu 215 | Glu | Arg | Val | Trp | Gly 220 | Pro | Asp | Ser | Arg |
| Asp 225 | Trp | Ile | Arg | Tyr | Asn 230 | Gln | Phe | Arg | Arg | Glu 235 | Leu | Thr | Leu | Thr | Val 240 |
| Leu | Asp | Ile | Val | Ser 245 | Leu | Phe | Pro | Asn | Tyr 250 | Asp | Ser | Arg | Thr | Tyr 255 | Pro |
| Ile | Arg | Thr | Val 260 | Ser | Gln | Leu | Thr | Arg 265 | Glu | Ile | Tyr | Thr | Asn 270 | Pro | Val |
| Leu | Glu | Asn 275 | Phe | Asp | Gly | Ser | Phe 280 | Arg | Gly | Ser | Ala | Gln 285 | Gly | Ile | Glu |
| Gly | Ser | Ile 290 | Arg | Ser | Pro | His 295 | Leu | Met | Asp | Ile | Leu 300 | Asn | Ser | Ile | Thr |
| Ile 305 | Tyr | Thr | Asp | Ala | His 310 | Arg | Gly | Glu | Tyr | Tyr 315 | Trp | Ser | Gly | His | Gln 320 |
| Ile | Met | Ala | Ser | Pro 325 | Val | Gly | Phe | Ser | Gly 330 | Pro | Glu | Phe | Thr | Phe 335 | Pro |
| Leu | Tyr | Gly | Thr 340 | Met | Gly | Asn | Ala | Ala 345 | Pro | Gln | Gln | Arg | Ile 350 | Val | Ala |
| Gln | Leu | Gly 355 | Gln | Gly | Val | Tyr | Arg 360 | Thr | Leu | Ser | Ser | Thr 365 | Leu | Tyr | Arg |
| Arg | Pro 370 | Phe | Asn | Ile | Gly | Ile 375 | Asn | Asn | Gln | Gln | Leu 380 | Ser | Val | Leu | Asp |
| Gly 385 | Thr | Glu | Phe | Ala | Tyr 390 | Gly | Thr | Ser | Ser | Asn 395 | Leu | Pro | Ser | Ala | Val 400 |
| Tyr | Arg | Lys | Ser | Gly 405 | Thr | Val | Asp | Ser | Leu 410 | Asp | Glu | Ile | Pro | Pro 415 | Gln |
| Asn | Asn | Asn | Val 420 | Pro | Pro | Arg | Gln | Gly 425 | Phe | Ser | His | Arg | Leu 430 | Ser | His |
| Val | Ser | Met 435 | Phe | Arg | Ser | Gly | Phe 440 | Ser | Asn | Ser | Ser | Val 445 | Ser | Ile | Ile |
| Arg | Ala 450 | Pro | Met | Phe | Ser | Trp 455 | Ile | His | Arg | Ser | Ala 460 | Glu | Phe | Asn | Asn |

```
Ile  Ile  Pro  Ser  Ser  Gln  Ile  Thr  Gln  Ile  Pro  Leu  Thr  Lys  Ser  Thr
465                 470                 475                 480

Asn  Leu  Gly  Ser  Gly  Thr  Ser  Val  Val  Lys  Gly  Pro  Gly  Phe  Thr  Gly
                    485                 490                 495

Gly  Asp  Ile  Leu  Arg  Arg  Thr  Ser  Pro  Gly  Gln  Ile  Ser  Thr  Leu  Arg
               500                 505                 510

Val  Asn  Ile  Thr  Ala  Pro  Leu  Ser  Gln  Arg  Tyr  Arg  Val  Arg  Ile  Arg
          515                 520                      525

Tyr  Ala  Ser  Thr  Thr  Asn  Leu  Gln  Phe  His  Thr  Ser  Ile  Asp  Gly  Arg
530                      535                 540

Pro  Ile  Asn  Gln  Gly  Asn  Phe  Ser  Ala  Thr  Met  Ser  Ser  Gly  Ser  Asn
545                 550                 555                           560

Leu  Gln  Ser  Gly  Ser  Phe  Arg  Thr  Val  Gly  Phe  Thr  Thr  Pro  Phe  Asn
               565                 570                      575

Phe  Ser  Asn  Gly  Ser  Ser  Val  Phe  Thr  Leu  Ser  Ala  His  Val  Phe  Asn
               580                 585                 590

Ser  Gly  Asn  Glu  Val  Tyr  Ile  Asp  Arg  Ile  Glu  Phe  Val  Pro  Ala  Glu
               595                 600                 605

Val  Thr  Phe  Glu  Ala  Glu  Tyr  Asp  Leu  Glu  Arg  Ala  Gln  Lys  Ala  Val
     610                 615                      620

Asn  Glu  Leu  Phe  Thr  Ser  Ser  Asn  Gln  Ile  Gly  Leu  Lys  Thr  Asp  Val
625                      630                 635                      640

Thr  Asp  Tyr  His  Ile  Asp  Gln  Val  Ser  Asn  Leu  Val  Glu  Cys  Leu  Ser
               645                 650                 655

Asp  Glu  Phe  Cys  Leu  Asp  Glu  Lys  Lys  Glu  Leu  Ser  Glu  Lys  Val  Lys
               660                 665                 670

His  Ala  Lys  Arg  Leu  Ser  Asp  Glu  Arg  Asn  Leu  Leu  Gln  Asp  Pro  Asn
          675                 680                 685

Phe  Arg  Gly  Ile  Asn  Arg  Gln  Leu  Asp  Arg  Gly  Trp  Arg  Gly  Ser  Thr
     690                 695                 700

Asp  Ile  Thr  Ile  Gln  Gly  Gly  Asp  Asp  Val  Phe  Lys  Glu  Asn  Tyr  Val
705                      710                 715                      720

Thr  Leu  Leu  Gly  Thr  Phe  Asp  Glu  Cys  Tyr  Pro  Thr  Tyr  Leu  Tyr  Gln
               725                 730                 735

Lys  Ile  Asp  Glu  Ser  Lys  Leu  Lys  Ala  Tyr  Thr  Arg  Tyr  Gln  Leu  Arg
               740                 745                 750

Gly  Tyr  Ile  Glu  Asp  Ser  Gln  Asp  Leu  Glu  Ile  Tyr  Leu  Ile  Arg  Tyr
          755                 760                 765

Asn  Ala  Lys  His  Glu  Thr  Val  Asn  Val  Pro  Gly  Thr  Gly  Ser  Leu  Trp
770                      775                 780

Pro  Leu  Ser  Ala  Pro  Ser  Pro  Ile  Gly  Lys  Cys  Ala  His  His  Ser  His
785                 790                 795                      800

His  Phe  Ser  Leu  Asp  Ile  Asp  Val  Gly  Cys  Thr  Asp  Leu  Asn  Glu  Asp
               805                 810                 815

Leu  Gly  Val  Trp  Val  Ile  Phe  Lys  Ile  Lys  Thr  Gln  Asp  Gly  His  Ala
               820                 825                 830

Arg  Leu  Gly  Asn  Leu  Glu  Phe  Leu  Glu  Glu  Lys  Pro  Leu  Val  Gly  Glu
               835                 840                 845

Ala  Leu  Ala  Arg  Val  Lys  Arg  Ala  Glu  Lys  Lys  Trp  Arg  Asp  Lys  Arg
     850                 855                 860

Glu  Lys  Leu  Glu  Trp  Glu  Thr  Asn  Ile  Val  Tyr  Lys  Glu  Ala  Lys  Glu
865                 870                 875                           880

Ser  Val  Asp  Ala  Leu  Phe  Val  Asn  Ser  Gln  Tyr  Asp  Arg  Leu  Gln  Ala
               885                 890                 895
```

Asp Thr Asn Ile Ala Met Ile His Ala Ala Asp Lys Arg Val His Ser
            900                 905                 910

Ile Arg Glu Ala Tyr Leu Pro Glu Leu Ser Val Ile Pro Gly Val Asn
        915                 920                 925

Ala Ala Ile Phe Glu Glu Leu Glu Gly Arg Ile Phe Thr Ala Phe Ser
    930                 935                 940

Leu Tyr Asp Ala Arg Asn Val Ile Lys Asn Gly Asp Phe Asn Asn Gly
945                 950                 955                 960

Leu Ser Cys Trp Asn Val Lys Gly His Val Asp Val Glu Glu Gln Asn
            965                 970                 975

Asn His Arg Ser Val Leu Val Val Pro Glu Trp Glu Ala Glu Val Ser
            980                 985                 990

Gln Glu Val Arg Val Cys Pro Gly Arg Gly Tyr Ile Leu Arg Val Thr
        995                 1000                1005

Ala Tyr Lys Glu Gly Tyr Gly Glu Gly Cys Val Thr Ile His Glu Ile
    1010                1015                1020

Glu Asn Asn Thr Asp Glu Leu Lys Phe Ser Asn Cys Val Glu Glu Glu
1025                1030                1035                1040

Val Tyr Pro Asn Asn Thr Val Thr Cys Asn Asp Tyr Thr Ala Thr Gln
            1045                1050                1055

Glu Glu Tyr Glu Gly Thr Tyr Thr Ser Arg Asn Arg Gly Tyr Asp Gly
        1060                1065                1070

Ala Tyr Glu Ser Asn Ser Ser Val Pro Ala Asp Tyr Ala Ser Ala Tyr
    1075                1080                1085

Glu Glu Lys Ala Tyr Thr Asp Gly Arg Arg Asp Asn Pro Cys Glu Ser
    1090                1095                1100

Asn Arg Gly Tyr Gly Asp Tyr Thr Pro Leu Pro Ala Gly Tyr Val Thr
1105                1110                1115                1120

Lys Glu Leu Glu Tyr Phe Pro Glu Thr Asp Lys Val Trp Ile Glu Ile
            1125                1130                1135

Gly Glu Thr Glu Gly Thr Phe Ile Val Asp Ser Val Glu Leu Leu Leu
            1140                1145                1150

Met Glu Glu
    1155

( 2 ) INFORMATION FOR SEQ ID NO:34:

( i ) SEQUENCE CHARACTERISTICS:
        ( A ) LENGTH: 1182 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:34:

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

```
Glu Gln Leu Ile Asn Gln Arg Ile Glu Glu Phe Ala Arg Asn Gln Ala
             85                  90                  95
Ile Ser Arg Leu Glu Gly Leu Ser Asn Leu Tyr Gln Ile Tyr Ala Glu
            100             105             110
Ser Phe Arg Glu Trp Glu Ala Asp Pro Thr Asn Pro Ala Leu Arg Glu
        115                 120                 125
Glu Met Arg Ile Gln Phe Asn Asp Met Asn Ser Ala Leu Thr Thr Ala
    130                 135                 140
Ile Pro Leu Phe Ala Val Gln Asn Tyr Gln Val Pro Leu Leu Ser Val
145                 150                 155                 160
Tyr Val Gln Ala Ala Asn Leu His Leu Ser Val Leu Arg Asp Val Ser
                165                 170                 175
Val Phe Gly Gln Arg Trp Gly Phe Asp Ala Ala Thr Ile Asn Ser Arg
            180                 185                 190
Tyr Asn Asp Leu Thr Arg Leu Ile Gly Asn Tyr Thr Asp Tyr Ala Val
        195                 200                 205
Arg Trp Tyr Asn Thr Gly Leu Glu Arg Val Trp Gly Pro Asp Ser Arg
    210                 215                 220
Asp Trp Val Arg Tyr Asn Gln Phe Arg Arg Glu Leu Thr Leu Thr Val
225                 230                 235                 240
Leu Asp Ile Val Ala Leu Phe Pro Asn Tyr Asp Ser Arg Arg Tyr Pro
                245                 250                 255
Ile Arg Thr Val Ser Gln Leu Thr Arg Glu Ile Tyr Thr Asn Pro Val
            260                 265                 270
Leu Glu Asn Phe Asp Gly Ser Phe Arg Gly Ser Ala Gln Gly Ile Glu
        275                 280                 285
Arg Ser Ile Arg Ser Pro His Leu Met Asp Ile Leu Asn Ser Ile Thr
    290                 295                 300
Ile Tyr Thr Asp Ala His Arg Gly Tyr Tyr Tyr Trp Ser Gly His Gln
305                 310                 315                 320
Ile Met Ala Ser Pro Val Gly Phe Ser Gly Pro Glu Phe Thr Phe Pro
                325                 330                 335
Leu Tyr Gly Thr Met Gly Asn Ala Ala Pro Gln Gln Arg Ile Val Ala
            340                 345                 350
Gln Leu Gly Gln Gly Val Tyr Arg Thr Leu Ser Ser Thr Leu Tyr Arg
        355                 360                 365
Arg Pro Phe Asn Ile Gly Ile Asn Asn Gln Gln Leu Ser Val Leu Asp
    370                 375                 380
Gly Thr Glu Phe Ala Tyr Gly Thr Ser Ser Asn Leu Pro Ser Ala Val
385                 390                 395                 400
Tyr Arg Lys Ser Gly Thr Val Asp Ser Leu Asp Glu Ile Pro Pro Gln
                405                 410                 415
Asn Asn Asn Val Pro Pro Arg Gln Gly Phe Ser His Arg Leu Ser His
            420                 425                 430
Val Ser Met Phe Arg Ser Gly Phe Ser Asn Ser Ser Val Ser Ile Ile
        435                 440                 445
Arg Ala Pro Met Phe Ser Trp Ile His Arg Ser Ala Glu Phe Asn Asn
    450                 455                 460
Ile Ile Ala Ser Asp Ser Ile Thr Gln Ile Pro Ala Val Lys Gly Asn
465                 470                 475                 480
Phe Leu Phe Asn Gly Ser Val Ile Ser Gly Pro Gly Phe Thr Gly Gly
                485                 490                 495
Asp Leu Val Arg Leu Asn Ser Ser Gly Asn Asn Ile Gln Asn Arg Gly
            500                 505                 510
```

```
Tyr  Ile  Glu  Val  Pro  Ile  His  Phe  Pro  Ser  Thr  Ser  Thr  Arg  Tyr  Arg
          515                      520                     525

Val  Arg  Val  Arg  Tyr  Ala  Ser  Val  Thr  Pro  Ile  His  Leu  Asn  Val  Asn
     530                     535                     540

Trp  Gly  Asn  Ser  Ser  Ile  Phe  Ser  Asn  Thr  Val  Pro  Ala  Thr  Ala  Thr
545                      550                     555                          560

Ser  Leu  Asp  Asn  Leu  Gln  Ser  Ser  Asp  Phe  Gly  Tyr  Phe  Glu  Ser  Ala
                    565                     570                          575

Asn  Ala  Phe  Thr  Ser  Ser  Leu  Gly  Asn  Ile  Val  Gly  Val  Arg  Asn  Phe
               580                     585                          590

Ser  Gly  Thr  Ala  Gly  Val  Ile  Ile  Asp  Arg  Phe  Glu  Phe  Ile  Pro  Val
          595                      600                     605

Thr  Ala  Thr  Leu  Glu  Ala  Glu  Tyr  Asn  Leu  Glu  Arg  Ala  Gln  Lys  Ala
610                      615                          620

Val  Asn  Ala  Leu  Phe  Thr  Ser  Thr  Asn  Gln  Leu  Gly  Leu  Lys  Thr  Asn
625                           630                     635                          640

Val  Thr  Asp  Tyr  His  Ile  Asp  Gln  Val  Ser  Asn  Leu  Val  Thr  Tyr  Leu
                    645                     650                          655

Ser  Asp  Glu  Phe  Cys  Leu  Asp  Glu  Lys  Arg  Glu  Leu  Ser  Glu  Lys  Val
               660                     665                          670

Lys  His  Ala  Lys  Arg  Leu  Ser  Asp  Glu  Arg  Asn  Leu  Leu  Gln  Asp  Ser
               675                     680                          685

Asn  Phe  Lys  Asp  Ile  Asn  Arg  Gln  Pro  Glu  Arg  Gly  Trp  Gly  Gly  Ser
          690                      695                     700

Thr  Gly  Ile  Thr  Ile  Gln  Gly  Gly  Asp  Asp  Val  Phe  Lys  Glu  Asn  Tyr
705                      710                     715                          720

Val  Thr  Leu  Ser  Gly  Thr  Phe  Asp  Glu  Cys  Tyr  Pro  Thr  Tyr  Leu  Tyr
                    725                     730                          735

Gln  Lys  Ile  Asp  Glu  Ser  Lys  Leu  Lys  Ala  Phe  Thr  Arg  Tyr  Gln  Leu
               740                     745                          750

Arg  Gly  Tyr  Ile  Glu  Asp  Ser  Gln  Asp  Leu  Glu  Ile  Tyr  Leu  Ile  Arg
          755                      760                     765

Tyr  Asn  Ala  Lys  His  Glu  Thr  Val  Asn  Val  Pro  Gly  Thr  Gly  Ser  Leu
770                      775                          780

Trp  Pro  Leu  Ser  Ala  Gln  Ser  Pro  Ile  Gly  Lys  Cys  Gly  Glu  Pro  Asn
785                      790                     795                          800

Arg  Cys  Ala  Pro  His  Leu  Glu  Trp  Asn  Pro  Asp  Leu  Asp  Cys  Ser  Cys
                    805                     810                          815

Arg  Asp  Gly  Glu  Lys  Cys  Ala  His  His  Ser  His  His  Phe  Ser  Leu  Asp
               820                     825                          830

Ile  Asp  Val  Gly  Cys  Thr  Asp  Leu  Asn  Glu  Asp  Leu  Gly  Val  Trp  Val
          835                      840                     845

Ile  Phe  Lys  Ile  Lys  Thr  Gln  Asp  Gly  His  Ala  Arg  Leu  Gly  Asn  Leu
850                      855                          860

Glu  Phe  Leu  Glu  Glu  Lys  Pro  Leu  Val  Gly  Glu  Ala  Leu  Ala  Arg  Val
865                           870                     875                          880

Lys  Arg  Ala  Glu  Lys  Lys  Trp  Arg  Asp  Lys  Arg  Glu  Lys  Leu  Glu  Trp
                         885                     890                          895

Glu  Thr  Asn  Ile  Val  Tyr  Lys  Glu  Ala  Lys  Glu  Ser  Val  Asp  Ala  Leu
               900                     905                          910

Phe  Val  Asn  Ser  Gln  Tyr  Asp  Gln  Leu  Gln  Ala  Asp  Thr  Asn  Ile  Ala
          915                     920                          925

Met  Ile  His  Ala  Ala  Asp  Lys  Arg  Val  His  Ser  Ile  Arg  Glu  Ala  Tyr
```

|     |     |     |     |     | 930 |     |     |     |     | 935 |     |     |     |     | 940 |     |     |
| --- | --- | --- | --- | --- | --- | --- | --- | --- | --- | --- | --- | --- | --- | --- | --- | --- | --- |
| Leu | Pro | Glu | Leu | Ser | Val | Ile | Pro | Gly | Val | Asn | Ala | Ala | Ile | Phe | Glu |
| 945 |     |     |     |     | 950 |     |     |     |     | 955 |     |     |     |     | 960 |
| Glu | Leu | Glu | Gly | Arg | Ile | Phe | Thr | Ala | Phe | Ser | Leu | Tyr | Asp | Ala | Arg |
|     |     |     |     | 965 |     |     |     |     | 970 |     |     |     |     | 975 |     |
| Asn | Val | Ile | Lys | Asn | Gly | Asp | Phe | Asn | Asn | Gly | Leu | Ser | Cys | Trp | Asn |
|     |     |     | 980 |     |     |     |     | 985 |     |     |     |     | 990 |     |     |
| Val | Lys | Gly | His | Val | Asp | Val | Glu | Gln | Asn | Asn | His | Arg | Ser | Val |
|     |     | 995 |     |     |     |     | 1000 |     |     |     |     | 1005 |     |     |
| Leu | Val | Val | Pro | Glu | Trp | Glu | Ala | Glu | Val | Ser | Gln | Glu | Val | Arg | Val |
|     |     | 1010 |     |     |     |     | 1015 |     |     |     |     | 1020 |     |     |     |
| Cys | Pro | Gly | Arg | Gly | Tyr | Ile | Leu | Arg | Val | Thr | Ala | Tyr | Lys | Glu | Gly |
| 1025 |     |     |     |     | 1030 |     |     |     |     | 1035 |     |     |     |     | 1040 |
| Tyr | Gly | Glu | Gly | Cys | Val | Thr | Ile | His | Glu | Ile | Glu | Asn | Asn | Thr | Asp |
|     |     |     |     | 1045 |     |     |     |     | 1050 |     |     |     |     | 1055 |     |
| Glu | Leu | Lys | Phe | Ser | Asn | Cys | Val | Glu | Glu | Val | Tyr | Pro | Asn | Asn |
|     |     |     |     | 1060 |     |     |     |     | 1065 |     |     |     |     | 1070 |     |
| Thr | Val | Thr | Cys | Asn | Asp | Tyr | Thr | Ala | Thr | Gln | Glu | Glu | Tyr | Glu | Gly |
|     |     |     | 1075 |     |     |     |     | 1080 |     |     |     |     | 1085 |     |     |
| Thr | Tyr | Thr | Ser | Arg | Asn | Arg | Gly | Tyr | Asp | Gly | Ala | Tyr | Glu | Ser | Asn |
|     |     | 1090 |     |     |     |     | 1095 |     |     |     |     | 1100 |     |     |     |
| Ser | Ser | Val | Pro | Ala | Asp | Tyr | Ala | Ser | Ala | Tyr | Glu | Glu | Lys | Ala | Tyr |
| 1105 |     |     |     |     | 1110 |     |     |     |     | 1115 |     |     |     |     | 1120 |
| Thr | Asp | Gly | Arg | Arg | Asp | Asn | Pro | Cys | Glu | Ser | Asn | Arg | Gly | Tyr | Gly |
|     |     |     |     | 1125 |     |     |     |     | 1130 |     |     |     |     | 1135 |     |
| Asp | Tyr | Thr | Pro | Leu | Pro | Ala | Gly | Tyr | Val | Thr | Lys | Glu | Leu | Glu | Tyr |
|     |     |     | 1140 |     |     |     |     | 1145 |     |     |     |     | 1150 |     |     |
| Phe | Pro | Glu | Thr | Asp | Lys | Val | Trp | Ile | Glu | Ile | Gly | Glu | Thr | Glu | Gly |
|     |     |     | 1155 |     |     |     |     | 1160 |     |     |     |     | 1165 |     |     |
| Thr | Phe | Ile | Val | Asp | Ser | Val | Glu | Leu | Leu | Leu | Met | Glu | Glu |
|     |     |     | 1170 |     |     |     |     | 1175 |     |     |     | 1180 |     |

( 2 ) INFORMATION FOR SEQ ID NO:35:

( i ) SEQUENCE CHARACTERISTICS:
        ( A ) LENGTH: 1148 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:35:

| Met | Glu | Asn | Asn | Ile | Gln | Asn | Gln | Cys | Val | Pro | Tyr | Asn | Cys | Leu | Asn |
| --- | --- | --- | --- | --- | --- | --- | --- | --- | --- | --- | --- | --- | --- | --- | --- |
| 1 |     |     |     | 5 |     |     |     |     | 10 |     |     |     |     | 15 |     |
| Asn | Pro | Glu | Val | Glu | Ile | Leu | Asn | Glu | Glu | Arg | Ser | Thr | Gly | Arg | Leu |
|     |     |     | 20 |     |     |     |     | 25 |     |     |     |     | 30 |     |     |
| Pro | Leu | Asp | Ile | Ser | Leu | Ser | Leu | Thr | Arg | Phe | Leu | Leu | Ser | Glu | Phe |
|     |     | 35 |     |     |     |     | 40 |     |     |     |     | 45 |     |     |     |
| Val | Pro | Gly | Val | Gly | Val | Ala | Phe | Gly | Leu | Phe | Asp | Leu | Ile | Trp | Gly |
|     | 50 |     |     |     |     | 55 |     |     |     |     | 60 |     |     |     |     |
| Phe | Ile | Thr | Pro | Ser | Asp | Trp | Ser | Leu | Phe | Leu | Leu | Gln | Ile | Glu | Gln |
| 65 |     |     |     |     | 70 |     |     |     |     | 75 |     |     |     |     | 80 |
| Leu | Ile | Glu | Gln | Arg | Ile | Glu | Thr | Leu | Glu | Arg | Asn | Arg | Ala | Ile | Thr |
|     |     |     |     | 85 |     |     |     |     | 90 |     |     |     |     | 95 |     |
| Thr | Leu | Arg | Gly | Leu | Ala | Asp | Ser | Tyr | Glu | Ile | Tyr | Ile | Glu | Ala | Leu |
|     |     |     | 100 |     |     |     |     | 105 |     |     |     |     | 110 |     |     |

Arg Glu Trp Glu Ala Asn Pro Asn Asn Ala Gln Leu Arg Glu Asp Val
         115             120                 125

Arg Ile Arg Phe Ala Asn Thr Asp Asp Ala Leu Ile Thr Ala Ile Asn
         130             135                 140

Asn Phe Thr Leu Thr Ser Phe Glu Ile Pro Leu Leu Ser Val Tyr Val
145              150                 155                     160

Gln Ala Ala Asn Leu His Leu Ser Leu Leu Arg Asp Ala Val Ser Phe
                 165                 170                 175

Gly Gln Gly Trp Gly Leu Asp Ile Ala Thr Val Asn Asn His Tyr Asn
             180             185                 190

Arg Leu Ile Asn Leu Ile His Arg Tyr Thr Lys His Cys Leu Asp Thr
         195             200                 205

Tyr Asn Gln Gly Leu Glu Asn Leu Arg Gly Thr Asn Thr Arg Gln Trp
    210                 215                 220

Ala Arg Phe Asn Gln Phe Arg Arg Asp Leu Thr Leu Thr Val Leu Asp
225                 230                 235                 240

Ile Val Ala Leu Phe Pro Asn Tyr Asp Val Arg Thr Tyr Pro Ile Gln
             245                 250                 255

Thr Ser Ser Gln Leu Thr Arg Glu Ile Tyr Thr Ser Ser Val Ile Glu
             260                 265                 270

Asp Ser Pro Val Ser Ala Asn Ile Pro Asn Gly Phe Asn Arg Ala Glu
         275             280                 285

Phe Gly Val Arg Pro Pro His Leu Met Asp Phe Met Asn Ser Leu Phe
    290                 295                 300

Val Thr Ala Glu Thr Val Arg Ser Gln Thr Val Trp Gly Gly His Leu
305                 310                 315                 320

Val Ser Ser Arg Asn Thr Ala Gly Asn Arg Ile Asn Phe Pro Ser Tyr
             325                 330                 335

Gly Val Phe Asn Pro Gly Gly Ala Ile Trp Ile Ala Asp Glu Asp Pro
             340                 345                 350

Arg Pro Phe Tyr Arg Thr Leu Ser Asp Pro Val Phe Val Arg Gly Gly
             355                 360                 365

Phe Gly Asn Pro His Tyr Val Leu Gly Leu Arg Gly Val Ala Phe Gln
    370                 375                 380

Gln Thr Gly Thr Asn His Thr Arg Thr Phe Arg Asn Ser Gly Thr Ile
385                 390                 395                 400

Asp Ser Leu Asp Glu Ile Pro Pro Gln Asp Asn Ser Gly Ala Pro Trp
             405                 410                 415

Asn Asp Tyr Ser His Val Leu Asn His Val Thr Phe Val Arg Trp Pro
             420                 425                 430

Gly Glu Ile Ser Gly Ser Asp Ser Trp Arg Ala Pro Met Phe Ser Trp
         435             440                 445

Thr His Arg Ser Ala Thr Pro Thr Asn Thr Ile Asp Pro Glu Arg Ile
    450                 455                 460

Thr Gln Ile Pro Leu Val Lys Ala His Thr Leu Gln Ser Gly Thr Thr
465                 470                 475                 480

Val Val Arg Gly Pro Gly Phe Thr Gly Gly Asp Ile Leu Arg Arg Thr
             485                 490                 495

Ser Gly Gly Pro Phe Ala Tyr Thr Ile Val Asn Ile Asn Gly Gln Leu
         500                 505                 510

Pro Gln Arg Tyr Arg Ala Arg Ile Arg Tyr Ala Ser Thr Thr Asn Leu
         515                 520                 525

Arg Ile Tyr Val Thr Val Ala Gly Glu Arg Ile Phe Ala Gly Gln Phe

-continued

|  |  |  | 530 |  |  |  |  |  | 535 |  |  |  |  | 540 |  |
|---|---|---|---|---|---|---|---|---|---|---|---|---|---|---|---|
| Asn 545 | Lys | Thr | Met | Asp 550 | Thr | Gly | Asp | Pro | Leu 555 | Thr | Phe | Gln | Ser | Phe | Ser 560 |
| Tyr | Ala | Thr | Ile | Asn 565 | Thr | Ala | Phe | Thr 570 | Phe | Pro | Met | Ser | Gln | Ser | Ser 575 |
| Phe | Thr | Val | Gly 580 | Ala | Asp | Thr | Phe | Ser 585 | Ser | Gly | Asn | Glu | Val 590 | Tyr | Ile |
| Asp | Arg | Phe 595 | Glu | Leu | Ile | Pro | Val 600 | Thr | Ala | Thr | Phe | Glu 605 | Ala | Glu | Tyr |
| Asp | Leu 610 | Glu | Arg | Ala | Gln | Lys 615 | Ala | Val | Asn | Glu | Leu 620 | Phe | Thr | Ser | Ser |
| Asn 625 | Gln | Ile | Gly | Leu | Lys 630 | Thr | Asp | Val | Thr | Asp 635 | Tyr | His | Ile | Asp | Arg 640 |
| Val | Ser | Asn | Leu | Val 645 | Glu | Cys | Leu | Ser | Asp 650 | Glu | Phe | Cys | Leu | Asp 655 | Glu |
| Lys | Lys | Glu | Leu 660 | Ser | Glu | Lys | Val 665 | Lys | His | Ala | Lys | Arg | Leu 670 | Ser | Asp |
| Glu | Arg | Asn 675 | Leu | Leu | Gln | Asp | Pro 680 | Asn | Phe | Arg | Gly | Ile 685 | Asn | Arg | Gln |
| Leu | Asp 690 | Arg | Gly | Trp | Arg | Gly 695 | Ser | Thr | Asp | Ile | Thr 700 | Ile | Gln | Gly | Gly |
| Asp 705 | Asp | Val | Phe | Lys | Glu 710 | Asn | Tyr | Val | Thr | Leu 715 | Leu | Gly | Thr | Phe | Asp 720 |
| Glu | Cys | Tyr | Pro | Thr 725 | Tyr | Leu | Tyr | Gln | Lys 730 | Ile | Asp | Glu | Ser | Lys 735 | Leu |
| Lys | Ala | Tyr | Thr 740 | Arg | Tyr | Gln | Leu | Arg 745 | Gly | Tyr | Ile | Glu | Asp 750 | Ser | Gln |
| Asp | Leu | Glu 755 | Ile | Tyr | Leu | Ile | Arg 760 | Tyr | Asn | Ala | Lys | His 765 | Glu | Thr | Val |
| Asn | Val 770 | Pro | Gly | Thr | Gly | Ser 775 | Leu | Trp | Pro | Leu | Ser 780 | Ala | Pro | Ser | Pro |
| Ile 785 | Gly | Lys | Cys | Ala | His 790 | His | Ser | His | His | Phe 795 | Ser | Leu | Asp | Ile | Asp 800 |
| Val | Gly | Cys | Thr | Asp 805 | Leu | Asn | Glu | Asp | Leu 810 | Gly | Val | Trp | Val | Ile | Phe 815 |
| Lys | Ile | Lys | Thr 820 | Gln | Asp | Gly | His | Ala 825 | Arg | Leu | Gly | Asn | Leu 830 | Glu | Phe |
| Leu | Glu | Glu 835 | Lys | Pro | Leu | Val | Gly 840 | Glu | Ala | Leu | Ala | Arg 845 | Val | Lys | Arg |
| Ala | Glu 850 | Lys | Lys | Trp | Arg | Asp 855 | Lys | Arg | Glu | Lys | Leu 860 | Glu | Trp | Glu | Thr |
| Asn 865 | Ile | Val | Tyr | Lys | Glu 870 | Ala | Lys | Glu | Ser | Val 875 | Asp | Ala | Leu | Phe | Val 880 |
| Asn | Ser | Gln | Tyr | Asp 885 | Arg | Leu | Gln | Ala | Asp 890 | Thr | Asn | Ile | Ala | Met 895 | Ile |
| His | Ala | Ala | Asp 900 | Lys | Arg | Val | His | Ser 905 | Ile | Arg | Glu | Ala | Tyr 910 | Leu | Pro |
| Glu | Leu | Ser 915 | Val | Ile | Pro | Gly | Val 920 | Asn | Ala | Ala | Ile | Phe 925 | Glu | Glu | Leu |
| Glu | Gly 930 | Arg | Ile | Phe | Thr | Ala 935 | Phe | Ser | Leu | Tyr | Asp 940 | Ala | Arg | Asn | Val |
| Ile 945 | Lys | Asn | Gly | Asp | Phe 950 | Asn | Asn | Gly | Leu | Ser 955 | Cys | Trp | Asn | Val | Lys 960 |

|   |   |   |   |   |   |   |   |   |   |   |   |   |   |   |
|---|---|---|---|---|---|---|---|---|---|---|---|---|---|---|
| Gly | His | Val | Asp | Val | Glu | Glu | Gln | Asn | Asn | His | Arg | Ser | Val | Leu | Val |
|   |   |   |   | 965 |   |   |   |   | 970 |   |   |   |   | 975 |

|   |   |   |   |   |   |   |   |   |   |   |   |   |   |   |   |
|---|---|---|---|---|---|---|---|---|---|---|---|---|---|---|---|
| Val | Pro | Glu | Trp | Glu | Ala | Glu | Val | Ser | Gln | Glu | Val | Arg | Val | Cys | Pro |
|   |   |   | 980 |   |   |   |   | 985 |   |   |   |   | 990 |   |   |

| Gly | Arg | Gly | Tyr | Ile | Leu | Arg | Val | Thr | Ala | Tyr | Lys | Glu | Gly | Tyr | Gly |
|---|---|---|---|---|---|---|---|---|---|---|---|---|---|---|---|
|   |   | 995 |   |   |   |   | 1000 |   |   |   |   | 1005 |   |   |   |

| Glu | Gly | Cys | Val | Thr | Ile | His | Glu | Ile | Glu | Asn | Asn | Thr | Asp | Glu | Leu |
|---|---|---|---|---|---|---|---|---|---|---|---|---|---|---|---|
|   | 1010 |   |   |   |   | 1015 |   |   |   |   | 1020 |   |   |   |   |

| Lys | Phe | Ser | Asn | Cys | Val | Glu | Glu | Val | Tyr | Pro | Asn | Asn | Thr | Val |
|---|---|---|---|---|---|---|---|---|---|---|---|---|---|---|
| 1025 |   |   |   |   | 1030 |   |   |   |   | 1035 |   |   |   | 1040 |

| Thr | Cys | Asn | Asp | Tyr | Thr | Ala | Thr | Gln | Glu | Glu | Tyr | Glu | Gly | Thr | Tyr |
|---|---|---|---|---|---|---|---|---|---|---|---|---|---|---|---|
|   |   |   |   | 1045 |   |   |   |   | 1050 |   |   |   |   | 1055 |   |

| Thr | Ser | Arg | Asn | Arg | Gly | Tyr | Asp | Gly | Ala | Tyr | Glu | Ser | Asn | Ser | Ser |
|---|---|---|---|---|---|---|---|---|---|---|---|---|---|---|---|
|   |   |   | 1060 |   |   |   |   | 1065 |   |   |   |   | 1070 |   |   |

| Val | Pro | Ala | Asp | Tyr | Ala | Ser | Ala | Tyr | Glu | Glu | Lys | Ala | Tyr | Thr | Asp |
|---|---|---|---|---|---|---|---|---|---|---|---|---|---|---|---|
| 1075 |   |   |   |   |   | 1080 |   |   |   |   | 1085 |   |   |   |   |

| Gly | Arg | Arg | Asp | Asn | Pro | Cys | Glu | Ser | Asn | Arg | Gly | Tyr | Gly | Asp | Tyr |
|---|---|---|---|---|---|---|---|---|---|---|---|---|---|---|---|
|   | 1090 |   |   |   |   | 1095 |   |   |   |   | 1100 |   |   |   |   |

| Thr | Pro | Leu | Pro | Ala | Gly | Tyr | Val | Thr | Lys | Glu | Leu | Glu | Tyr | Phe | Pro |
|---|---|---|---|---|---|---|---|---|---|---|---|---|---|---|---|
| 1105 |   |   |   |   | 1110 |   |   |   |   | 1115 |   |   |   |   | 1120 |

| Glu | Thr | Asp | Lys | Val | Trp | Ile | Glu | Ile | Gly | Glu | Thr | Glu | Gly | Thr | Phe |
|---|---|---|---|---|---|---|---|---|---|---|---|---|---|---|---|
|   |   |   |   | 1125 |   |   |   |   | 1130 |   |   |   |   | 1135 |   |

| Ile | Val | Asp | Ser | Val | Glu | Leu | Leu | Leu | Met | Glu | Glu |
|---|---|---|---|---|---|---|---|---|---|---|---|
|   |   |   |   | 1140 |   |   |   | 1145 |   |   |   |

(2) INFORMATION FOR SEQ ID NO:36:

(i) SEQUENCE CHARACTERISTICS:
        (A) LENGTH: 1175 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:36:

| Met | Glu | Asn | Asn | Ile | Gln | Asn | Gln | Cys | Val | Pro | Tyr | Asn | Cys | Leu | Asn |
|---|---|---|---|---|---|---|---|---|---|---|---|---|---|---|---|
| 1 |   |   |   | 5 |   |   |   |   | 10 |   |   |   |   | 15 |   |

| Asn | Pro | Glu | Val | Glu | Ile | Leu | Asn | Glu | Arg | Ser | Thr | Gly | Arg | Leu |
|---|---|---|---|---|---|---|---|---|---|---|---|---|---|---|
|   |   |   | 20 |   |   |   |   | 25 |   |   |   |   | 30 |   |

| Pro | Leu | Asp | Ile | Ser | Leu | Ser | Leu | Thr | Arg | Phe | Leu | Leu | Ser | Glu | Phe |
|---|---|---|---|---|---|---|---|---|---|---|---|---|---|---|---|
|   |   | 35 |   |   |   |   | 40 |   |   |   |   | 45 |   |   |   |

| Val | Pro | Gly | Val | Gly | Val | Ala | Phe | Gly | Leu | Phe | Asp | Leu | Ile | Trp | Gly |
|---|---|---|---|---|---|---|---|---|---|---|---|---|---|---|---|
|   | 50 |   |   |   |   | 55 |   |   |   |   | 60 |   |   |   |   |

| Phe | Ile | Thr | Pro | Ser | Asp | Trp | Ser | Leu | Phe | Leu | Leu | Gln | Ile | Glu | Gln |
|---|---|---|---|---|---|---|---|---|---|---|---|---|---|---|---|
| 65 |   |   |   |   | 70 |   |   |   |   | 75 |   |   |   |   | 80 |

| Leu | Ile | Glu | Gln | Arg | Ile | Glu | Thr | Leu | Glu | Arg | Asn | Arg | Ala | Ile | Thr |
|---|---|---|---|---|---|---|---|---|---|---|---|---|---|---|---|
|   |   |   |   | 85 |   |   |   |   | 90 |   |   |   |   | 95 |   |

| Thr | Leu | Arg | Gly | Leu | Ala | Asp | Ser | Tyr | Glu | Ile | Tyr | Ile | Glu | Ala | Leu |
|---|---|---|---|---|---|---|---|---|---|---|---|---|---|---|---|
|   |   |   | 100 |   |   |   |   | 105 |   |   |   |   | 110 |   |   |

| Arg | Glu | Trp | Glu | Ala | Asn | Pro | Asn | Asn | Ala | Gln | Leu | Arg | Glu | Asp | Val |
|---|---|---|---|---|---|---|---|---|---|---|---|---|---|---|---|
|   |   |   | 115 |   |   |   |   | 120 |   |   |   |   | 125 |   |   |

| Arg | Ile | Arg | Phe | Ala | Asn | Thr | Asp | Asp | Ala | Leu | Ile | Thr | Ala | Ile | Asn |
|---|---|---|---|---|---|---|---|---|---|---|---|---|---|---|---|
|   |   | 130 |   |   |   |   | 135 |   |   |   |   | 140 |   |   |   |

| Asn | Phe | Thr | Leu | Thr | Ser | Phe | Glu | Ile | Pro | Leu | Leu | Ser | Val | Tyr | Val |
|---|---|---|---|---|---|---|---|---|---|---|---|---|---|---|---|
| 145 |   |   |   |   | 150 |   |   |   |   | 155 |   |   |   |   | 160 |

| Gln | Ala | Ala | Asn | Leu | His | Leu | Ser | Leu | Leu | Arg | Asp | Ala | Val | Ser | Phe |
|---|---|---|---|---|---|---|---|---|---|---|---|---|---|---|---|

```
                                  165                           170                                 175
        Gly  Gln  Gly  Trp  Gly  Leu  Asp  Ile  Ala  Thr  Val  Asn  Asn  His  Tyr  Asn
                       180                      185                           190

Arg  Leu  Ile  Asn  Leu  Ile  His  Arg  Tyr  Thr  Lys  His  Cys  Leu  Asp  Thr
                  195                      200                      205

Tyr  Asn  Gln  Gly  Leu  Glu  Asn  Leu  Arg  Gly  Thr  Asn  Thr  Arg  Gln  Trp
             210                      215                      220

Ala  Arg  Phe  Asn  Gln  Phe  Arg  Arg  Asp  Leu  Thr  Leu  Thr  Val  Leu  Asp
        225                      230                      235                      240

Ile  Val  Ala  Leu  Phe  Pro  Asn  Tyr  Asp  Val  Arg  Thr  Tyr  Pro  Ile  Gln
                            245                      250                      255

Thr  Ser  Ser  Gln  Leu  Thr  Arg  Glu  Ile  Tyr  Thr  Ser  Ser  Val  Ile  Glu
                       260                      265                           270

Asp  Ser  Pro  Val  Ser  Ala  Asn  Ile  Pro  Asn  Gly  Phe  Asn  Arg  Ala  Glu
                       275                      280                      285

Phe  Gly  Val  Arg  Pro  Pro  His  Leu  Met  Asp  Phe  Met  Asn  Ser  Leu  Phe
             290                      295                           300

Val  Thr  Ala  Glu  Thr  Val  Arg  Ser  Gln  Thr  Val  Trp  Gly  Gly  His  Leu
        305                      310                      315                      320

Val  Ser  Ser  Arg  Asn  Thr  Ala  Gly  Asn  Arg  Ile  Asn  Phe  Pro  Ser  Tyr
                            325                      330                      335

Gly  Val  Phe  Asn  Pro  Gly  Gly  Ala  Ile  Trp  Ile  Ala  Asp  Glu  Asp  Pro
                            340                      345                      350

Arg  Pro  Phe  Tyr  Arg  Thr  Leu  Ser  Asp  Pro  Val  Phe  Val  Arg  Gly  Gly
                       355                      360                      365

Phe  Gly  Asn  Pro  His  Tyr  Val  Leu  Gly  Leu  Arg  Gly  Val  Ala  Phe  Gln
             370                           375                      380

Gln  Thr  Gly  Thr  Asn  His  Thr  Arg  Thr  Phe  Arg  Asn  Ser  Gly  Thr  Ile
        385                           390                      395                 400

Asp  Ser  Leu  Asp  Glu  Ile  Pro  Pro  Gln  Asp  Asn  Ser  Gly  Ala  Pro  Trp
                            405                      410                           415

Asn  Asp  Tyr  Ser  His  Val  Leu  Asn  His  Val  Thr  Phe  Val  Arg  Trp  Pro
                       420                      425                           430

Gly  Glu  Ile  Ser  Gly  Ser  Asp  Ser  Trp  Arg  Ala  Pro  Met  Phe  Ser  Trp
                       435                      440                      445

Thr  His  Arg  Ser  Ala  Thr  Pro  Thr  Asn  Thr  Ile  Asp  Pro  Glu  Arg  Ile
             450                      455                      460

Thr  Gln  Ile  Pro  Leu  Val  Lys  Ala  His  Thr  Leu  Gln  Ser  Gly  Thr  Thr
        465                      470                      475                      480

Val  Val  Arg  Gly  Pro  Gly  Phe  Thr  Gly  Gly  Asp  Ile  Leu  Arg  Arg  Thr
                            485                      490                      495

Ser  Gly  Gly  Pro  Phe  Ala  Tyr  Thr  Ile  Val  Asn  Ile  Asn  Gly  Gln  Leu
                       500                      505                      510

Pro  Gln  Arg  Tyr  Arg  Ala  Arg  Ile  Arg  Tyr  Ala  Ser  Thr  Thr  Asn  Leu
                  515                      520                      525

Arg  Ile  Tyr  Val  Thr  Val  Ala  Gly  Glu  Arg  Ile  Phe  Ala  Gly  Gln  Phe
             530                      535                      540

Asn  Lys  Thr  Met  Asp  Thr  Gly  Asp  Pro  Leu  Thr  Phe  Gln  Ser  Phe  Ser
        545                      550                      555                      560

Tyr  Ala  Thr  Ile  Asn  Thr  Ala  Phe  Thr  Phe  Pro  Met  Ser  Gln  Ser  Ser
                            565                      570                      575

Phe  Thr  Val  Gly  Ala  Asp  Thr  Phe  Ser  Ser  Gly  Asn  Glu  Val  Tyr  Ile
                       580                      585                      590
```

```
Asp Arg Phe Glu Leu Ile Pro Val Thr Ala Thr Leu Glu Ala Glu Tyr
        595                 600                 605
Asn Leu Glu Arg Ala Gln Glu Ala Val Asn Ala Leu Phe Thr Ser Pro
610                 615                 620
Asn Gln Leu Gly Ile Lys Thr Asn Val Thr Asp Tyr His Ile Asp Gln
625                 630                 635                 640
Val Ser Asn Leu Val Thr Cys Leu Ser Asp Glu Phe Cys Leu Asp Glu
                645                 650                 655
Lys Arg Glu Leu Ser Glu Lys Val Lys His Ala Asn Gly Leu Ser Asp
            660                 665                 670
Glu Arg Asn Leu Leu Gln Asp Ser Asn Phe Lys Asp Ile Asn Arg Gln
            675                 680                 685
Pro Asp Arg Gly Trp Gly Gly Ser Thr Gly Ile Thr Ile Gln Arg Gly
        690                 695                 700
Asp Asp Val Phe Lys Glu Asn Tyr Val Thr Leu Pro Gly Thr Phe Asp
705                 710                 715                 720
Glu Cys Tyr Leu Thr Tyr Leu Tyr Gln Lys Ile Asp Glu Ser Lys Leu
                725                 730                 735
Lys Pro Tyr Thr Arg Tyr Glu Leu Arg Gly Tyr Ile Glu Asp Ser Gln
                740                 745                 750
Asp Leu Glu Ile Tyr Leu Ile Arg Tyr Asn Ala Lys His Glu Thr Val
            755                 760                 765
Asn Val Leu Gly Thr Gly Ser Leu Trp Arg Leu Ser Phe Glu Ser Ser
770                 775                 780
Ile Arg Lys Cys Gly Glu Pro Asn Arg Cys Ala Pro His Leu Glu Trp
785                 790                 795                 800
Asn Pro Asp Leu Asp Cys Ser Cys Arg Asp Gly Glu Lys Cys Ala His
                805                 810                 815
His Ser His His Phe Ser Leu Asp Ile Asp Val Gly Cys Ile Asp Leu
            820                 825                 830
Asn Glu Asp Leu Asp Val Trp Val Ile Phe Lys Ile Lys Thr Gln Asp
            835                 840                 845
Gly His Glu Arg Leu Gly Ile Leu Glu Phe Leu Glu Gly Arg Ala Pro
    850                 855                 860
Leu Val Gly Glu Ala Leu Ala Arg Val Lys Arg Ala Glu Lys Lys Trp
865                 870                 875                 880
Arg Asp Lys Arg Glu Lys Leu Gln Leu Glu Thr Asn Ile Val Tyr Lys
                885                 890                 895
Glu Ala Lys Glu Ser Val Asp Ala Leu Phe Val Asn Ser Gln Tyr Asp
                900                 905                 910
Gln Leu Gln Ala Asp Thr Asn Ile Ala Met Ile His Thr Ala Asp Lys
            915                 920                 925
Arg Val His Arg Ile Gln Glu Ala Tyr Leu Pro Glu Leu Ser Val Ile
930                 935                 940
Pro Gly Val Asn Val Gly Ile Phe Glu Glu Leu Lys Gly Arg Ile Phe
945                 950                 955                 960
Thr Ala Phe Phe Leu Tyr Asp Ala Arg Asn Val Ile Lys Asn Gly Asp
                965                 970                 975
Phe Asn Asn Gly Leu Ser Cys Trp Asn Val Lys Gly His Val Asp Val
            980                 985                 990
Glu Glu Gln Asn Asn Gln Arg Ser Val Leu Val Val Pro Glu Trp Glu
            995                 1000                1005
Ala Glu Val Ser Gln Glu Val Arg Val Cys Pro Gly Arg Gly Tyr Ile
        1010                1015                1020
```

-continued

```
Leu Arg Val Thr Ala Tyr Lys Glu Gly Tyr Gly Thr Gly Cys Val Thr
1025                1030                1035                1040

Ile His Glu Ile Glu Asn Asn Thr Asp Glu Leu Lys Phe Ser Asn Phe
                1045                1050                1055

Val Glu Glu Glu Val Tyr Pro Asn Asn Thr Val Thr Cys Asn Asp Tyr
                1060            1065                1070

Thr Ala Asn Gln Glu Glu Tyr Gly Gly Ala Tyr Thr Ser Cys Asn Arg
            1075                1080                1085

Gly Tyr Asp Glu Thr Tyr Gly Ser Asn Tyr Ser Val Pro Ala Asp Tyr
        1090                1095                1100

Ala Ser Val Tyr Glu Glu Lys Ala Tyr Thr Asp Gly Arg Arg Asp Asn
1105                1110                1115                1120

Pro Cys Glu Ser Asn Arg Gly Tyr Gly Asp Tyr Thr Pro Leu Pro Ala
                1125                1130                1135

Gly Tyr Val Thr Lys Gln Leu Glu Tyr Phe Pro Glu Thr Asp Lys Val
            1140                1145                1150

Trp Ile Glu Ile Gly Glu Thr Glu Gly Thr Phe Ile Val Asp Ser Val
            1155                1160                1165

Glu Leu Leu Leu Met Glu Glu
    1170                1175
```

(2) INFORMATION FOR SEQ ID NO:37:

(i) SEQUENCE CHARACTERISTICS:
        (A) LENGTH: 1148 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:37:

```
Met Glu Asn Asn Ile Gln Asn Gln Cys Val Pro Tyr Asn Cys Leu Asn
1               5               10              15

Asn Pro Glu Val Glu Ile Leu Asn Glu Glu Arg Ser Thr Gly Arg Leu
            20              25              30

Pro Leu Asp Ile Ser Leu Ser Leu Thr Arg Phe Leu Leu Ser Glu Phe
        35              40              45

Val Pro Gly Val Gly Val Ala Phe Gly Leu Phe Asp Leu Ile Trp Gly
50              55              60

Phe Ile Thr Pro Ser Asp Trp Ser Leu Phe Leu Leu Gln Ile Glu Gln
65              70              75              80

Leu Ile Glu Gln Arg Ile Glu Thr Leu Glu Arg Asn Arg Ala Ile Thr
                85              90              95

Thr Leu Arg Gly Leu Ala Asp Ser Tyr Glu Ile Tyr Ile Glu Ala Leu
            100             105             110

Arg Glu Trp Glu Ala Asn Pro Asn Asn Ala Gln Leu Arg Glu Asp Val
            115             120             125

Arg Ile Arg Phe Ala Asn Thr Asp Asp Ala Leu Ile Thr Ala Ile Asn
        130             135             140

Asn Phe Thr Leu Thr Ser Phe Glu Ile Pro Leu Leu Ser Val Tyr Val
145             150             155             160

Gln Ala Ala Asn Leu His Leu Ser Leu Leu Arg Asp Ala Val Ser Phe
                165             170             175

Gly Gln Gly Trp Gly Leu Asp Ile Ala Thr Val Asn Asn His Tyr Asn
            180             185             190
```

```
Arg  Leu  Ile  Asn  Leu  Ile  His  Arg  Tyr  Thr  Lys  His  Cys  Leu  Asp  Thr
          195                      200                     205

Tyr  Asn  Gln  Gly  Leu  Glu  Asn  Leu  Arg  Gly  Thr  Asn  Thr  Arg  Gln  Trp
     210                      215                     220

Ala  Arg  Phe  Asn  Gln  Phe  Arg  Arg  Asp  Leu  Thr  Leu  Thr  Val  Leu  Asp
225                      230                     235                          240

Ile  Val  Ala  Leu  Phe  Pro  Asn  Tyr  Asp  Val  Arg  Thr  Tyr  Pro  Ile  Gln
               245                     250                          255

Thr  Ser  Ser  Gln  Leu  Thr  Arg  Glu  Ile  Tyr  Thr  Ser  Ser  Val  Ile  Glu
               260                     265                     270

Asp  Ser  Pro  Val  Ser  Ala  Asn  Ile  Pro  Asn  Gly  Phe  Asn  Arg  Ala  Glu
          275                      280                     285

Phe  Gly  Val  Arg  Pro  Pro  His  Leu  Met  Asp  Phe  Met  Asn  Ser  Leu  Phe
     290                      295                     300

Val  Thr  Ala  Glu  Thr  Val  Arg  Ser  Gln  Thr  Val  Trp  Gly  Gly  His  Leu
305                      310                     315                          320

Val  Ser  Ser  Arg  Asn  Thr  Ala  Gly  Asn  Arg  Ile  Asn  Phe  Pro  Ser  Tyr
               325                     330                          335

Gly  Val  Phe  Asn  Pro  Gly  Gly  Ala  Ile  Trp  Ile  Ala  Asp  Glu  Asp  Pro
               340                     345                          350

Arg  Pro  Phe  Tyr  Arg  Thr  Leu  Ser  Asp  Pro  Val  Phe  Val  Arg  Gly  Gly
          355                     360                     365

Phe  Gly  Asn  Pro  His  Tyr  Val  Leu  Gly  Leu  Arg  Gly  Val  Ala  Phe  Gln
     370                      375                     380

Gln  Thr  Gly  Thr  Asn  His  Thr  Arg  Thr  Phe  Arg  Asn  Ser  Gly  Thr  Ile
385                      390                     395                          400

Asp  Ser  Leu  Asp  Glu  Ile  Pro  Pro  Gln  Asp  Asn  Ser  Gly  Ala  Pro  Trp
               405                     410                          415

Asn  Asp  Tyr  Ser  His  Val  Leu  Asn  His  Val  Thr  Phe  Val  Arg  Trp  Pro
               420                     425                     430

Gly  Glu  Ile  Ser  Gly  Ser  Asp  Ser  Trp  Arg  Ala  Pro  Met  Phe  Ser  Trp
          435                     440                     445

Thr  His  Arg  Ser  Ala  Thr  Pro  Thr  Asn  Thr  Ile  Asp  Pro  Glu  Arg  Ile
     450                      455                     460

Thr  Gln  Ile  Pro  Leu  Val  Lys  Ala  His  Thr  Leu  Gln  Ser  Gly  Thr  Thr
465                      470                     475                          480

Val  Val  Arg  Gly  Pro  Gly  Phe  Thr  Gly  Gly  Asp  Ile  Leu  Arg  Arg  Thr
               485                     490                          495

Ser  Gly  Gly  Pro  Phe  Ala  Tyr  Thr  Ile  Val  Asn  Ile  Asn  Gly  Gln  Leu
               500                     505                     510

Pro  Gln  Arg  Tyr  Arg  Ala  Arg  Ile  Arg  Tyr  Ala  Ser  Thr  Thr  Asn  Leu
          515                     520                     525

Arg  Ile  Tyr  Val  Thr  Val  Ala  Gly  Glu  Arg  Ile  Phe  Ala  Gly  Gln  Phe
     530                      535                     540

Asn  Lys  Thr  Met  Asp  Thr  Gly  Asp  Pro  Leu  Thr  Phe  Gln  Ser  Phe  Ser
545                      550                     555                          560

Tyr  Ala  Thr  Ile  Asn  Thr  Ala  Phe  Thr  Phe  Pro  Met  Ser  Gln  Ser  Ser
               565                     570                          575

Phe  Thr  Val  Gly  Ala  Asp  Thr  Phe  Ser  Ser  Gly  Asn  Glu  Val  Tyr  Ile
               580                     585                     590

Asp  Arg  Phe  Glu  Leu  Ile  Pro  Val  Thr  Ala  Thr  Phe  Glu  Ala  Glu  Tyr
          595                     600                     605

Asp  Leu  Glu  Arg  Ala  Gln  Lys  Ala  Val  Asn  Glu  Leu  Phe  Thr  Ser  Ile
     610                      615                     620
```

-continued

| | | | | | | | | | | | | | |
|---|---|---|---|---|---|---|---|---|---|---|---|---|---|
| Asn | Gln | Ile | Gly | Leu | Lys | Thr | Asp | Val | Thr | Asp | Tyr | His | Ile | Asp | Arg |
| 625 | | | | | 630 | | | | 635 | | | | | | 640 |
| Val | Ser | Asn | Leu | Val | Glu | Cys | Leu | Ser | Asp | Glu | Phe | Cys | Leu | Asp | Glu |
| | | | | 645 | | | | 650 | | | | | 655 | | |
| Lys | Glu | Glu | Leu | Ser | Glu | Lys | Val | Lys | His | Ala | Lys | Arg | Leu | Ser | Asp |
| | | | 660 | | | | 665 | | | | | 670 | | | |
| Glu | Arg | Asn | Leu | Leu | Gln | Asp | Pro | Asn | Phe | Arg | Gly | Ile | Asn | Arg | Gln |
| | | 675 | | | | 680 | | | | | 685 | | | | |
| Leu | Asp | Arg | Gly | Trp | Arg | Gly | Ser | Thr | Asp | Ile | Thr | Ile | Gln | Gly | Gly |
| | 690 | | | | 695 | | | | | 700 | | | | | |
| Asp | Asp | Val | Phe | Lys | Glu | Asn | Tyr | Val | Thr | Leu | Ser | Gly | Thr | Phe | Asp |
| 705 | | | | | 710 | | | | 715 | | | | | | 720 |
| Glu | Cys | Tyr | Pro | Thr | Tyr | Leu | Tyr | Gln | Lys | Ile | Asp | Glu | Ser | Lys | Leu |
| | | | | 725 | | | | 730 | | | | | 735 | | |
| Lys | Ala | Tyr | Thr | Arg | Tyr | Gln | Leu | Arg | Gly | Tyr | Ile | Glu | Asp | Ser | Gln |
| | | | 740 | | | | 745 | | | | | 750 | | | |
| Asp | Leu | Glu | Ile | Tyr | Leu | Ile | Arg | Tyr | Asn | Ala | Lys | His | Glu | Thr | Val |
| | | 755 | | | | 760 | | | | | 765 | | | | |
| Asn | Val | Pro | Gly | Thr | Gly | Ser | Leu | Trp | Pro | Leu | Ser | Val | Gln | Ser | Pro |
| | 770 | | | | 775 | | | | | 780 | | | | | |
| Ile | Gly | Lys | Cys | Ala | His | Ser | His | His | Phe | Ser | Leu | Asp | Ile | Asp |
| 785 | | | | | 790 | | | | 795 | | | | | | 800 |
| Val | Gly | Cys | Thr | Asp | Leu | Asn | Glu | Asp | Leu | Gly | Val | Trp | Val | Ile | Phe |
| | | | | 805 | | | | 810 | | | | | 815 | | |
| Lys | Ile | Lys | Thr | Gln | Asp | Gly | His | Ala | Arg | Leu | Gly | Asn | Leu | Glu | Phe |
| | | | 820 | | | | 825 | | | | | 830 | | | |
| Leu | Glu | Glu | Lys | Pro | Leu | Val | Gly | Glu | Ala | Leu | Ala | Arg | Val | Lys | Arg |
| | | 835 | | | | 840 | | | | | 845 | | | | |
| Ala | Glu | Lys | Lys | Trp | Arg | Asp | Lys | Arg | Glu | Lys | Leu | Glu | Trp | Glu | Thr |
| | 850 | | | | 855 | | | | | 860 | | | | | |
| Asn | Ile | Val | Tyr | Lys | Glu | Ala | Lys | Glu | Ser | Val | Asp | Ala | Leu | Phe | Val |
| 865 | | | | | 870 | | | | 875 | | | | | | 880 |
| Asn | Ser | Gln | Tyr | Asp | Arg | Leu | Gln | Ala | Asp | Thr | Asn | Ile | Ala | Met | Ile |
| | | | | 885 | | | | 890 | | | | | 895 | | |
| His | Ala | Ala | Asp | Lys | Arg | Val | His | Ser | Ile | Arg | Glu | Ala | Tyr | Leu | Pro |
| | | | 900 | | | | 905 | | | | | 910 | | | |
| Glu | Leu | Ser | Val | Ile | Pro | Gly | Val | Asn | Ala | Asp | Ile | Phe | Glu | Glu | Leu |
| | | 915 | | | | 920 | | | | | 925 | | | | |
| Glu | Gly | Arg | Ile | Phe | Thr | Ala | Phe | Ser | Leu | Tyr | Asp | Ala | Arg | Asn | Val |
| | 930 | | | | 935 | | | | | 940 | | | | | |
| Ile | Lys | Asn | Gly | Asp | Phe | Asn | Asn | Gly | Leu | Ser | Cys | Trp | Asn | Val | Lys |
| 945 | | | | | 950 | | | | 955 | | | | | | 960 |
| Gly | His | Val | Asp | Val | Glu | Glu | Gln | Asn | Asn | His | Arg | Ser | Val | Leu | Val |
| | | | | 965 | | | | 970 | | | | | 975 | | |
| Val | Pro | Glu | Trp | Glu | Ala | Glu | Val | Ser | Gln | Glu | Val | Arg | Val | Cys | Pro |
| | | | 980 | | | | 985 | | | | | 990 | | | |
| Gly | Arg | Gly | Tyr | Ile | Leu | Arg | Val | Thr | Ala | Tyr | Lys | Glu | Gly | Tyr | Gly |
| | | 995 | | | | 1000 | | | | | 1005 | | | | |
| Glu | Gly | Cys | Val | Thr | Ile | His | Glu | Ile | Glu | Asn | Asn | Thr | Asp | Glu | Leu |
| | | 1010 | | | | 1015 | | | | | 1020 | | | | |
| Lys | Phe | Ser | Asn | Cys | Val | Glu | Glu | Glu | Val | Tyr | Pro | Asn | Asn | Thr | Val |
| 1025 | | | | | 1030 | | | | 1035 | | | | | | 1040 |
| Thr | Cys | Asn | Asp | Tyr | Thr | Ala | Thr | Gln | Glu | Glu | Tyr | Glu | Gly | Thr | Tyr |

|     |     |     |     | 1045 |     |     |     |     | 1050 |     |     |     |     | 1055 |
| --- | --- | --- | --- | --- | --- | --- | --- | --- | --- | --- | --- | --- | --- | --- |

Thr Ser Arg Asn Arg Gly Tyr Asp Gly Ala Tyr Glu Ser Asn Ser Ser
            1060                1065              1070

Val Pro Ala Asp Tyr Ala Ser Ala Tyr Glu Glu Lys Ala Tyr Thr Asp
        1075                1080              1085

Gly Arg Arg Asp Asn Pro Cys Glu Ser Asn Arg Gly Tyr Gly Asp Tyr
    1090                1095              1100

Thr Pro Leu Pro Ala Gly Tyr Val Thr Lys Glu Leu Glu Tyr Phe Pro
1105            1110              1115                    1120

Glu Thr Asp Lys Val Trp Ile Glu Ile Gly Glu Thr Glu Gly Thr Phe
                1125              1130              1135

Ile Val Asp Ser Val Glu Leu Leu Leu Met Glu Glu
            1140              1145

(2) INFORMATION FOR SEQ ID NO:38:

(i) SEQUENCE CHARACTERISTICS:
      (A) LENGTH: 1148 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:38:

Met Glu Asn Asn Ile Gln Asn Gln Cys Val Pro Tyr Asn Cys Leu Asn
1               5                   10                  15

Asn Pro Glu Val Glu Ile Leu Asn Glu Glu Arg Ser Thr Gly Arg Leu
            20              25                  30

Pro Leu Asp Ile Ser Leu Ser Leu Thr Arg Phe Leu Leu Ser Glu Phe
        35                  40                  45

Val Pro Gly Val Gly Val Ala Phe Gly Leu Phe Asp Leu Ile Trp Gly
    50              55                  60

Phe Ile Thr Pro Ser Asp Trp Ser Leu Phe Leu Leu Gln Ile Glu Gln
65              70                  75                      80

Leu Ile Glu Gln Arg Ile Glu Thr Leu Glu Arg Asn Arg Ala Ile Thr
                85                  90                  95

Thr Leu Arg Gly Leu Ala Asp Ser Tyr Glu Ile Tyr Ile Glu Ala Leu
            100                 105                 110

Arg Glu Trp Glu Ala Asn Pro Asn Asn Ala Gln Leu Arg Glu Asp Val
            115                 120                 125

Arg Ile Arg Phe Ala Asn Thr Asp Asp Ala Leu Ile Thr Ala Ile Asn
        130                 135                 140

Asn Phe Thr Leu Thr Ser Phe Glu Ile Pro Leu Leu Ser Val Tyr Val
145                 150                 155                 160

Gln Ala Ala Asn Leu His Leu Ser Leu Leu Arg Asp Ala Val Ser Phe
                165                 170                 175

Gly Gln Gly Trp Gly Leu Asp Ile Ala Thr Val Asn Asn His Tyr Asn
            180                 185                 190

Arg Leu Ile Asn Leu Ile His Arg Tyr Thr Lys His Cys Leu Asp Thr
        195                 200                 205

Tyr Asn Gln Gly Leu Glu Asn Leu Arg Gly Thr Asn Thr Arg Gln Trp
    210                 215                 220

Ala Arg Phe Asn Gln Phe Arg Arg Asp Leu Thr Leu Thr Val Leu Asp
225                 230                 235                 240

Ile Val Ala Leu Phe Pro Asn Tyr Asp Val Arg Thr Tyr Pro Ile Gln
            245                 250                 255

```
Thr  Ser  Ser  Gln  Leu  Thr  Arg  Glu  Ile  Tyr  Thr  Ser  Ser  Val  Ile  Glu
               260                 265                      270

Asp  Ser  Pro  Val  Ser  Ala  Asn  Ile  Pro  Asn  Gly  Phe  Asn  Arg  Ala  Glu
          275                 280                      285

Phe  Gly  Val  Arg  Pro  Pro  His  Leu  Met  Asp  Phe  Met  Asn  Ser  Leu  Phe
     290                 295                      300

Val  Thr  Ala  Glu  Thr  Val  Arg  Ser  Gln  Thr  Val  Trp  Gly  Gly  His  Leu
305                      310                      315                      320

Val  Ser  Ser  Arg  Asn  Thr  Ala  Gly  Asn  Arg  Ile  Asn  Phe  Pro  Ser  Tyr
               325                 330                      335

Gly  Val  Phe  Asn  Pro  Gly  Gly  Ala  Ile  Trp  Ile  Ala  Asp  Glu  Asp  Pro
               340                 345                      350

Arg  Pro  Phe  Tyr  Arg  Thr  Leu  Ser  Asp  Pro  Val  Phe  Val  Arg  Gly  Gly
          355                 360                      365

Phe  Gly  Asn  Pro  His  Tyr  Val  Leu  Gly  Leu  Arg  Gly  Val  Ala  Phe  Gln
     370                 375                      380

Gln  Thr  Gly  Thr  Asn  His  Thr  Arg  Thr  Phe  Arg  Asn  Ser  Gly  Thr  Ile
385                      390                      395                      400

Asp  Ser  Leu  Asp  Glu  Ile  Pro  Pro  Gln  Asp  Asn  Ser  Gly  Ala  Pro  Trp
               405                 410                      415

Asn  Asp  Tyr  Ser  His  Val  Leu  Asn  His  Val  Thr  Phe  Val  Arg  Trp  Pro
               420                 425                      430

Gly  Glu  Ile  Ser  Gly  Ser  Asp  Ser  Trp  Arg  Ala  Pro  Met  Phe  Ser  Trp
          435                 440                      445

Thr  His  Arg  Ser  Ala  Thr  Pro  Thr  Asn  Thr  Ile  Asp  Pro  Glu  Arg  Ile
450                      455                      460

Thr  Gln  Ile  Pro  Leu  Val  Lys  Ala  His  Thr  Leu  Gln  Ser  Gly  Thr  Thr
465                      470                      475                      480

Val  Val  Arg  Gly  Pro  Gly  Phe  Thr  Gly  Gly  Asp  Ile  Leu  Arg  Arg  Thr
                    485                 490                      495

Ser  Gly  Gly  Pro  Phe  Ala  Tyr  Thr  Ile  Val  Asn  Ile  Asn  Gly  Gln  Leu
               500                 505                      510

Pro  Gln  Arg  Tyr  Arg  Ala  Arg  Ile  Arg  Tyr  Ala  Ser  Thr  Thr  Asn  Leu
          515                 520                      525

Arg  Ile  Tyr  Val  Thr  Val  Ala  Gly  Glu  Arg  Ile  Phe  Ala  Gly  Gln  Phe
     530                 535                      540

Asn  Lys  Thr  Met  Asp  Thr  Gly  Asp  Pro  Leu  Thr  Phe  Gln  Ser  Phe  Ser
545                      550                      555                      560

Tyr  Ala  Thr  Ile  Asn  Thr  Ala  Phe  Thr  Phe  Pro  Met  Ser  Gln  Ser  Ser
               565                 570                      575

Phe  Thr  Val  Gly  Ala  Asp  Thr  Phe  Ser  Ser  Gly  Asn  Glu  Val  Tyr  Ile
               580                 585                      590

Asp  Arg  Phe  Glu  Leu  Ile  Pro  Val  Thr  Ala  Thr  Phe  Glu  Ala  Glu  Tyr
          595                 600                      605

Asp  Leu  Glu  Arg  Ala  Gln  Lys  Ala  Val  Asn  Glu  Leu  Phe  Thr  Ser  Thr
     610                 615                      620

Asn  Gln  Ile  Gly  Leu  Lys  Thr  Asp  Val  Thr  Asp  Tyr  His  Ile  Asp  Arg
625                      630                      635                      640

Val  Ser  Asn  Leu  Val  Glu  Cys  Leu  Ser  Asp  Glu  Phe  Cys  Leu  Asp  Glu
               645                 650                      655

Lys  Glu  Glu  Leu  Ser  Glu  Lys  Val  Lys  His  Ala  Lys  Arg  Leu  Ser  Asp
               660                 665                      670

Glu  Arg  Asn  Leu  Leu  Gln  Asp  Pro  Asn  Phe  Arg  Gly  Ile  Asn  Arg  Gln
```

-continued

```
                         675                          680                            685
Leu Asp Arg Gly Trp Arg Gly Ser Thr Asp Ile Thr Ile Gln Gly Gly
    690                     695                    700
Asp Asp Val Phe Lys Glu Asn Tyr Val Thr Leu Ser Gly Thr Phe Asp
705                 710                 715                         720
Glu Cys Tyr Pro Thr Tyr Leu Tyr Gln Lys Ile Asp Glu Ser Lys Leu
                725                 730                         735
Lys Ala Tyr Thr Arg Tyr Gln Leu Arg Gly Tyr Ile Glu Asp Ser Gln
                740                 745                 750
Asp Leu Glu Ile Tyr Leu Ile Arg Tyr Asn Ala Lys His Glu Thr Val
            755                 760                 765
Asn Val Pro Gly Thr Gly Ser Leu Trp Pro Leu Ser Val Gln Ser Pro
770                         775                 780
Ile Gly Lys Cys Ala His His Ser His His Phe Ser Leu Asp Ile Asp
785                 790                 795                         800
Val Gly Cys Thr Asp Leu Asn Glu Asp Leu Gly Val Trp Val Ile Phe
                805                 810                         815
Lys Ile Lys Thr Gln Asp Gly His Ala Arg Leu Gly Asn Leu Glu Phe
                820                 825                 830
Leu Glu Glu Lys Pro Leu Val Gly Glu Ala Leu Ala Arg Val Lys Arg
            835                 840                 845
Ala Glu Lys Lys Trp Arg Asp Lys Arg Glu Lys Leu Glu Trp Glu Thr
    850                 855                 860
Asn Ile Val Tyr Lys Glu Ala Lys Glu Ser Val Asp Ala Leu Phe Val
865                 870                 875                         880
Asn Ser Gln Tyr Asp Arg Leu Gln Ala Asp Thr Asn Ile Ala Met Ile
                885                 890                         895
His Ala Ala Asp Lys Arg Val His Ser Ile Arg Glu Ala Tyr Leu Pro
                900                 905                 910
Glu Leu Ser Val Ile Pro Gly Val Asn Ala Asp Ile Phe Glu Glu Leu
            915                 920                 925
Glu Gly Arg Ile Phe Thr Ala Phe Ser Leu Tyr Asp Ala Arg Asn Val
    930                     935                 940
Ile Lys Asn Gly Asp Phe Asn Asn Gly Leu Ser Cys Trp Asn Val Lys
945                 950                 955                         960
Gly His Val Asp Val Glu Glu Gln Asn Asn His Arg Ser Val Leu Val
                965                 970                 975
Val Pro Glu Trp Glu Ala Glu Val Ser Gln Glu Val Arg Val Cys Pro
            980                 985                         990
Gly Arg Gly Tyr Ile Leu Arg Val Thr Ala Tyr Lys Glu Gly Tyr Gly
    995                     1000                1005
Glu Gly Cys Val Thr Ile His Glu Ile Glu Asn Asn Thr Asp Glu Leu
    1010                    1015                1020
Lys Phe Ser Asn Cys Val Glu Glu Val Tyr Pro Asn Asn Thr Val
1025                1030                1035                    1040
Thr Cys Asn Asp Tyr Thr Ala Thr Gln Glu Glu Tyr Glu Gly Thr Tyr
                1045                1050                1055
Thr Ser Arg Asn Arg Gly Tyr Asp Gly Ala Tyr Glu Ser Asn Ser Ser
                1060                1065                1070
Val Pro Ala Asp Tyr Ala Ser Ala Tyr Glu Glu Lys Ala Tyr Thr Asp
                1075                1080                1085
Gly Arg Arg Asp Asn Pro Cys Glu Ser Asn Arg Gly Tyr Gly Asp Tyr
    1090                    1095                1100
```

-continued

| Thr | Pro | Leu | Pro | Ala | Gly | Tyr | Val | Thr | Lys | Glu | Leu | Glu | Tyr | Phe | Pro |
|-----|-----|-----|-----|-----|-----|-----|-----|-----|-----|-----|-----|-----|-----|-----|-----|
| 1105 | | | | | 1110 | | | | 1115 | | | | | | 1120 |
| Glu | Thr | Asp | Lys | Val | Trp | Ile | Glu | Ile | Gly | Glu | Thr | Glu | Gly | Thr | Phe |
| | | | | 1125 | | | | | 1130 | | | | | 1135 | |
| Ile | Val | Asp | Ser | Val | Glu | Leu | Leu | Leu | Met | Glu | Glu | | | | |
| | | | 1140 | | | | | 1145 | | | | | | | |